US012606566B2

(12) United States Patent
Xu et al.

(10) Patent No.: US 12,606,566 B2
(45) Date of Patent: Apr. 21, 2026

(54) SUBSTITUTED CYCLOPENTA[4,5] PYRROLO[1,2-A]PYRAZINES AS BRUTON'S TYROSINE KINASE INHIBITORS

(71) Applicants: Shanghai Synergy Pharmaceutical Sciences Co., Ltd., Shanghai (CN); Zhejiang Huahai Pharmaceutical Co., Ltd., Zhejiang (CN)

(72) Inventors: Xin Xu, Shanghai (CN); Jia Chen, Shanghai (CN); Guan Wang, Shanghai (CN); Linli Zhang, Shanghai (CN); Qingyun Jiang, Shanghai (CN); Chenghao Xi, Shanghai (CN); Kang Sun, Shanghai (CN); Xiaojuan Zhang, Shanghai (CN); Chunqiao Chen, Shanghai (CN); Shuai Li, Shanghai (CN); Qiang Li, Shanghai (CN); Liangze Xia, Shanghai (CN); Ying Wang, Shanghai (CN); Xiaoer Xia, Shanghai (CN)

(73) Assignees: SHANGHAI SYNERGY PHARMACEUTICAL SCIENCES CO., LTD., Shanghai (CN); ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 628 days.

(21) Appl. No.: 18/002,133

(22) PCT Filed: Jun. 18, 2021

(86) PCT No.: PCT/CN2021/100901
§ 371 (c)(1),
(2) Date: Dec. 16, 2022

(87) PCT Pub. No.: WO2021/254483
PCT Pub. Date: Dec. 23, 2021

(65) Prior Publication Data

US 2023/0348471 A1 Nov. 2, 2023

(30) Foreign Application Priority Data

Jun. 18, 2020 (CN) ......................... 202010558345.4

(51) Int. Cl.

| | |
|---|---|
| ***A61K 31/4985*** | (2006.01) |
| ***A61P 11/00*** | (2006.01) |
| ***A61P 19/02*** | (2006.01) |
| ***A61P 35/00*** | (2006.01) |
| ***A61P 37/06*** | (2006.01) |
| ***C07D 241/36*** | (2006.01) |
| ***C07D 487/04*** | (2006.01) |
| ***C07D 519/00*** | (2006.01) |

(52) U.S. Cl.
CPC ............ *C07D 487/04* (2013.01); *A61P 11/00* (2018.01); *A61P 19/02* (2018.01); *A61P 35/00* (2018.01); *A61P 37/06* (2018.01); *C07D 519/00* (2013.01)

(58) Field of Classification Search
CPC .......................... A61K 31/4985; C07D 241/36
USPC .......................................... 514/250; 544/344
See application file for complete search history.

(56) References Cited

U.S. PATENT DOCUMENTS 8,716,274 B2 * 5/2014 Crawford ............. C07D 495/04
544/344

FOREIGN PATENT DOCUMENTS

| | | | |
|---|---|---|---|
| CN | 103038233 | A | 4/2013 |
| CN | 104024255 | A | 9/2014 |
| CN | 104105697 | A | 10/2014 |
| CN | 104125959 | A | 10/2014 |
| CN | 110446710 | A | 11/2019 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag Gmbh & Co. KGaA, 2005, Preface.*
Vippagunta, et al. Advanced Drug Delivery Reviews, 48, 2001, 18.*
(Continued)

*Primary Examiner* — Douglas M Willis
(74) *Attorney, Agent, or Firm* — Jason A. Smith; Shumaker, Loop & Kendrick, LLP

(57) ABSTRACT

A compound of formula (I) as Bruton's tyrosine kinase inhibitor, a preparation method therefor, and an application thereof in the field of medicine. The Bruton's tyrosine kinase inhibitor may be used for preventing and/or treating a disease related to Bruton's tyrosine kinase mediation, such as an autoimmune disease, cancer, or an inflammatory disease. Through experimental research, the provided compound has high selectivity with respect to a Bruton's tyrosine kinase target, and can exhibit a uniquely advantageous medicinal effect in an in vivo animal experiment.

(I)

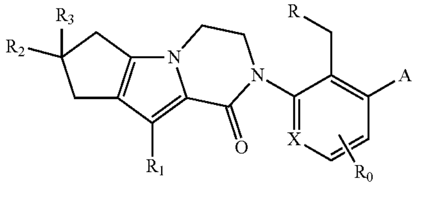

14 Claims, No Drawings

(56) References Cited

OTHER PUBLICATIONS

Wolff, Manfred E., Ed. Burger's Medicinal Chemistry and Drug Discovery—Fifth Edition, vol. 1: Principles and Practice, New York: John Wiley & Sons, 1994, 975-977.*
Crawford, James et al., "Discovery of GDC-0853: a Potent, Selective, and Non-Covalent Bruton's Tyrosine Kinase Inhibitor in Early Clinical Development," Journal of Medicinal Chemistry, 61:2227-2245, (Feb. 19, 2018).
WIPO Application No. PCT/CN2021/100901, PCT International Search Report mailed Sep. 18, 2021.
1st Office Action for China Patent Application No. 202180035678.1 dated Mar. 13, 2024 w/English translation (20 pages).

* cited by examiner

SUBSTITUTED CYCLOPENTA[4,5]PYRROLO[1,2-A]PYRAZINES AS BRUTON'S TYROSINE KINASE INHIBITORS

The present application is a national phase entry of International Application No. PCT/CN2021/100901, filed Jun. 18, 2021, which claims the priority of Chinese Patent Application No. 202010558345.4, filed before the CNIPA on Thursday, Jun. 18, 2020, titled "BRUTON'S TYROSINE KINASE INHIBITOR AND PREPARATION METHOD THEREFOR", which are incorporated herein by reference in their entirety.

FIELD OF THE INVENTION

The present application belongs to the field of medicine and relates to a compounds as a Bruton's tyrosine kinase inhibitor, a preparation method therefor and use thereof in the field of medicine. The compound provided in the present application can be used for preventing and/or treating autoimmune diseases, cancers or inflammatory diseases, etc.

BACKGROUND OF THE INVENTION

Bruton's tyrosine kinase (BTK) is one of the Tec family of cytoplasmic tyrosine kinases (Tec family kinases, TFK). The family has 5 members, including BTK, ITK, TEC, BMX, and TXK, respectively. Among them, BTK is mainly expressed in B cells and myeloid cells, distributed in lymphatic, hematopoietic and hematological systems, but lower levels of BTK expression were also found in T cells and plasma cells.

In B cells BTK is primarily responsible for intra- and extracellular signaling and amplification, and is required for B cell maturation. The upstream signaling receptors include growth factor and cytokine receptors, G protein-coupled receptors such as chemokine receptors, antigen receptors (especially B-cell receptors (BCRs) and integrin). The downstream signalling pathways activated by BTK include the phosphatidylinositol-3 kinase (PI3K)-AKT pathway, phospholipase-C (PLC), protein kinase C and nuclear factor-κB (NF-κB), etc. Therefore, BTK is a key kinase in the B-cell antigen receptor (BCR) signalling pathway, which regulates the proliferation, differentiation and apoptosis of normal B cells. Overexpression of BTK causes abnormal activation of the BCR signalling pathway, resulting in dysfunction of B cells, alteration of immune tolerance and conversion to auto-reactive B cells that secrete large amounts of auto-antibodies to induce autoimmune diseases. It certainly also affects the proliferation, differentiation and apoptosis of B cells, which can lead to various malignant lymphomas.

Most BTK inhibitors for autoimmune diseases are currently in clinical phase I and II, and their main indications include rheumatoid arthritis (RA), systemic lupus erythematosus, psoriasis, urticaria, as well as rhinitis and asthma.

BTK inhibitors are covalently and non-covalently bound to protein kinases, to which Ibrutinib, which was launched in 2013, is a representative for covalently binding and is mainly used for the treatment of various lymphomas. Non-covalently bound BTK inhibitor (GDC-0853) developed by Genentech Inc. (WO2013/067274, WO2013/067260), for the treatment of various immune diseases such as rheumatoid arthritis (RA) and systemic lupus erythematosus, is now in clinical phase II. The selectivity of known BTK inhibitors is ideal, such as the BTK inhibitor (GDC-0853), which still have an inhibitory effect on a variety of kinases (Src, Bmx, Fgr, etc.) in terms of selectivity (J. Med. Chem. 2018, 61, 2227-2245). Therefore, there is a clinical need to develop more BTK inhibitors for the treatment of various immunological diseases, which can overcome various side effects associated with poor selectivity at the same time.

Anew class of BTK inhibitors has been designed and synthesized in the present invention. Such compounds have been experimentally investigated and shown to be highly selective for BTK targets, and in vivo animal studies demonstrate these compounds have excellent pharmacodynamic effects.

SUMMARY OF THE INVENTION

An object of the present application is to provide a compound of formula (I), or a tautomer, mesomer, racemate, enantiomer or diastereoisomer thereof, or mixture thereof, or a pharmaceutically acceptable salt, polymorph, solvate, prodrug, metabolite or isotopic derivative thereof,

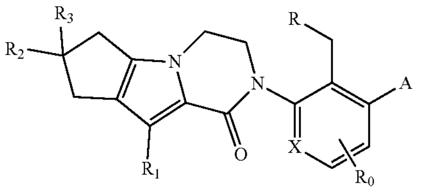

(I)

wherein X is C—$R^a$ or N;

$R^a$ is hydrogen or cyano;

$R_0$ is selected from the group consisting of hydrogen, halogen, hydroxyl, $C_{1-6}$ alkyl, cyano and $C_{1-6}$ alkoxy;

when X is N, $R_0$ is hydrogen; when X is C—$R^a$ and $R^a$ is cyano, $R_0$ is hydrogen;

$R_1$ is selected from the group consisting of hydrogen, deuterium, halogen, cyano, trifluoromethyl, $C_{0-6}$ alkyl-substituted amino, $C_{1-6}$ alkyl and $C_{1-6}$ alkoxy;

$R_2$ and $R_3$ are each independently $C_{1-3}$ alkyl;

R is hydroxyl or halogen, preferably hydroxyl;

A is

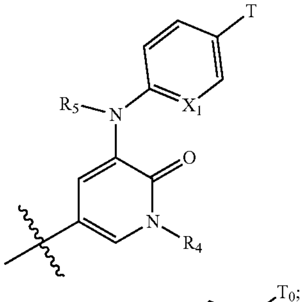

or

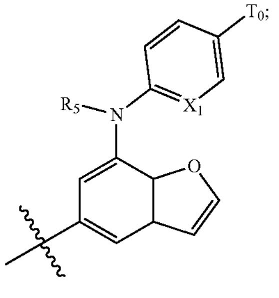

$R_4$ is linear $C_{1-6}$ alkyl or branched $C_{3-6}$ alkyl;

$R_5$ is hydrogen or $C_{1-3}$ alkyl;

$X_1$ is CH or N;

T and $T_0$ are each independently nitrogen-containing 5-6 membered heterocycloalkyl or nitrogen-containing 9-11 membered spirocycloalkyl, wherein the 5-6 membered heterocycloalkyl is unsubstituted, or is substituted by one of $T_1$ and $T_2$, or is substituted by both $T_1$ and $T_2$;

wherein the spirocycloalkyl is not substituted, or is substituted by one of $T_3$ and $T_4$, or is substituted by both $T_3$ and $T_4$;

$T_1$ is $C_{1-6}$ alkyl;

$T_2$ is $C_{1-6}$ alkyl or 3-6 membered heterocycloalkyl;

$T_3$ is hydroxyl or $C_{1-6}$ alkyl; and $T_4$ is $C_{1-6}$ alkyl or 3-6 membered heterocycloalkyl.

T and $T_0$ may further preferably be selected from the group consisting of

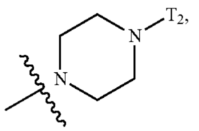

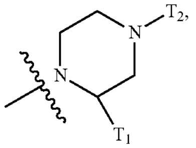

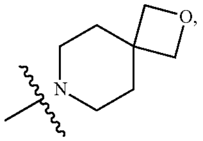

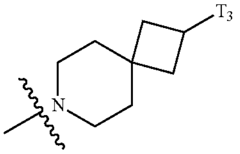

and

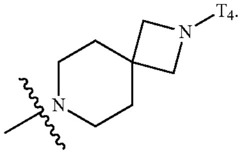

T and $T_0$ can specifically be selected from the group consisting of

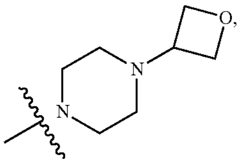

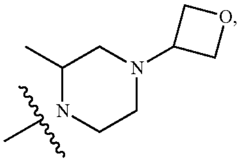

-continued

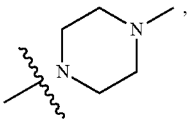

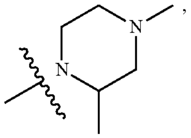

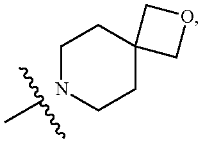

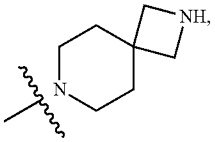

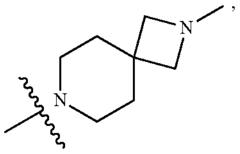

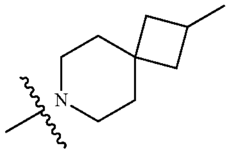

and

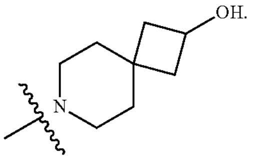

Synthesis Process for the Compounds provided by the Present Application:

The compounds of formulae of the present application can be synthesized according to a variety of reaction processes. Those skilled in the art can easily devise other reaction processes for the compounds by certain preparation methods provided in the Examples herein.

The present application relates to a method for preparing the compound of formula (1) or a pharmaceutically acceptable salt thereof, wherein the compound of formula (I) is prepared by the following schemes:

Scheme 1:
when A is
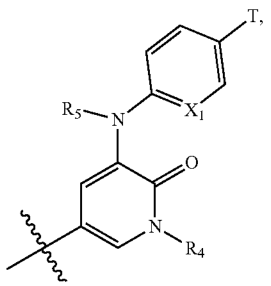
R is hydroxyl, and $R_1$ is halogen or $C_{1-6}$ alkyl, the synthesis route of the compound of formula (I) is as follows:
scheme 2
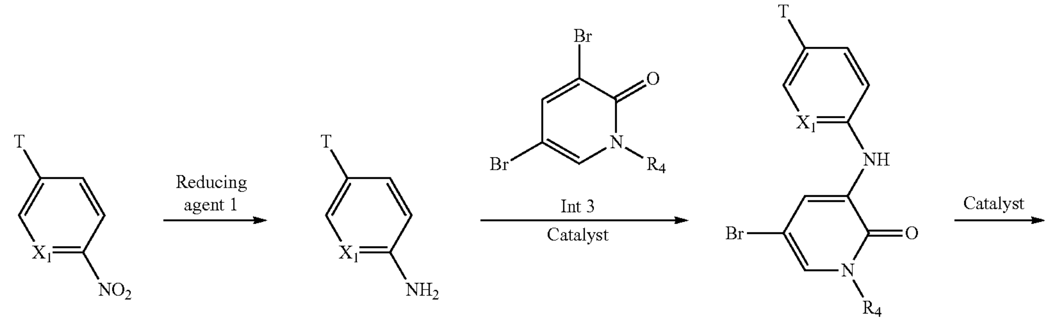
I-1 I-2 I-3
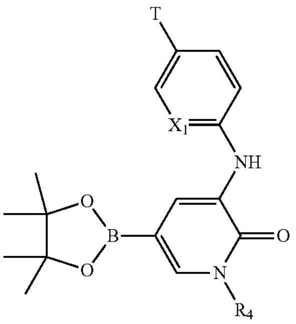
I-4
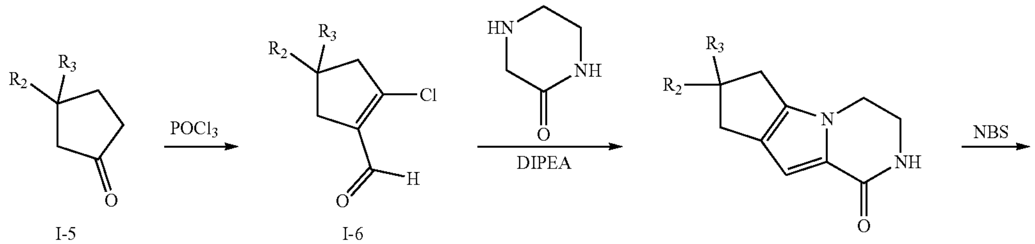
I-5 I-6 I-7

-continued
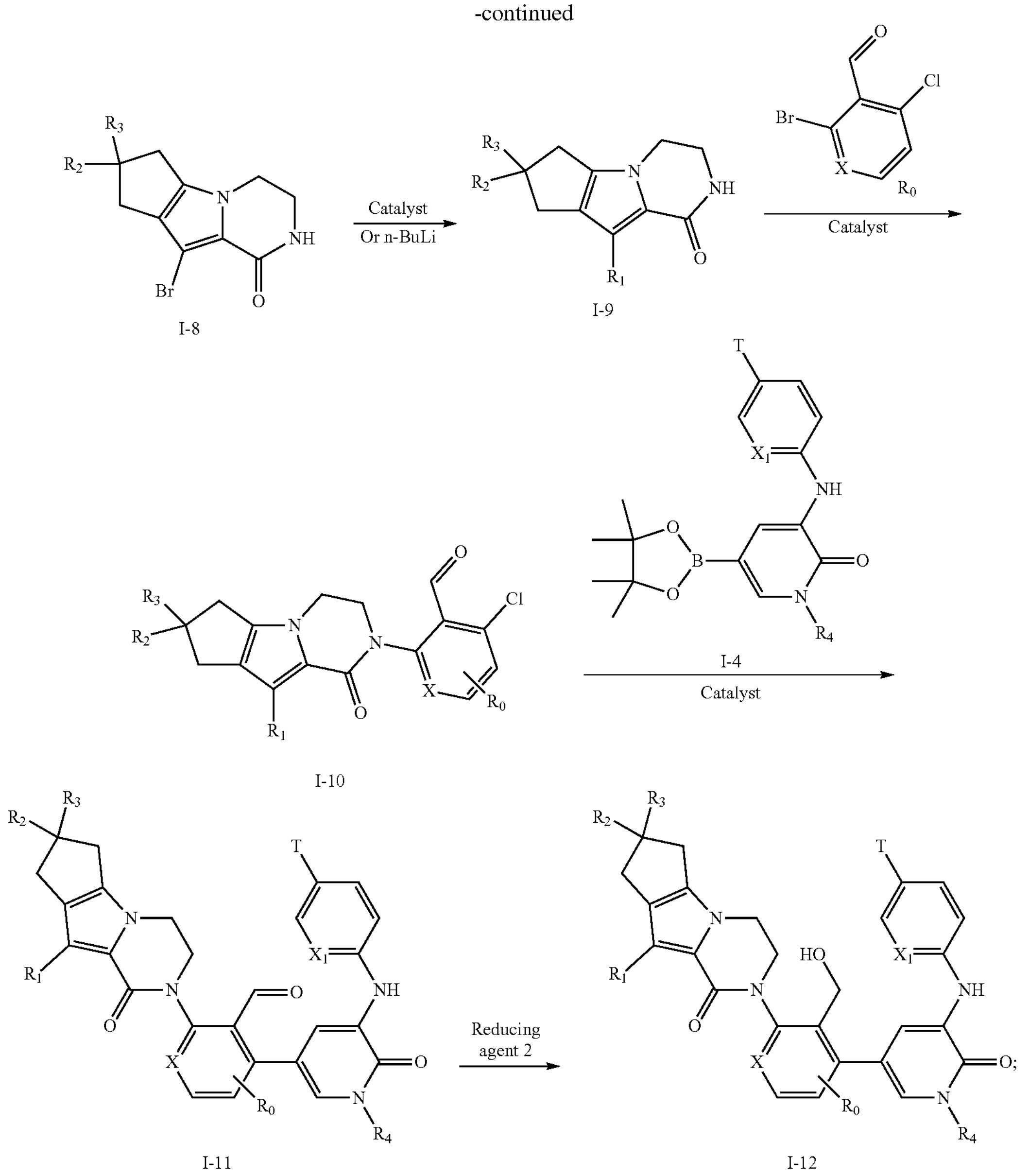
when A is
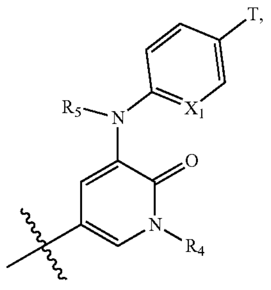
R is hydroxyl, and $R_1$ is hydrogen, the synthesis route of the compound of formula (I) is as follows:

scheme 3
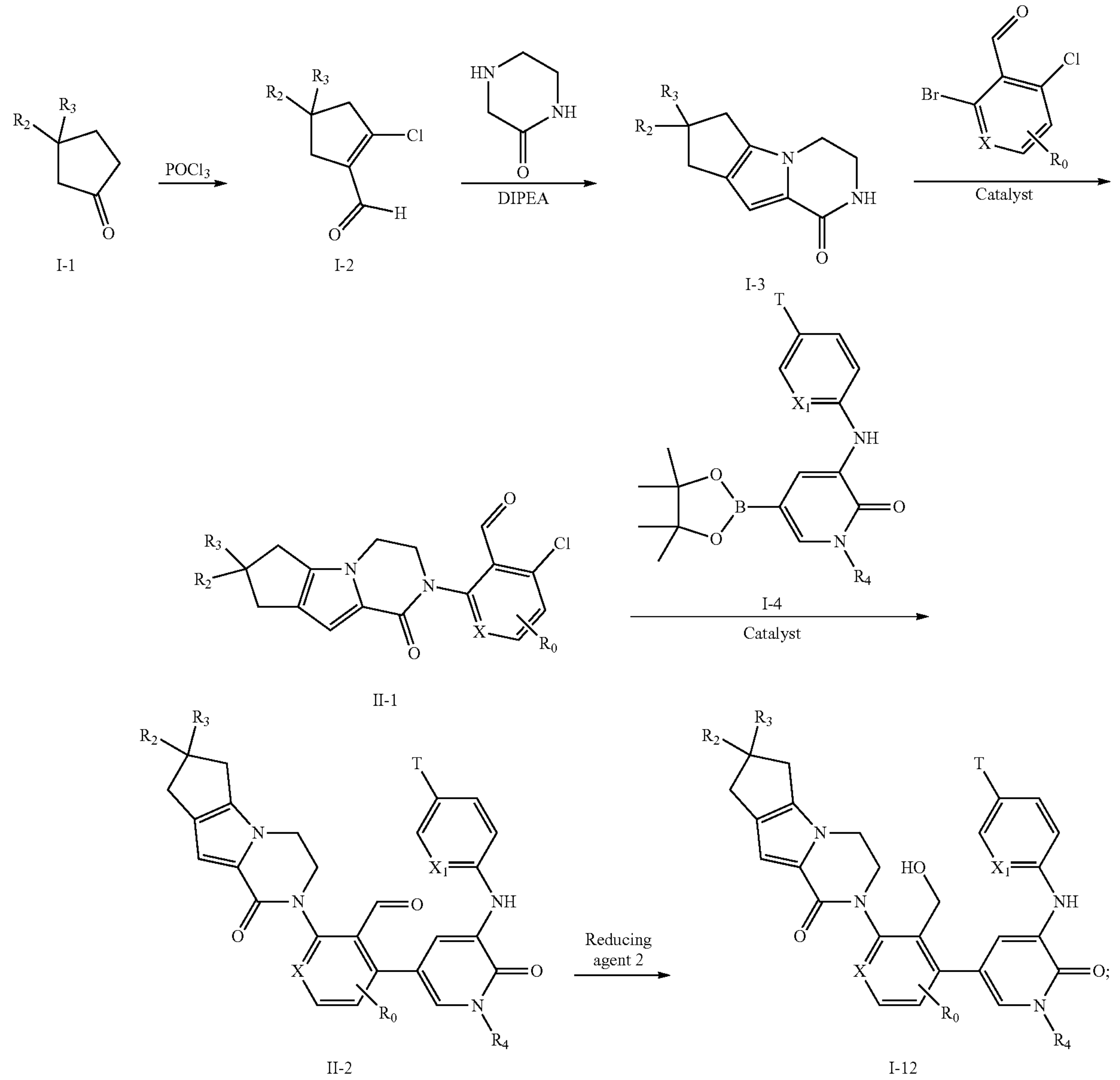
when A is
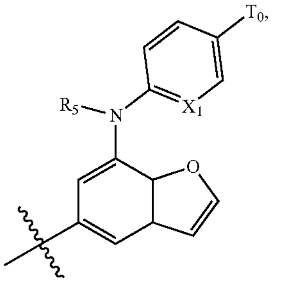
R is hydroxyl, and $R_1$ is hydrogen, the synthesis route of the compound of formula (I) is as follows:
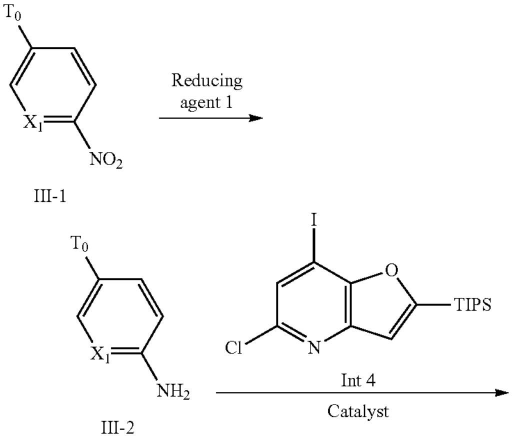

-continued

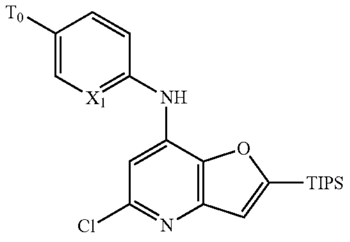

III-3

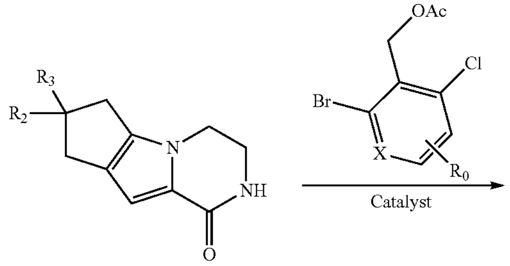

III-4

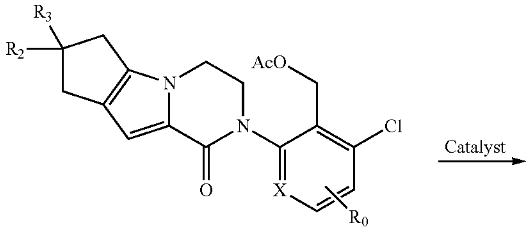

III-5

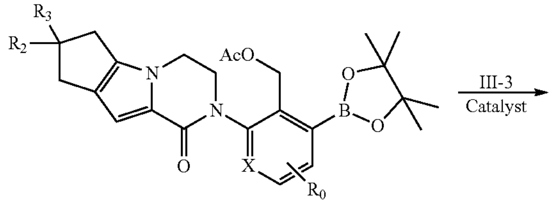

III-6

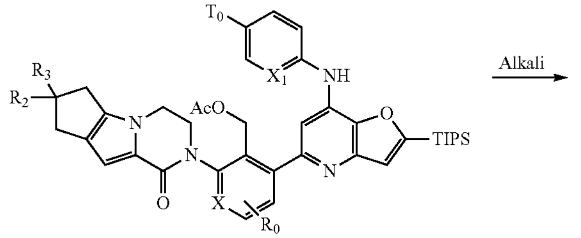

III-7

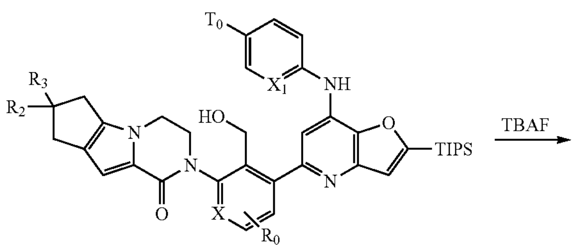

III-8

-continued

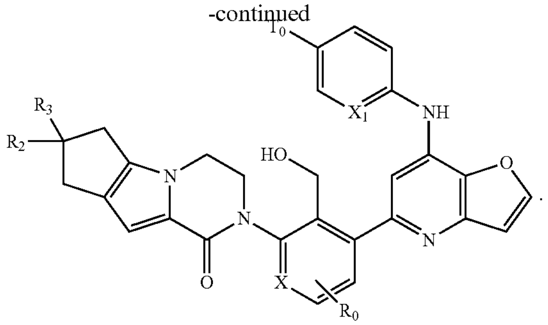

III-9

In scheme 1, the catalyst is selected from the group consisting of tris(dibenzylideneacetone)dipalladium, 4,5-bis(diphenylphosphino)-9,9-dimethylxanthene, palladium acetate, tetrakis(triphenylphosphine)palladium, [1,1'-bis(diphenylphosphino)ferrocene]palladium dichloride, 2-dicyclohexylphosphine-2,4,6-triisopropylbiphenyl, 1,1'-binaphthyl-2,2'-bis(diphenylphosphine), 1,10-phenanthroline, and cuprous iodide; the reducing agent 1 is selected from the group consisting of lithium aluminum tetrahydride, borane tetrahydrofuran, borane dimethyl sulfide, and reducing iron powder; and the reducing agent 2 is selected from the group consisting of sodium borohydride, potassium borohydride, sodium triacetylborohydride, and sodium cyanoborohydride.

In scheme 2 and scheme 3, the catalyst is selected from the group consisting of tris(dibenzylideneacetone)dipalladium, 4,5-bis(diphenylphosphino)-9,9-dimethylxanthene, palladium acetate, tetrakis(triphenylphosphine)palladium, [1,1'-bis(diphenylphosphino)ferrocene]palladium dichloride, 2-dicyclohexylphosphine-2,4,6-triisopropylbiphenyl, 1,1'-binaphthyl-2,2'-bis(diphenylphosphine), 1,10-phenanthroline, and cuprous iodide; the reducing agent 1 is selected from the group consisting of lithium aluminum tetrahydride, borane tetrahydrofuran, borane dimethyl sulfide, and reducing iron powder; and the alkali can be selected from the group consisting of potassium carbonate, caesium carbonate, potassium hydroxide, sodium hydroxide and caesium fluoride.

The present application provides a compound of formula (I) and a pharmaceutically acceptable salt thereof, wherein the compound is specifically:

(S)-9-fluoro-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-9-chloro-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7,9-trimethyl-3,4,7,8-tetrahydro-2H-cyclopenta[4,5]pyrrolo[1,2-a]pyrazin-1(6H)-one;

(S)-2-(3'-(hydroxymethyl)-1-isopropyl-5-((5-(2-methyl-4-(oxetan-3-yl) piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-3-(7,7-dimethyl-1-oxo-1,3,4,6,7,8-hexahydro-2H-cyclopenta[4,5]pyrrolo [1,2-a]pyrazin-2-yl)-4-(hydroxymethyl)-5-(1-methyl-5-((5-(2-methyl-4-(oxetan-3-yl)piperazin-1-yl)pyridin-2-yl)amino)-6-oxo-1,6-dihydropyridin-3-yl)benzonitrile;

(S)-2-(7,7-dimethyl-1-oxo-1,3,4,6,7,8-hexahydro-2H-cyclopenta[4,5]pyrrolo [1,2-a]pyrazin-2-yl)-3-(hydroxymethyl)-4-(1-methyl-5-((5-(2-methyl-4-(oxetan-3-yl)piperazin-1-yl)pyridin-2-yl)amino)-6-oxo-1,6-dihydropyridin-3-yl)benzonitrile;

(S)-4-(7,7-dimethyl-1-oxo-1,3,4,6,7,8-hexahydro-2H-cyclopenta[4,5]pyrrolo [1,2-a]pyrazin-2-yl)-3-(hydroxymethyl)-2-(1-methyl-5-((5-(2-methyl-4-(oxetan-3-yl)piperazin-1-yl)pyridin-2-yl)amino)-6-oxo-1,6-dihydropyridin-3-yl)benzonitrile;

2-(3-(hydroxymethyl)-4-(7-((5-(4-methylpiperazin-1-yl)pyridin-2-yl)amino) furo[3,2-b]pyridin-5-yl)pyridin-2-yl)-7,7-dimethyl-3,4,7,8-tetrahydro-2H-cyclopenta[4,5]pyrrolo[1,2-a]pyrazin-1(6H)-one;

2-(3-(hydroxymethyl)-4-(7-((5-(4-oxetan-3-yl)piperazin-1-yl)pyridin-2-yl) amino)furo[3,2-b]pyridin-5-yl)pyridin-2-yl)-7,7-dimethyl-3,4,7,8-tetrahydro-2H-cyclopenta[4,5]pyrrolo[1,2-a]pyrazin-1(6H)-one;

9-fluoro-2-(3'-(hydroxymethyl)-1-methyl-5-((5-(4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

2-(5-((5-(2-oxa-7-azaspiro[3.5]nonan-7-yl)pyridin-2-yl) amino)-3'-(hydroxymethyl)-1-methyl-6-oxo-1,6-dihydro-[3,4'-bipyridin]-2'-yl)-9-fluoro-7,7-dimethyl-3,4,7,8-tetrahydro-2H-cyclopenta[4,5]pyrrolo[1,2-a]pyrazin-1(6H)-one;

9-fluoro-2-(3'-(hydroxymethyl)-1-methyl-5-((5-(2-methyl-2,7-diazaspiro[3.5]nonan-7-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

9-fluoro-2-(5-((5-(2-hydroxy-7-azaspiro[3.5]nonan-7-yl) pyridin-2-yl)amino)-3'-(hydroxymethyl)-1-methyl-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

9-fluoro-2-(3'-(hydroxymethyl)-1-methyl-5-((5-(4-methylpiperazin-1-yl) pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

9-fluoro-2-(3'-(hydroxymethyl)-1-methyl-5-((4-(4-(oxetan-3-yl)piperazin-1-yl)phenyl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

9-fluoro-2-(3'-(hydroxymethyl)-1-methyl-5-((6-(4-(oxetan-3-yl)piperazin-1-yl)pyridin-3-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-9-bromo-2-(3'-(hydroxymethyl)-1-methyl-5-((5-(2-methyl-4-(oxetan-3-yl)piperazin-1-yl)pyridin-3-yl) amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-1-oxo-1,3,4,6,7,8-hexahydro-2H-cyclopenta[4,5]pyrrolo[1,2-a]pyrazine-9-carbonitrile;

(S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-9-(trifluoromethyl)-3,4,7,8-hexahydro-2H-cyclopenta[4,5] pyrrolo[1,2-a]pyrazine-9-1(6H)-one;

(S)-9-ethoxy-2-(3'-(hydroxymethyl)-1-methyl-5-((5-(2-methyl-4-(oxetan-3-yl)piperazin-1-yl)pyridin-2-yl) amino)-6-oxo-1,6-dihydro-[3,4'-bipyridyl]-2'-yl)-7,7-dimethyl-3,4,7,8-tetrahydro-2H-cyclopenta[4,5]pyrrolo[1,2-a]pyrazin-1(6H)-one;

(S)-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-9-methoxy-7,7-dimethyl-3,4,7,8-tetrahydro-2H-cyclopenta[4,5]pyrrolo[1,2-a]pyrazin-1(6H)-one;

(S)-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-7,7-dimethyl-9-propoxy-3,4,7,8-tetrahydro-2H-cyclopenta[4,5]pyrrolo [1,2-a]pyrazin-1(6H)-one;

(S)-9-cyclopropoxy-2-(3'-(hydroxymethyl)-1-methyl-5-((5-(2-methyl-4-(oxetan-3-yl)piperazin-1-yl)pyridin-2-yl) amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one;

(S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-9-isopropoxy-7,7-dimethyl-3,4,7,8-tetrahydro-2H-cyclopenta[4,5]pyrrolo[1,2-a]pyrazin-1(6H)-one;

(S)-9-amino-2-(3'-(hydroxymethyl)-1-methyl-5-((5-(2-methyl-4-(oxetan-3-yl)piperazin-1-yl)pyridin-2-yl) amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one; and (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-9-methylamino-7,7-dimethyl-3,4,7,8-tetrahydro-2H-cyclopenta[4,5]pyrrolo [1,2-a]pyrazin-1(6H)-one.

The pharmaceutically acceptable salt in the present application refers to an inorganic alkaline salt, such as sodium salt, potassium salt, calcium salt, magnesium salt, zinc salt, ammonium salt, quaternary ammonium salt and aluminium salt; an organic alkaline salt, such as lysine salt, arginine salt, diethylamine salt, triethylamine salt, ethanolamine salt, trimethylamine salt, dicyclohexylamine salt, choline salt, dibenzylamine salt, and piperidine salt; and other pharmaceutically acceptable organic alkaline salts.

Where the compounds of the present application contains at least one salifiable nitrogen atom in its molecule, the compound can be converted to the corresponding salt by reaction with the corresponding organic or inorganic acid in an organic solvent such as acetonitrile or tetrahydrofuran. Typical organic acids are oxalic acid, tartaric acid, maleic acid, succinic acid, methanesulfonic acid, benzoic acid, benzenesulfonic acid, toluenesulfonic acid, sulfamic acid, citric acid, glutamic acid, pyroglutamic acid, aspartic acid, glucuronic acid, naphthalenesulfonic acid, glutaric acid, acetic acid, trifluoroacetic acid, malic acid, fumaric acid, salicylic acid, 4-aminosalicylic acid, lactic acid, palmic acid, stearic acid, lauric acid, cinnamic acid, alginic acid, ascorbic acid. Typical inorganic acids are nitric acid, hydrochloric acid, sulphuric acid and phosphoric acid.

One or more asymmetric carbon atoms in the compounds of the present application can be in the following forms: an optically pure enantiomer, a pure diastereoisomer, a mixture of enantiomers, a mixture of diastereoisomers, a mixture of racemic enantiomers, a racemate or a mixture of racemates. All possible isomers, stereoisomers of the compounds of formula (II) and mixtures thereof are also within the scope of the present application.

The present application also provides a pharmaceutical composition comprising at least one compound as defined above and optionally one or more pharmaceutically acceptable carriers and/or diluents.

The pharmaceutical composition provided in the present application may be prepared into any form, such as a granule, powder, tablet, coated tablet, capsule, pill, syrup, drop, solution, suspension and emulsion, or sustained-release formulation of the active ingredient, wherein examples of the capsule include hard or soft gelatin capsules, and the granule and powder may be in non-effervescent or effervescent form.

The pharmaceutical compositions of the present application may further comprise one or more pharmaceutically or physiologically acceptable carriers which will be properly formulated to facilitate administration. For example, the pharmaceutically or physiologically acceptable carrier can be saline, hot pressed water, Ringer's solution, buffered saline, glucose, maltodextrin, glycerol, ethanol or a mixture thereof. The pharmaceutical composition of the application may also comprise a pharmaceutically or physiologically acceptable additive, such as a diluent, lubricant, binder, glidant, disintegrant, sweetener, corrigent, wetting agent, dispersant, surfactant, solvent, coating agent, foaming agent, or aromatic agent.

Examples of the diluent that may be used include, but are not limited to, lactose, sucrose, starch, kaolin, salt, mannitol and dicalcium phosphate. Examples of the lubricant include, but are not limited to, talc, starch, stearates of magnesium or calcium, lycopodium and stearic acid. Examples of the binder include, but are not limited to, microcrystalline cellulose, tragacanth gum, glucose solution, mucilago acaciae, gelatin solution, sucrose, and starch paste. Examples of the glidant include, but are not limited to, colloidal silica. Examples of the disintegrant include, but are not limited to, cross-linked sodium carboxymethylcellulose, sodium starch hydroxyacetate, alginic acid, corn starch, potato starch, bentonite, methylcellulose, agar and carboxymethylcellulose. Examples of sweeteners include, but are not limited to, sucrose, lactose, mannitol and artificial sweeteners such as sodium cyclamate and saccharin, and any number of spray-dried corrigent. Examples of the corrigent include, but are not limited to, natural corrigents derived from plants, such as fruits, and compounds with good tastes, such as, but not limited to, mint and methyl salicylate. Examples of the wetting agent include, but are not limited to, propylene glycol monostearate, sorbitan monooleate, diglycol monolaurate and polyoxyethylene lauryl ether.

The pharmaceutical compositions of the present application can be administered according to conventional means through various routes, including oral, intravenous, intraarterial, intraperitoneal, intralumen, transdermal, nasal, inhalation, rectal, ocular and subcutaneous introduction.

The pharmaceutically acceptable carriers optionally added to the pharmaceutical composition of the present application are one or more of: water, alcohols, honey, mannitol, sorbitol, dextrin, lactose, caramel, gelatine, calcium sulphate, magnesium stearate, talc, kaolin, glycerol, tween, agar, calcium carbonate, calcium bicarbonate, surfactant, cyclodextrin and derivatives thereof, phospholipids, phosphates, starch and derivatives thereof, silicon derivatives, cellulose and derivatives thereof, pyrrolidones, polyethylene glycols, acrylic resins, phthalates, acrylic copolymers, and benzotrizoic acid esters.

The present application also provides use of the compound or the pharmaceutical composition as defined above in the manufacture of a medicament for preventing and/or treating Bruton's tyrosine kinase-mediated diseases.

The Bruton's tyrosine kinase-mediated disease comprises, but is not limited to autoimmune disorder, cancer or inflammatory disease.

The cancer mentioned above includes, but is not limited to, oesophageal cancer, lung cancer, rectal cancer, pancreatic cancer, thyroid cancer, lymphoma or leukaemia. The autoimmune disease or inflammatory disease mentioned above can be arthritis, systemic lupus erythematosus, inflammatory bowel disease, Crohn's disease, multiple sclerosis, asthma, thrombocytopenic purpura, chronic obstructive pulmonary disease, psoriasis, organ transplant rejection, allergic reactions or rhinitis.

DETAILED DESCRIPTION OF THE INVENTION

To illustrate the purposes, technical solutions and advantages of the present application, the present application will be further described in detail with the following accompanying drawings and examples. Obviously, the described examples are only a part of the examples of the present application, rather than all of the examples. All other examples obtained by a person of ordinary skill in the art based on the examples in the present application are within the protection scope of the present application.

The abbreviations used in the present application is summarized in Table 1.

TABLE 1

| No. | Abbreviation | Name |
|---|---|---|
| 1 | XPhos | 2-Dicyclohexylphosphine-2',4',6'-triisopropylbiphenyl |
| 2 | Xantphos | 4,5-Bis(diphenylphosphino)-9,9-dimethyloxanthene |
| 3 | BINAP | 1,1'-Binaphthyl-2,2'-bis(diphenylphosphine) |
| 4 | DME | Dimethyl ether |
| 5 | DMF | N,N-Dimethylformamide |
| 6 | DIPEA | N,N-Diisopropylethylamine |
| 7 | NMP | N-Methylpyrrolidone |
| 8 | NBS | N-Bromosuccinimide |
| 9 | DCM | Dichloromethane |
| 10 | TEA | Triethanolamine |
| 11 | LDA | Lithium diisopropylamine |
| 12 | TFA | Trifluoroacetic acid |
| 13 | TBAF | Tetrabutylammonium fluoride |

Example 1 (S)-9-fluoro-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bi-pyridin]-2'-yl)-7,7-dimethyl-3,4,7,8-tetrahydro-2H-cyclopenta[4,5]pyrrolo[1,2-a]pyrazin-1(6H)-one
1
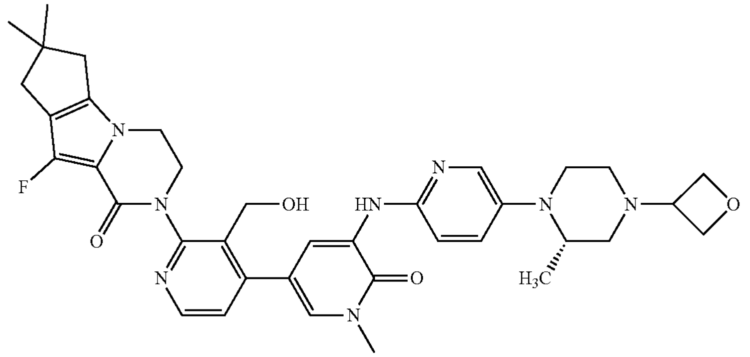
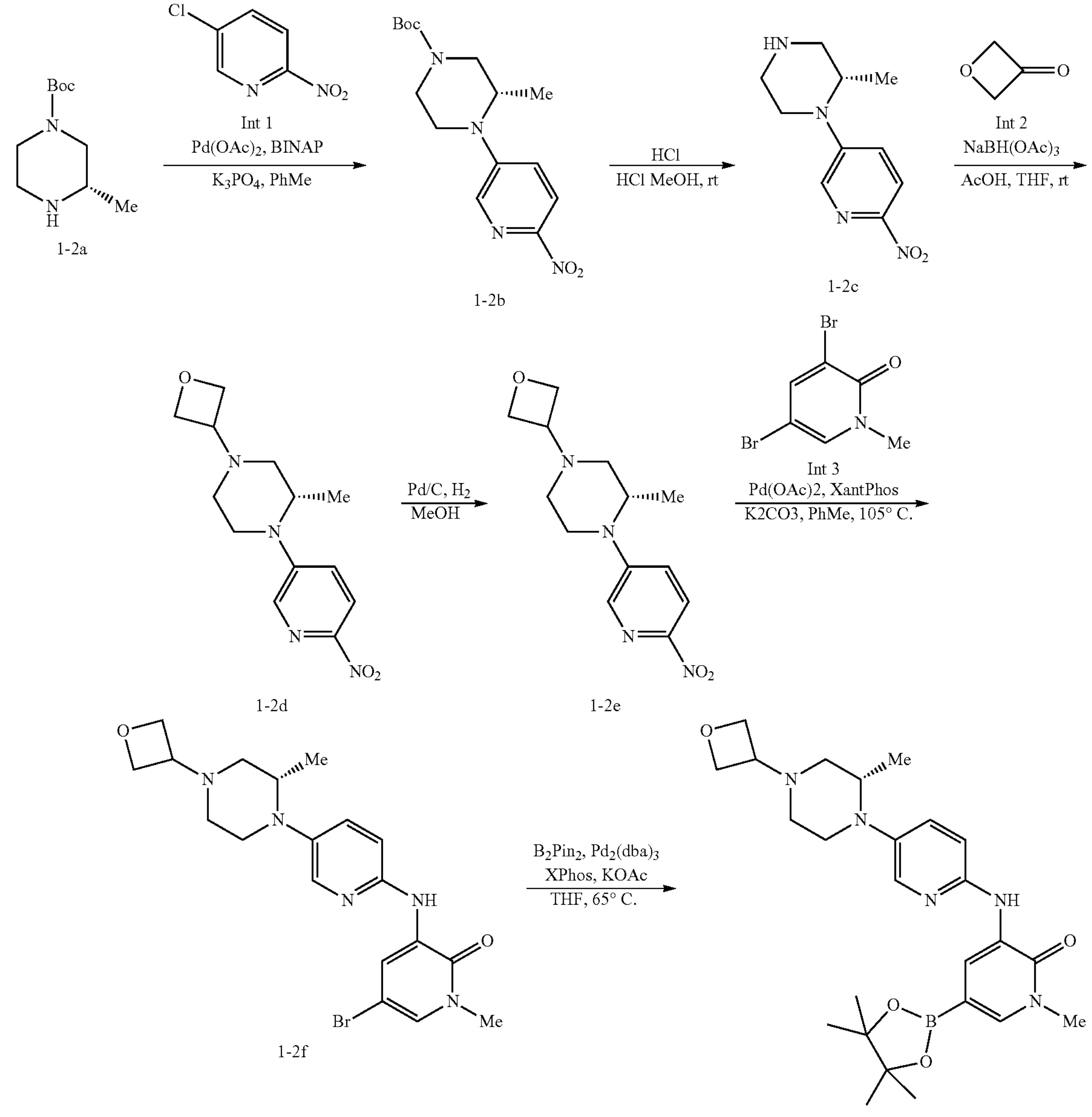
1f -continued
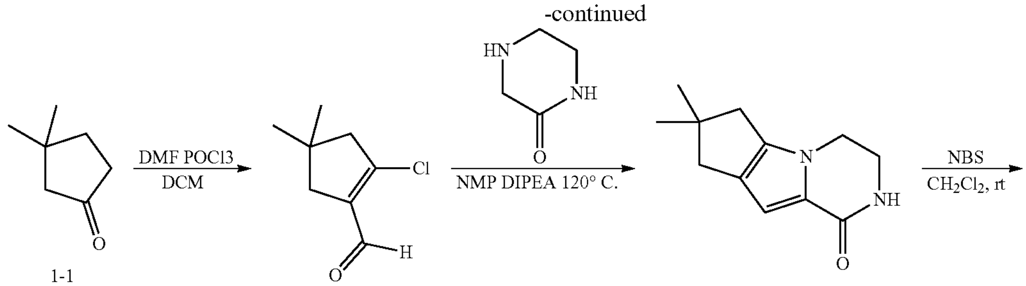
1-1 1-2 1a
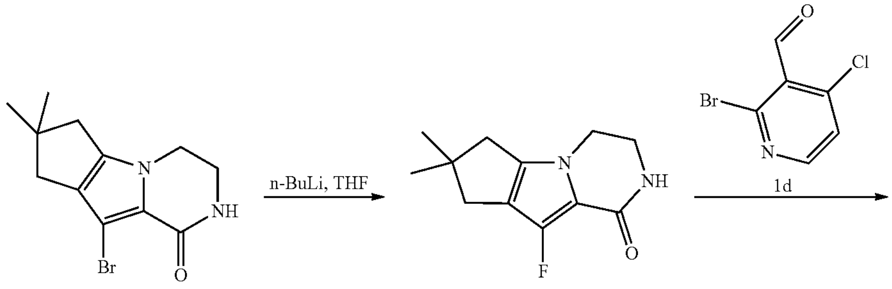
1b 1c
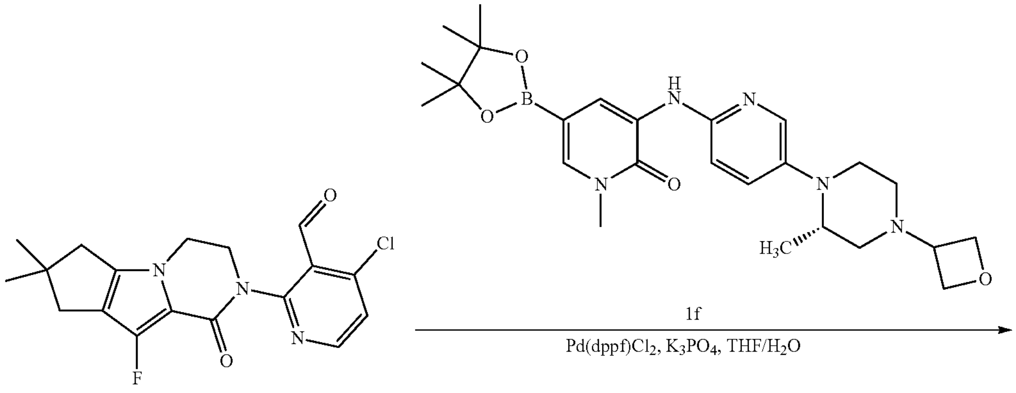
1e
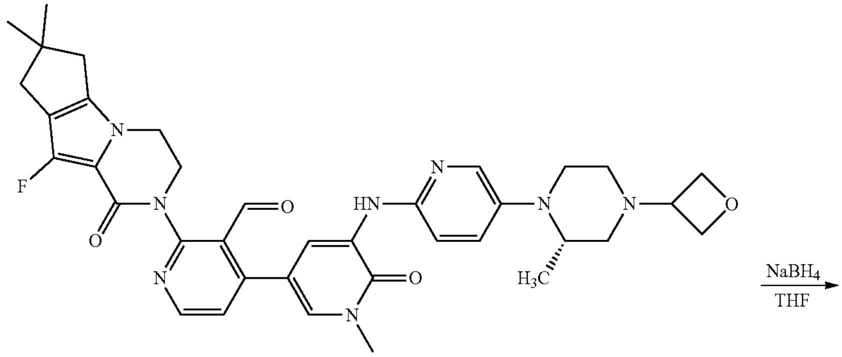
1g -continued

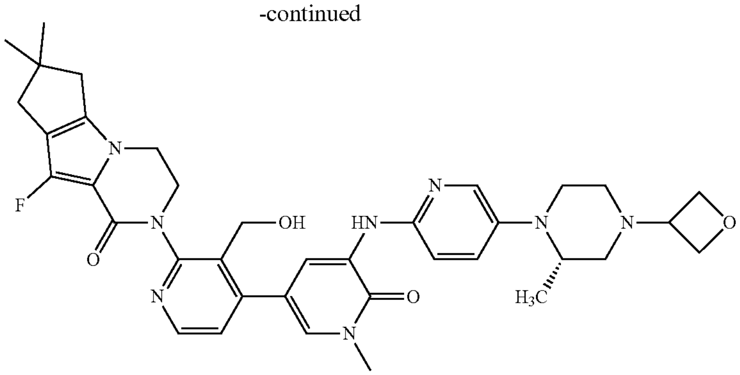

1

Step 1 tert-butyl (S)-3-methyl-4-(6-nitropyridin-3-yl)piperazine-1-carboxylate 1-2b Compound 1-2a (20 g, 100 mmol), Int-1 (24 g, 150 mmol) and potassium carbonate (50 g, 235 mmol) were dissolved in toluene (250 mL), and stirred thoroughly. Then, palladium acetate (0.68 g, 3 mmol) and BINAP (2.0 g, 3 mmol) were added. After that, the air in the reaction system was replaced three times with nitrogen, and the reaction was warmed to 90° C. and stirred for 3 h. The reaction was quenched by adding water, and extracted with dichloromethane. The organic phase was washed with water (100 mL) and saturated salt water (100 mL) in turn, dried over anhydrous sodium sulfate, filtered and concentrated. The resulting crude product was purified by column chromatography to obtain the title compound 1-2b (19.5 g, 58.7 mmol) with a yield of 58.7%.

MS m/z (ESI): 323.2 $[M+H]^+$.

Step 2 (S)-5-(2-methylpiperazin-1-yl)pyridin-2-amine 1-2c

Compound 1-2b (10.0 g, 32.2 mmol) was dissolved in a solution of hydrochloric acid in methanol (100 mL), then added with 20 mL of concentrated hydrochloric acid and stirred for 24 h. After that, a large amount of golden yellow solid was precipitated. The solid was collected by suction filtration, dissolved in dichloromethane and then dissociated in saturated potassium carbonate solution. After that, the reaction system was extracted with dichloromethane. The organic phase was washed with water (100 mL) and saturated salt water (100 mL) in turn, dried over anhydrous sodium sulfate, filtered and concentrated to obtain the title compound 1-2c (7.0 g, 31.5 mmol) with a yield of 98.0%.

MS m/z (ESI): 223.1 $[M+H]^+$.

Step 3 (S)-2-methyl-1-(6-nitropyridin-3-yl)-4-(oxiran-3-yl)piperazine 1-2d

Compound 1-2c (7.0 g, 31.5 mmol) was dissolved in THF (50 mL) and 2 mL of acetic acid was added followed by Int 2 (3.0 g, 41 mmol). The mixture was stirred at room temperature for 15 min, and then added with sodium borohydride acetate (10.0 g, 47.3 mmol) in batches. The reaction system was stirred at room temperature for 3 h, quenched with water and extracted with dichloromethane. The organic phase was washed with water (150 mL) and saturated salt water (150 mL) in turn, dried over anhydrous sodium sulfate, filtered and concentrated. The resulting crude product was purified by column chromatography (pure ethyl acetate) to obtain the title compound 1-2d (3.5 g, 12.5 mmol) with a yield of 40.0%.

MS m/z (ESI): 279.1 $[M+H]^+$.

Step 4 (S)-5-(2-methyl-4-(oxiran-3-yl)piperazin-1-yl)pyridin-2-amine 1-2e

Compound 1-2d (3.5 g, 12.5 mmol) was dissolved in methanol and stirred thoroughly. Then, palladium carbon (1.7 g, 16.0 mmol) was added. After that, the air in the reaction system was replaced three times with hydrogen balloons. The reaction was stirred at room temperature for about 12 h, and subjected to suction filtration. The filtrate was spin dried to obtain the crude product 1-2e (2.8 g, 11.3 mmol) with a yield of 70.5%. MS m/z (ESI): 249.1 $[M+H]^+$.

Step 5 (S)-5-bromo-1-methyl-3-((5-(2-methyl-4-(oxiran-3-yl)piperazin-1-yl)pyridin-2-yl)amino)pyridin-2(1H)-one 1-2f Compound 1-2e (2.8 g, 11.3 mmol) and Int 3 (3.2 g, 12.0 mmol) were dissolved in toluene (25 mL), and palladium acetate (0.27 g, 1.1 mmol), Xantphos (1.4 g, 2.2 mmol) and potassium carbonate (4.8 g, 34 mmol) were added under stirring conditions. The air in the reaction system was replaced three times with nitrogen. The reaction was performed at 105° C. for 3.0 h under reflux, cooled, quenched by adding saturated ammonium chloride solution, and extracted with dichloromethane. The organic phase was washed with water (100 mL) and saturated salt water (100 mL) in turn, dried over anhydrous sodium sulfate, filtered, concentrated, purified by column chromatography to obtain the title compound 1-2f (2.8 g, 6.5 mmol) with a yield of 57.1%.

MS m/z (ESI): 434.2 $[M+H]^+$.

Step 6 (S)-1-methyl-3-((5-(2-methyl-4-(oxiran-3-yl)piperazin-1-yl)pyridin-2-yl)amino)-5-(4,4,5,5-tetramethyl-1,3,2-dioxol-2-yl)pyridin-2(1H)-one 1f Compound 1-2f (2.8 g, 6.5 mmol) was dissolved in THF (25 mL), added with 2.5 g of pinacol borate ($B_2pin_2$) and stirred thoroughly, and then added with $Pd_2(dba)_3$ (0.19 g, 0.33 mmol), XPhos (0.62 g, 1.3 mmol) and potassium carbonate (4.8 g, 34 mmol). The air in the reaction system was replaced three times with nitrogen. The reaction was performed at 65° C. for 6.0 h, quenched by adding saturated ammonium chloride solution, and extracted with dichloromethane. The organic phase was washed with water (100 mL) and saturated salt water (100 mL) for several times, dried over anhydrous sodium sulfate, filtered, concentrated, purified by column chromatography (DCM:MeOH=98:2) to obtain the title compound 1f (1.4 g, 3.2 mmol) with a yield of 50%.

MS m/z (ESI): 560.4 $[M+H]^+$.

Step 7 2-chloro-4,4-dimethylcyclopent-1-ene-1-formaldehyde 1-2

In a 1 L reaction flask, compound 1-1 (20 g, 0.177 mmol) was dissolved in dichloromethane (350 ml), to which DMF (32.5 g, 0.44 mol) was added under ice bath, and then $POCl_3$ (57.0 g, 0.375 mol, 2.1 eq) was slowly added dropwise to the above reaction system. After the reaction solution has been slowly warmed to 30° C. and stirred at room temperature for 30 min, 3,3-dimethylcyclopentanone (20 g, 0.178 mol) was slowly added dropwise to the above reaction solution. The reaction solution was gradually warmed and reacted under reflux for 5 h, cooled to room temperature, then quenched by adding $K_3PO_4$ (10% w aq, 300 ml) dropwise to the reaction solution under ice bath with stirring, and left standing. The aqueous phase was reverse extracted with dichloromethane (200 ml). The organic phase was combined and spin dried to obtain 30 g crude product, which was used directly in the next step.

Step 8 7,7-dimethyl-3,4,7,8-tetrahydro-2H-cyclopenta[4,5]pyrrolo [1,2-a]pyrazin-1(6H)-one 1a The crude product 1-2 obtained in the previous step and 2-piperazinone (18.5 g, 0.19 mol), NMP (300 ml) and DIPEA (46 g, 0.36 mol) were added to the reaction flask in turn, warmed to 120° C., and reacted for 5 h under nitrogen protection. The reaction completion was confirmed by LCMS. The reaction solution was cooled, and quenched by adding water (1000 ml). A large amount of solid was precipitated, and filtered, which was then slurried with petroleum ether:ethyl acetate (5:1, 200 ml), filtered and dried to obtain product 1-3.

1H NMR (400 MHz, $CDCl_3$) δ 6.73-6.67 (m, 1H), 5.97 (s, 1H), 4.01-3.88 (m, 2H), 3.70-3.60 (m, 2H), 2.51-2.49 (m, 2H), 2.47 (q, J=0.7 Hz, 2H), 1.23 (s, 6H).

MS m/z (ESI): 205 $(M+1)^+$

Step 9 9-bromo-7,7-dimethyl-3,4,7,8-tetrahydro-2H-cyclopenta[4,5]pyrrolo [1,2-a]pyrazin-1(6H)-one 1b Compound 1a (1 g, 4.9 mmol) was dissolved in dichloromethane (30 mL) and cooled to −20° C. NBS (1.05 g, 5.88 mmol) was added to the solution and the reaction solution was warmed to room temperature and stirred overnight. After the reaction was complete, the reaction solution was diluted with dichloromethane (50 mL) and washed with saturated aqueous $Na_2S_2O_3$ solution. The organic phase was dried over anhydrous sodium sulfate, filtered and spin dried to obtain the crude product, which was purified by silica gel column chromatography to obtain compound 1b (960 mg) with a yield of 69%.

Step 10 9-fluoro-7,7-dimethyl-3,4,7,8-tetrahydro-2H-cyclopenta[4,5]pyrrolo [1,2-a]pyrazin-1(6H)-one 1c Compound 1b (560 mg, 2.0 mmol) was dissolved in tetrahydrofuran (15 mL) and then n-butyllithium (30 mL, 7.0 mmol) was added dropwise while stirring at −78° C. The resulting solution was stirred at −40° C. for 3 h and then cooled to −78° C., to which a solution of N-fluorobenzenesulfonimide (1.26 g, 4.0 mmol) in tetrahydrofuran (10 mL) was added dropwise. The resulting solution was stirred at room temperature for 3 h, quenched by adding water (15 mL) and extracted with ethyl acetate (50×2 mL). The combined organic phases were dried over anhydrous sodium sulphate, filtered and spin dried to obtain a crude product, which was purified by silica gel column chromatography to obtain compound 1c (310 mg) with a yield of 70%.

Step 11 4-chloro-2-(9-fluoro-7,7-dimethyl-1-oxo-1,3,4,6,7,8-hexahydro-2H-cyclopenta[4,5]pyrrolo[1,2-a]pyrazin-2-yl)nicotinaldehyde 1e Compound 1c (250 mg, 1.12 mmol), compound 1d (246.4 mg, 1.12 mmol), $Pd_2(dba)_3$ (211 mg, 0.23 mmol), XantPhos (266 mg, 0.46 mmol) and potassium carbonate (309 mg, 2.24 mmol) were suspended in tetrahydrofuran (15 mL). The air in the reaction system was replaced twice with nitrogen. After that, the reaction solution was heated to 65° C. and stirred for 2 h. After the reaction was complete, the reaction solution was spin dried and the resulted residue was purified by silica gel column chromatography to obtain compound 1e (170 mg) with a yield of 42%.

Step 12 (S)-2'-(9-fluoro-7,7-dimethyl-1-oxo-1,3,4,6,7,8-hexahydro-2H-cyclopenta[4,5]pyrrolo[1,2-a]pyrazin-2-yl)-1-methyl-5-((5-(2-methyl-4-(oxetan-3-yl)piperazin-1-yl)pyridin-2-yl)amino)-6-oxo-1,6-dihydro-[3,4'-bipyridyl]-3'-formaldehyde 1g Compound 1e (130 mg, 0.36 mmol), compound 1f (173 mg, 0.36 mmol), $Pd(dppf)Cl_2$ (26.3 mg, 0.036 mmol) and potassium phosphate (114.5 mg, 0.54 mmol) were dissolved in a mixed solution of tetrahydrofuran (16 mL) and water (4 mL). The air in the reaction system was replaced twice with nitrogen. After that, the reaction solution was heated to 65° C. and stirred for 3 h. After the reaction was complete, the solution was spin dried, diluted with water (30 mL) and extracted with dichloromethane (30×2 mL). The combined organic phases were dried with anhydrous sodium sulfate, filtered and spin dried to obtain a crude product, which was purified by silica gel column chromatography to obtain compound 1g (40 mg) with a yield of 16%.

Step 13 (S)-9-fluoro-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one Compound 1 g (40 mg, 0.06 mmol) was dissolved in a mixed solution of tetrahydrofuran (10 mL) and water (3 mL), added with $K_2HPO_4$ (10.4 mg, 0.06 mmol) and NaOH (2.4 mg, 0.06 mmol), followed by sodium borohydride (6.7 mg, 0.18 mmol). The reaction solution was stirred at room temperature for 2 h, diluted with water (20 mL) and extracted with dichloromethane (30×2 mL). The combined organic phases were dried over anhydrous sodium sulfate, filtered and spin dried to obtain a crude product, which was purified by silica gel column chromatography to obtain compound 1 (5 mg).

1H NMR (400 MHz, DMSO-d6) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz,

1H), 4.94 (t, J=5.1 Hz, 1H), 4.55 (td, J=6.5, 2.9 Hz, 2H), 4.49-4.39 (m, 4H), 4.25-4.12 (m, 3H), 3.82 (d, J=11.1 Hz, 1H), 3.67 (d, J=5.5 Hz, 1H), 3.60 (s, 3H), 3.40 (q, J=6.2 Hz, 1H), 3.13-3.06 (m, 1H), 2.94 (t, J=8.9 Hz, 1H), 2.58-2.53 (m, 3H), 2.45 (s, 2H), 2.36-2.28 (m, 2H), 2.19 (t, J=9.1 Hz, 1H), 1.22 (s, 6H), 0.93 (d, J=6.3 Hz, 3H). MS m/z (ESI): 683[M+H]$^+$.

Example 2 (S)-9-chloro-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

2

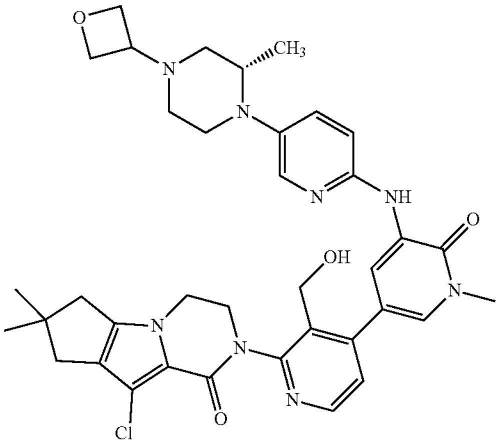

A synthetic method similar to that of Example 1 was used, in which N-bromosuccinimide was replaced by N-chlorosuccinimide to obtain 9-chloro-7,7-dimethyl-3,4,7,8-tetrahydro-2H-cyclopenta[4,5]pyrrolo[1,2-a]pyrazin-1(6H)-one intermediate, which was directly used in reactions similar to that of Example 1 after step 3 to obtain the title product 2 with a yield of 13%.

1H NMR (400 MHz, DMSO-d6) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.94 (t, J=5.1 Hz, 1H), 4.55 (td, J=6.5, 2.9 Hz, 2H), 4.49-4.39 (m, 4H), 4.25-4.12 (m, 3H), 3.82 (d, J=11.1 Hz, 1H), 3.67 (d, J=5.5 Hz, 1H), 3.60 (s, 3H), 3.40 (q, J=6.2 Hz, 1H), 3.13-3.06 (m, 1H), 2.94 (t, J=8.9 Hz, 1H), 2.58-2.53 (m, 3H), 2.42 (s, 2H), 2.38-2.29 (m, 2H), 2.19 (t, J=9.1 Hz, 1H), 1.21 (s, 6H), 0.93 (d, J=6.3 Hz, 3H). MS m/z (ESI): 699 (M+1)$^+$.

Example 3 (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7,9-trimethyl-3,4,7,8-tetrahydro-2H-cyclopenta[4,5]pyrrolo[1,2-a]pyrazin-1(6H)-one

3

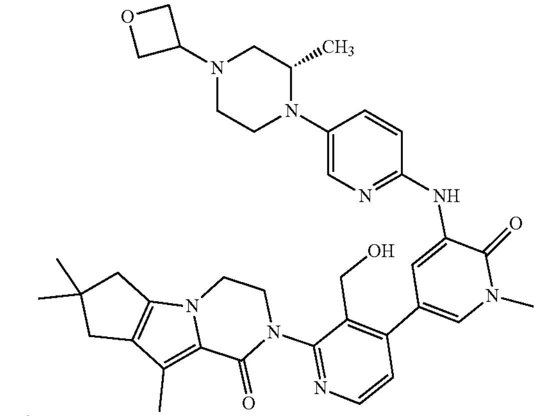

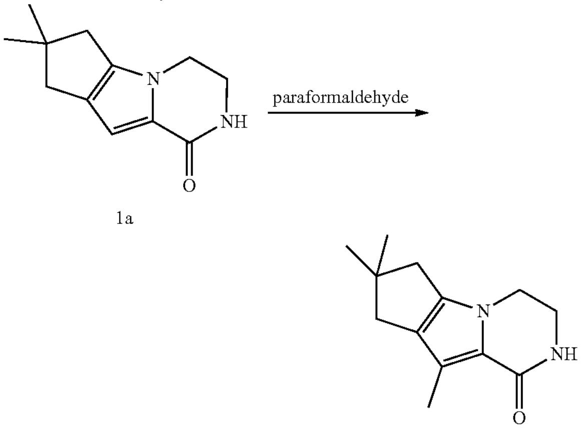

1a

3b

Step 1 7,7,9-trimethyl-3,4,7,8-tetrahydro-2H-cyclopenta[4,5]pyrrolo[1,2-a]pyrazin-1(6H)-one Compound 1a (0.5 g, 2.45 mmol) was dissolved in acetic acid (10 mL), and then added with hydroiodic acid (10 mL) and paraformaldehyde (0.5 g). The reaction solution was stirred under nitrogen protection at 25° C. for 3 h, and then added dropwise with hypophosphoric acid (50%, 0.8 mL) until the reaction solution was colourless. Saturated ammonium chloride was added under an ice bath. After that, the reaction solution was extracted with ethyl acetate (50×2 mL). The combined organic phases were dried over anhydrous sodium sulphate, filtered and spin dried to obtain a crude product, which was purified by silica gel column chromatography to obtain compound 3b (280 mg) with a yield of 52.4%.

MS m/z (ESI): 215 (M+1)$^+$

This step was followed by a similar reaction as in Example 1 after step 5 to produce the title product 3 with a yield of 19%.

1H NMR (400 MHz, DMSO-d6) δ 8.60 (d, J=2.4 Hz, 1H), 8.46-8.42 (m, 2H), 7.81 (d, J=2.8 Hz, 1H), 7.46 (d, J=2.4 Hz, 1H), 7.36-7.30 (m, 2H), 7.23-7.21 (m, 1H), 4.95 (t, J=5.2

Hz, 1H), 4.55-4.38 (m, 6H), 4.18-4.10 (m, 3H), 3.78-3.75 (m, 1H), 3.65 (s, 1H), 3.58 (s, 3H), 3.40-3.35 (m, 2H), 3.09-3.06 (m, 1H), 2.95-2.90 (m, 1H), 2.57-2.51 (m, 2H), 2.34-2.30 (m, 4H), 2.17 (s, 4H), 1.19 (s, 6H), 0.91 (d, J=6.4 Hz, 3H).
Example 4 (S)-2-(3'-(hydroxymethyl)-1-isopropyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one 4
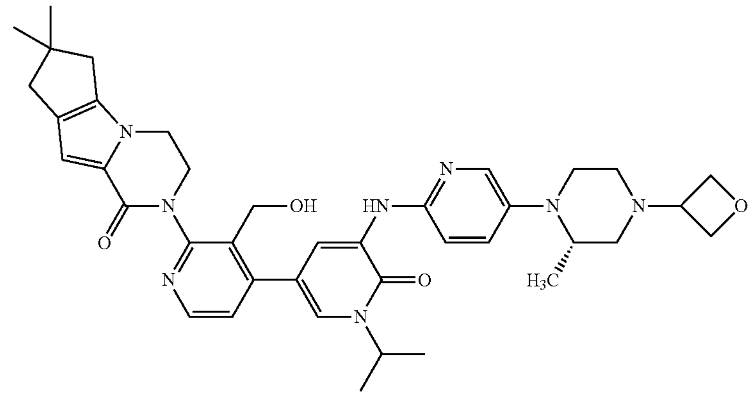
4
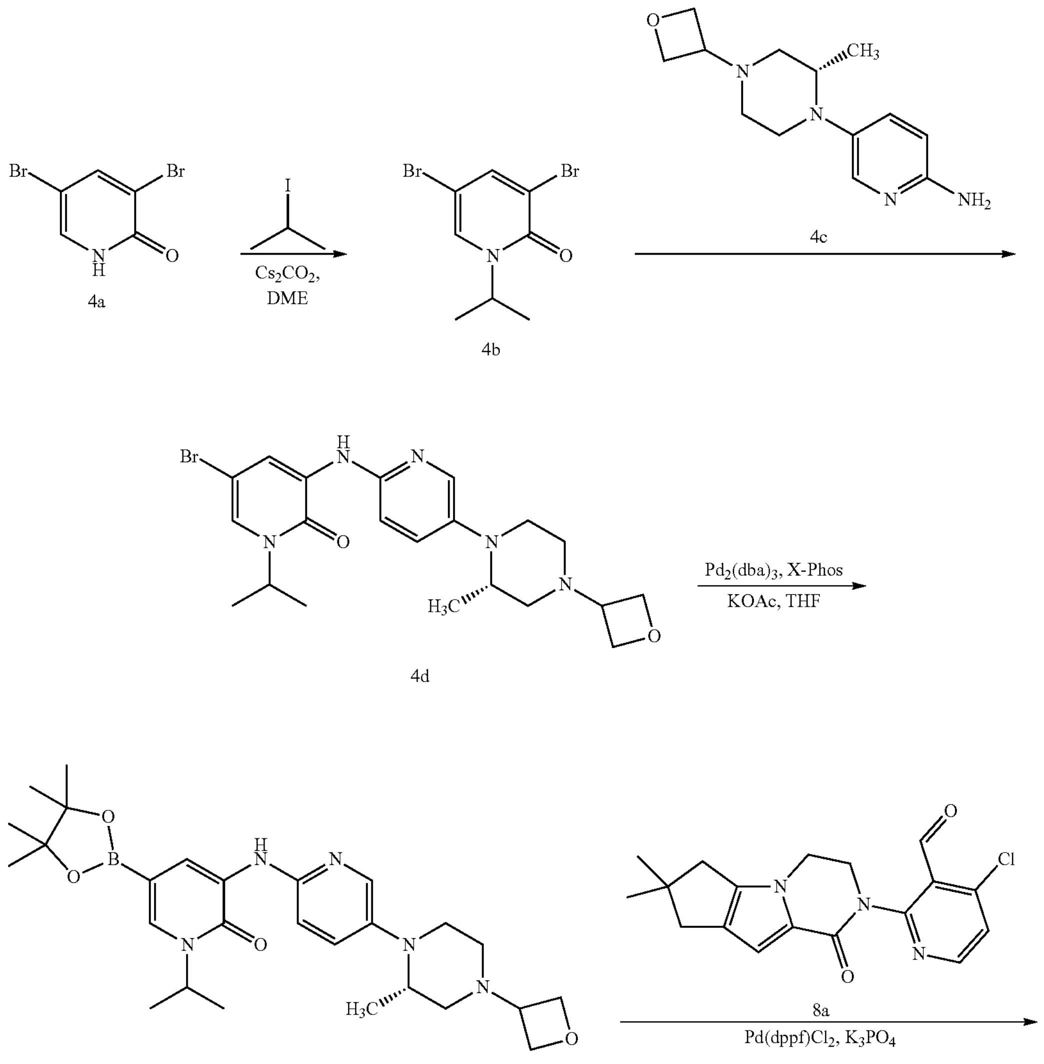
4a 4b 4c 4d 4e 8a -continued

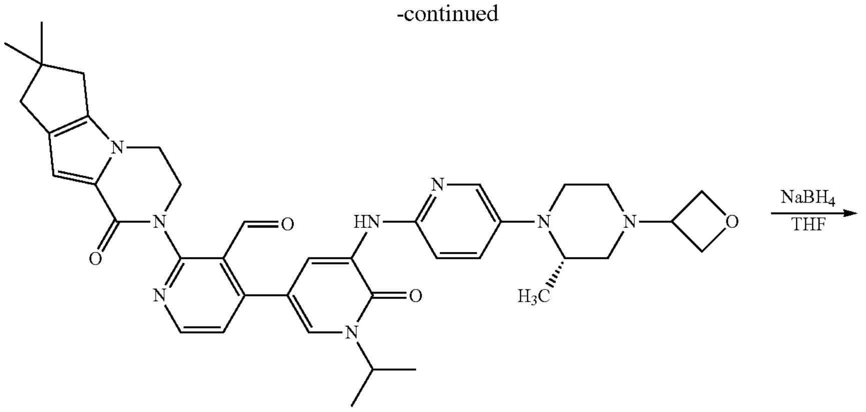

4f

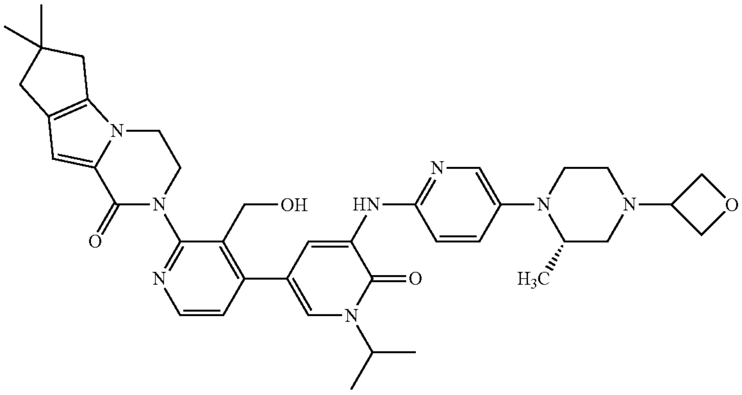

4

Step 1 3,5-dibromo-1-isopropylpyridin-2(1H)-one 4b

Compound 4a (2.52 g, 10 mmol) was dissolved in DME (30 mL), and added with 2-iodopropane (2.04 g, 1.2 mmol) and caesium carbonate (3.9 g, 1.2 mmol). The reaction solution was refluxed at 80° C. for 3 h. After cooling, the reaction solution was diluted with ethyl acetate (60 mL) and washed with aqueous $NaHCO_3$. The organic phase was dried with anhydrous sodium sulfate, filtered and spin dried to obtain the crude product, which was purified by silica gel column chromatography to obtain compound 4b (1.7 g) with a yield of 58%.

Step 2 (S)-5-bromo-1-isopropyl-3-((5-(2-methyl-4-(oxetan-3-yl)piperazin-1-yl)pyridin-2-yl)amino)pyridin-2(1H)-one 4d Compound 4b (1 g, 3.4 mmol), compound 4c (843 mg, 3.4 mmol), palladium acetate (152 mg, 0.68 mmol), Xantphos (786 mg, 1.36 mmol) and potassium carbonate (1.41 g, 10.2 mmol) were suspended in toluene (30 mL). The air in the reaction system was replaced twice with nitrogen. After that, the reaction solution was heated to 100° C. and stirred for 2 h. After the reaction was completed, the reaction solution was spin dried. The resulted residue was dissolved in dichloromethane (60 mL) and washed with saturated saline (30 mL). The organic phase was dried with anhydrous sodium sulfate, filtered and spin dried to obtain a crude product, which was purified by silica gel column chromatography to obtain compound 4d (670 mg) with a yield of 43%.

Step 3 (S)-1-isopropyl-3-((5-(2-methyl-4-(oxetan-3-yl)piperazin-1-yl)pyridin-2-yl)boranyl)-5-(4,4,5,5-tetramethyl-1,3,2-dioxaborolan-2-yl)pyridin-2(1H)-one 4e Compound 1d (560 mg, 1.2 mmol), diboron pinacol ester (309 mg, 1.2 mmol), $Pd_2(dba)_3$ (220 mg, 0.24 mmol), XPhos (228 mg, 0.48 mmol) and potassium acetate (235 mg, 2.4 mmol) were suspended in tetrahydrofuran (20 mL). The air in the reaction system was replaced twice with nitrogen. After that, the reaction solution was heated to 70° C. and stirred for 2 h. After the reaction was complete, the reaction solution was spin dried, and the resulted residue was purified by silica gel column chromatography to obtain compound 4e (500 mg) with a yield of 81%.

Step 4 (S)-2'-((7,7-dimethyl-1-oxo-1,3,4,6,7,8-hexahydro-2H-cyclopenta[4,5]pyrrolo[1,2-a]pyrazin-2-yl)-1-isopropyl-5-((5-(2-methyl-4-(oxetan-3-yl)piperazin-1-yl)pyridin-2-yl)amino-6-oxo-1,6-dihydro-[3,4'-bipyridyl]-3'-formaldehyde 4f Compound 4e (506 mg, 1 mmol), compound 8a (343 mg, 1 mmol), $Pd(dppf)Cl_2$ (73.1 mg, 0.1 mmol) and potassium phosphate (424 mg, 2.0 mmol) were dissolved in tetrahydrofuran (10 mL). The air in the reaction system was replaced twice with nitrogen. After that, the reaction solution was heated to 50° C. and stirred for 3 h. After the reaction was complete, the solution was spin dried, diluted with water (30 mL) and extracted with dichloromethane (50×2 mL). The combined organic phases were dried with anhydrous sodium sulfate, filtered and spin dried to obtain a crude product, which was purified by silica gel column chromatography to obtain compound 4g (350 mg) with a yield of 51%.

Step 5 (S)-2-(3'-(hydroxymethyl)-1-isopropyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one 4

Compound 4g (250 mg, 0.36 mmol) was dissolved in a mixed solution of tetrahydrofuran (15 mL) and water (3 mL), added with $K_2HPO_4$ (62.6 mg, 0.36 mmol) and NaOH (14.4 mg, 0.36 mmol), followed by sodium borohydride (38 mg, 1 mmol). The reaction solution was stirred at room temperature for 2 h, diluted with water (30 mL) and extracted with dichloromethane (30×2 mL). The combined organic phases were dried over anhydrous sodium sulfate, filtered and spin dried to obtain a crude product, which was purified by silica gel column chromatography to obtain compound 4 (80 mg) with a yield of 32%.

1H NMR (400 MHz, DMSO-d6) δ 8.59 (d, J=2.2 Hz, 1H), 8.52-8.40 (m, 2H), 7.81 (d, J=3.0 Hz, 1H), 7.61 (d, J=2.3 Hz, 1H), 7.40-7.29 (m, 2H), 7.21 (d, J=9.0 Hz, 1H), 6.53 (s, 1H), 5.21 (p, J=6.8 Hz, 1H), 5.07 (s, 1H), 4.52 (td, J=6.4, 2.9 Hz, 2H), 4.40 (dt, J=21.9, 5.9 Hz, 4H), 4.18 (t, J=8.7 Hz, 3H), 3.87-3.73 (m, 1H), 3.65 (s, 1H), 3.36 (q, J=6.3 Hz, 1H), 3.14-3.00 (m, 1H), 2.91 (t, J=10.3 Hz, 1H), 2.61-2.48 (m, 2H), 2.39 (s, 2H), 2.28 (d, J=3.9 Hz, 2H), 2.14 (t, J=9.2 Hz, 1H), 1.34 (d, J=6.8 Hz, 6H), 1.27-1.12 (m, 7H), 0.89 (d, J=6.3 Hz, 3H).

MS m/z (ESI): 693[M+H]$^+$.

Example 5 (S)-3-(7,7-dimethyl-1-oxo-1,3,4,6,7,8-hexahydro-2H-cyclopenta [4,5]pyrrolo[1,2-a] pyrazin-2-yl)-4-(hydroxymethyl)-5-(1-methyl-5-((5-(2-methyl-4-(oxetan-3-yl)piperazin-1-yl)pyridin-2-yl)amino)-6-oxo-1,6-dihydropyridin-3-yl) benzonitrile

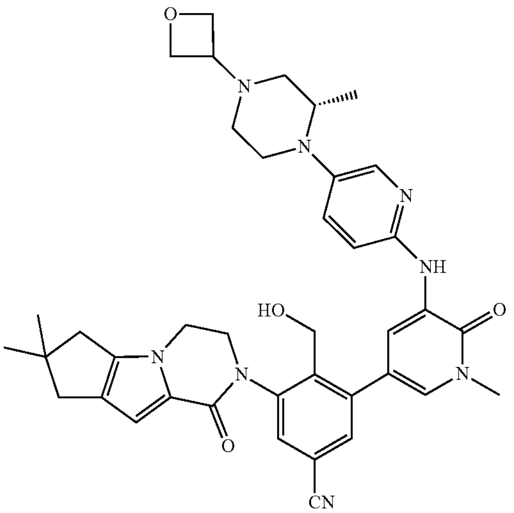

5

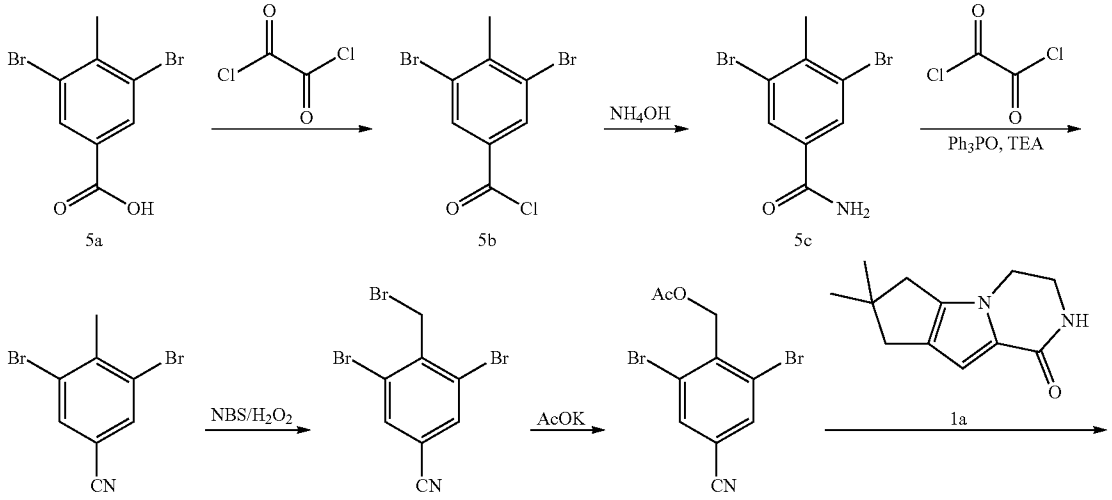

5a 5b 5c 5d 5e 5f

-continued

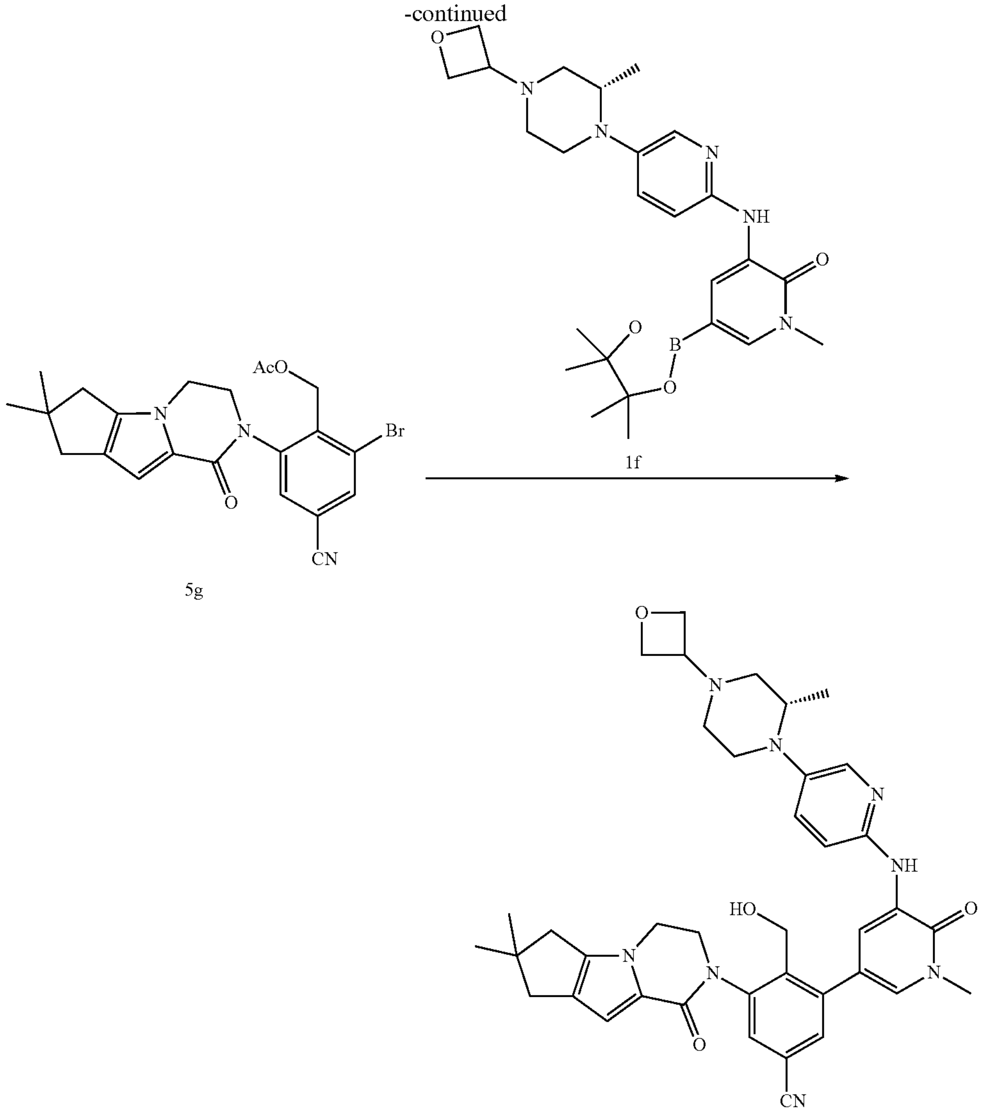

5g

1f

5

Step 1 3,5-dibromo-4-methylbenzoyl chloride 5b 3,5-Dibromo-4-methylbenzoic acid (5.0 g, 17.0 mmol, 1.0 eq) was dissolved in DCM (50 ml), added with oxalyl chloride (7.2 ml, 85.0 mmol, 5.0 eq) and DMF (2 drops) dropwise under cooling in an ice water bath, and reacted overnight at room temperature. The resultant was dried by evaporation under reduced pressure to obtain crude product 5b, which is used directly in the next reaction step.

Step 2 3,5-dibromo-4-methylbenzamide 5b

Compound 5b (5.3 g, 17.0 mmol, 1.0 eq) was dissolved in anhydrous THF (5 ml), added with 25% ammonium hydroxide solution and reacted at room temperature for 30 min. The resultant was extracted with ethyl acetate (50 ml). The organic layer was washed with saline and dried over anhydrous sodium sulfate in turn, and concentrated to dryness to obtain a white solid (4.9 g) 5c.

MS m/z (ESI): 293 $[M+1]^+$

Step 3 3,5-dibromo-4-methylbenzonitrile 5d

Compound 5c (4.6 g, 15.7 mmol), triphenylphosphine oxide (45 mg, 0.16 mmol) and TEA (6.5 ml, 47.1 mmol) were introduced into DCM (100 ml). Under cooling in an ice water bath, oxalyl chloride (2.7 ml, 31.4 mmol) was added. The reaction system was warmed to room temperature, reacted for 30 min, concentrated and purified by flash column to obtain a white solid (HHT0130-180-1A, 3.0 g).

MS m/z (ESI): 275 [M+1]+

Step 4 3,5-dibromo-4-(bromomethyl)benzonitrile 5e

Compound 5d (1.0 g, 3.6 mmol, 1.0 eq) was dissolved in DCM (30 ml) and water (6 ml). NBS (0.64 g, 3.6 mmol) and hydrogen peroxide (0.12 g, 3.6 mmol) were added sequentially. The reaction was refluxed for 4 h, and cooled to room temperature. The organic layer was separated, dried over anhydrous sodium sulphate, concentrated and purified by flash column to obtain a white solid (1.1 g).

MS m/z (ESI): 354 $[M+1]^+$

Step 5 2,6-dibromo-4-cyanobenzyl acetate 5f

Compound 5e (1.0 g, 2.8 mmol, 1.0 eq) was dissolved in DMF (10 ml), and added with potassium acetate (0.33 g, 3.4 mmol, 1.2 eq). The reaction was performed at 80° C. for 1 h, cooled to room temperature, diluted with ethyl acetate (50 ml), washed sequentially with water (20 ml) and saline (15 ml×3), dried over anhydrous sodium sulfate, concentrated and purified by flash column (PE to PA/EA=10:1) to obtain a white solid (HHT0130-158-1A, 590 mg).

MS m/z (ESI): 333 $[M+1]^+$

Step 6 2-bromo-4-cyano-6-(7,7-dimethyl-1-oxo-1,3,4,6,7,8-hexahydro-2H-cyclopenta[4,5]pyrrolo[1,2-a]pyrazin-2-yl)benzyl acetate 5g Compound 5f (540 mg, 1.6 mmol, 1.5 eq) and 7,7-dimethyl-3,4,7,8-tetrahydro-2H-cyclopenta[4,5]pyrrolo[1,2-a]pyrazin-1(6H)-one (7) (0.22 g, 1.1 mmol, 1.0 eq) were introduced into anhydrous 1,4-dioxane (30 ml), and sequentially added with cesium carbonate (0.72 g, 2.2 mmol, 2.0 eq), $Pd_2(dba)_3$ (0.10 g, 0.11 mmol, 0.1 eq) and Xantphos (0.13 g, 0.22 mmol, 0.2 eq). The reaction was refluxed for 8 h, dried by evaporation under reduced pressure, and added with ethyl acetate (50 ml). The resultant was washed sequentially with water (20 ml) and saline (20 ml), concentrated and purified by flash column to obtain a yellow solid (290 mg).

MS m/z (ESI): 457 $[M+1]^+$

Step 7 (S)-3-(7,7-dimethyl-1-oxo-1,3,4,6,7,8-hexahydro-2H-cyclopenta[4,5]pyrrolo[1,2-a]pyrazin-2-yl)-4-(hydroxymethyl)-5-(1-methyl-5-((5-(2-methyl-4-(oxetan-3-yl)piperazin-1-yl)pyridin-2-yl)amino)-6-oxo-1,6-dihydropyridin-3-yl) benzonitrile 5

Compound 5g (100 mg, 0.22 mmol, 1.0 eq) and (S)-1-methyl-3-((5-(2-methyl-4-(oxetan-3-yl)piperazin-1-yl)pyridin-2-yl)amino)-5-(4,4,5,5-tetramethyl-1,3,2-dioxaborolan-2-yl)pyridin-2(1H)-one (0.11 g. 0.22 mmol, 1.0 eq) were introduced into a mixture of n-butanol (20 ml) and water (4 ml), and sequentially added with potassium phosphate (93 mg, 0.44 mmol), $Pd_2(dba)_3$ (20 mg, 0.022 mmol) and XPhos (21 mg, 0.044 mmol). The reaction was refluxed for 8 h, dried by evaporation under reduced pressure, and added with ethyl acetate (50 ml). The resultant was washed sequentially with water (20 ml) and saturated saline (20 ml), concentrated and purified by flash column to obtain a near white solid (60 mg).

MS m/z (ESI): 689 $[M+1]^+$

1H NMR (400 MHz, DMSO-d6) δ 8.56 (t, J=2.5 Hz, 1H), 8.44 (s, 1H), 7.94 (d, J=1.7 Hz, 1H), 7.83 (d, J=2.9 Hz, 1H), 7.79 (d, J=1.7 Hz, 1H), 7.40-7.33 (m, 2H), 7.24 (d, J=9.0 Hz, 1H), 6.51 (s, 1H), 5.09 (q, J=4.2 Hz, 1H), 4.60-4.35 (m, 6H), 4.17 (dq, J=25.9, 7.8, 6.8 Hz, 3H), 3.92-3.81 (m, 1H), 3.67 (s, 1H), 3.58 (s, 3H), 3.39 (q, J=6.2 Hz, 1H), 3.09 (d, J=12.1 Hz, 1H), 2.93 (t, J=9.7 Hz, 1H), 2.56 (d, J=3.8 Hz, 2H), 2.41 (s, 2H), 2.32 (d, J=3.8 Hz, 2H), 2.19 (d, J=10.0 Hz, 1H), 1.21 (s, 6H), 0.92 (dd, J=6.4, 2.3 Hz, 3H).

Example 6 (S)-2-(7,7-dimethyl-1-oxo-1,3,4,6,7,8-hexahydro-2H-cyclopenta [4,5]pyrrolo[1,2-a]pyrazin-2-yl)-3-(hydroxymethyl)-4-(1-methyl-5-((5-(2-methyl-4-(oxetan-3-yl)piperazin-1-yl)pyridin-2-yl)amino)-6-oxo-1,6-dihydropyridin-3-yl) benzonitrile

6

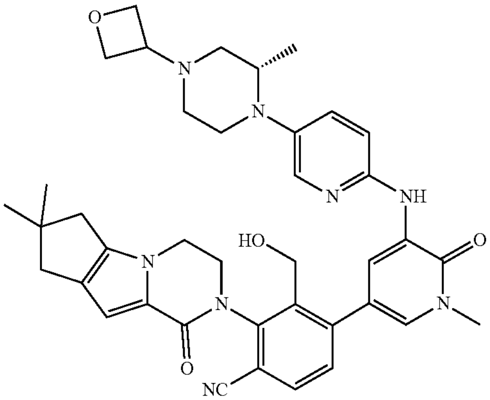

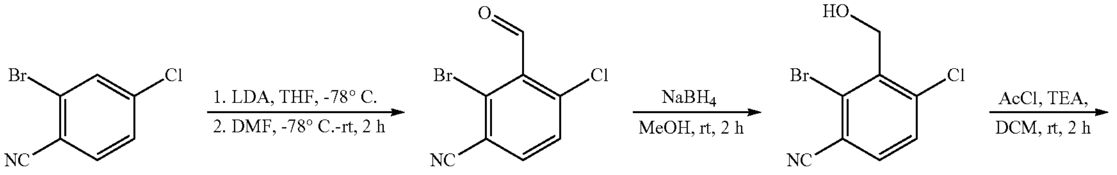

6a 6b 6c

-continued

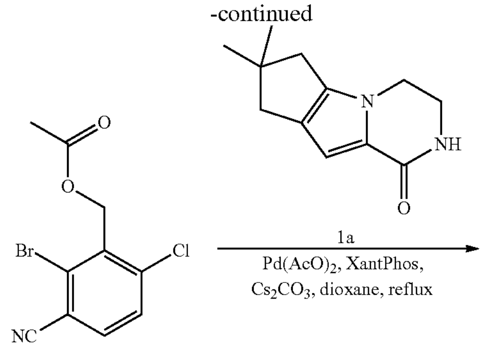

6d

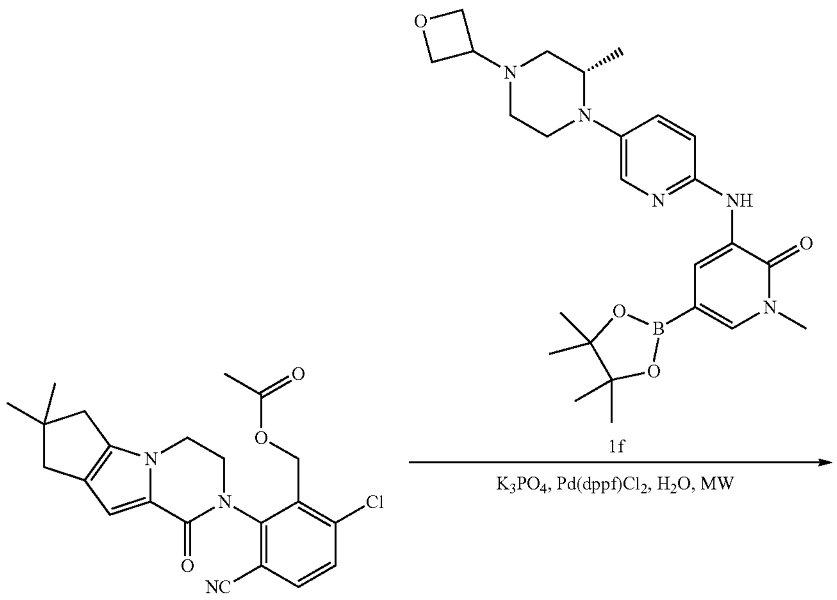

6e

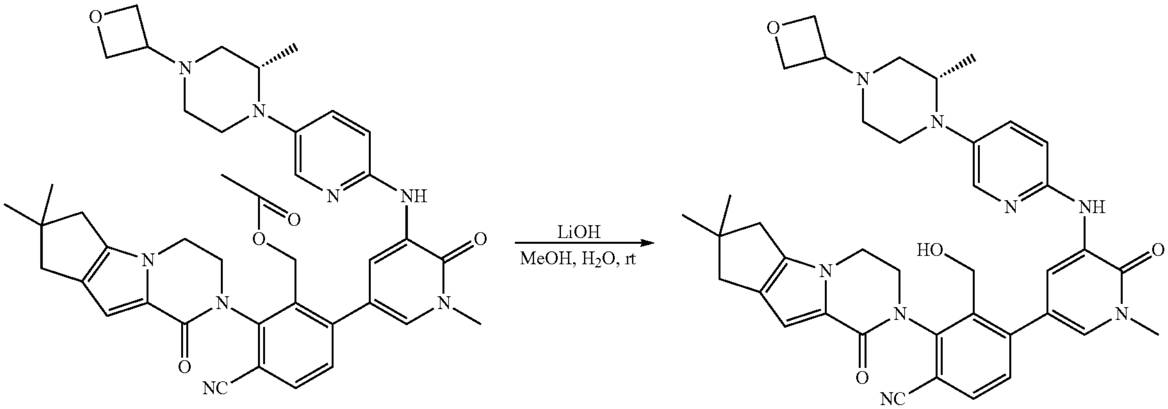

6f

6

Step 1 2-bromo-4-chloro-3-formylbenzonitrile 6b

Compound 6a (5.00 g, 23.1 mmol) was dissolved in THF (50 mL), added with LDA (15.0 mL, 30.1 mmol) dropwise at −78° C. and stirred for 0.5 h at −78° C. DMF (1.89 mL, 25.5 mmol) was added dropwise at −78° C. and stirred for 2 h at −78° C. The reaction completion was confirmed by LCMS. The reaction was quenched with saturated $NH_4Cl$ solution (50 mL) and extracted with EA (50 mL×3). The organic phases were combined, washed with saturated saltine (50 mL), dried over anhydrous $Na_2SO_4$, filtered and concentrated. The residue was subjected to column chromatography (PE/EA=100/1 to 1/100) to obtain a white solid compound 6b (0.60 g, yield 10%).

LCMS (ESI-MS) m/z: 245.9 $(M+H)^+$.

Step 2

2-bromo-4-chloro-3-(hydroxymethyl)benzonitrile 6c

Compound 6b (0.60 g, 2.46 mmol) was dissolved in anhydrous MeOH (10 mL). $NaBH_4$ (0.19 g, 4.92 mmol) was added at 0° C. The reaction system was brought back to room temperature and stirred for 2 h. The reaction completion was confirmed by LCMS. The reaction solution was quenched with water (20 mL) and extracted with EA (20 mL×3). The organic phases were combined, washed with saturated saltine (20 mL), dried over anhydrous $Na_2SO_4$, filtered and concentrated. The residue was subjected to column chromatography (PE/EA=100/1 to 1/100) to obtain a white solid compound 6c (0.50 g, yield 82%).

LCMS (ESI-MS) m/z: 247.9 $(M+H)^+$.

Step 3 2-bromo-6-chloro-3-cyanobenzyl acetate 6d

Compound 6c (0.50 g, 2.03 mmol) was dissolved in DCM (5 mL). TEA (0.53 mL, 4.06 mmol) and acetyl chloride (0.22 mL, 3.05 mmol) were added under an ice bath. The reaction was stirred for 2 h at room temperature. The reaction completion was confirmed by LCMS. The reaction solution was quenched with water (10 mL) and extracted with DCM (10 mL×3). The organic phases were combined, washed with saturated saltine (10 mL), dried over anhydrous $Na_2SO_4$, filtered and concentrated. The residue was subjected to column chromatography (PE/EA=100/1 to 1/100) to obtain a white solid compound 6d (0.45 g, yield 77%).

LCMS (ESI-MS) m/z: 287.9 $(M+H)^+$.

Step 4 6-chloro-3-cyano-2-(7,7-dimethyl-1-oxo-1,3,4,6,7,8-hexahydro-2H-cyclopenta[4,5]pyrrolo[1,2-a]pyrazin-2-yl)benzyl acetate 6e Compound 6d (0.45 g, 1.56 mmol) was dissolved in dioxane (5 mL), to which compound 5 (0.32 g, 1.56 mmol), $Pd(AcO)_2$ (35 mg, 0.16 mmol), Xantphos (90 mg, 0.16 mmol) and $Cs_2CO_3$ (1.02 g, 3.13 mmol) were added. The reaction was refluxed for 2 h under $N_2$ protection. The reaction completion was confirmed by LCMS. The reaction solution was added with water (10 mL) and extracted with EA (10 mL×3). The organic phases were combined, washed with saturated saltine (10 mL), dried over anhydrous $Na_2SO_4$, filtered and concentrated. The residue was subjected to column chromatography (PE/EA=100/1 to 1/100) to obtain a pale yellow solid compound 6e (0.21 g, yield 33%).

LCMS (ESI-MS) m/z: 412.2 $(M+H)^+$.

Step 5 (S)-3-cyano-2-(7,7-dimethyl-1-oxo-1,3,4,6,7,8-hexahydro-2H-cyclopenta[4,5]pyrrolo[1,2-a]pyrazin-2-yl)-6-(1-methyl-5-((5-(2-methyl-4-(oxa-3-yl)piperazin-1-yl)pyridin-2-yl)amino)-6-oxo-1,6-(dihydropyridin-3-yl)benzyl acetate 6f Compound 6e (0.16 g, 0.39 mmol) was dissolved in dioxane (3 mL), to which compound 7 (0.19 g, 0.39 mmol), $Pd(dppf)Cl_2$ (28 mg, 0.039 mmol) and $K_3PO_4$ (0.16 g, 0.78 mmol) were added. The reaction was performed with microwave for 2 h under $N_2$ protection. The reaction completion was confirmed by LCMS. The reaction solution was added with water (10 mL) and extracted with EA (10 mL×3). The organic phases were combined, washed with saturated saltine (10 mL), dried over anhydrous $Na_2SO_4$, filtered and concentrated. The residue was subjected to column chromatography (PE/EA=100/1 to 1/100) to obtain a brown compound 6f (80 mg, yield 28%).

LCMS (ESI-MS) m/z: 367.1 $(M+H)^+$.

Step 6 (S)-2-(7,7-dimethyl-1-oxo-1,3,4,6,7,8-hexahydro-2H-cyclopenta[4,5]pyrrolo[1,2-a]pyrazin-2-yl)-3-(hydroxymethyl)-4-(1-methyl-5-((5-(2-methyl-4-(oxetan-3-yl)piperazin-1-yl)pyridin-2-yl)amino)-6-oxo-1,6-dihydropyridin-3-yl) benzonitrile 5

Compound 6f (80 mg, 0.11 mmol) was dissolved in MeOH (2 mL) and an aqueous solution of NaOH (1 mL, 0.22 M) was added. The reaction was stirred for 2 h at room temperature. The reaction completion was confirmed by LCMS. The reaction solution was diluted with water (5 mL) and extracted with DCM (5 mL×3). The organic phases were combined, washed with saturated saltine (5 mL), dried over anhydrous $Na_2SO_4$, filtered and concentrated. The residue was subjected to a reversed phase column chromatography (H2O/MeCN=20/1 to 1/20) and a normal phase column chromatography (DCM/EA=100/1 to 1/100) to obtain a white solid compound 6 (10 mg, yield 13%).

LCMS (ESI-MS) m/z: 689.5 $(M+H)^+$.

1H NMR (400 MHz, $CDCl_3$) δ 8.59 (s, 1H), 7.95-7.86 (m, 2H), 7.77 (d, J=4.0 Hz, 1H), 7.56-7.52 (m, 2H), 6.85-6.81 (m, 2H), 4.72-4.47 (m, 5H), 4.39-4.34 (m, 1H), 4.17-3.96 (m, 3H), 3.70 (s, 2H), 3.67-3.29 (m, 4H), 3.12-3.07 (m, 2H), 2.60-2.03 (m, 7H), 1.30-1.25 (m, 9H), 0.96-0.86 (m, 3H).

Example 7 (S)-4-(7,7-dimethyl-1-oxo-1,3,4,6,7,8-hexahydro-2H-cyclopenta [4,5]pyrrolo[1,2-a]pyrazin-2-yl)-3-(hydroxymethyl)-2-(1-methyl-5-((5-(2-methyl-4-(oxetan-3-yl)piperazin-1-yl)pyridin-2-yl)amino)-6-oxo-1,6-dihydropyridin-3-yl) benzonitrile

7

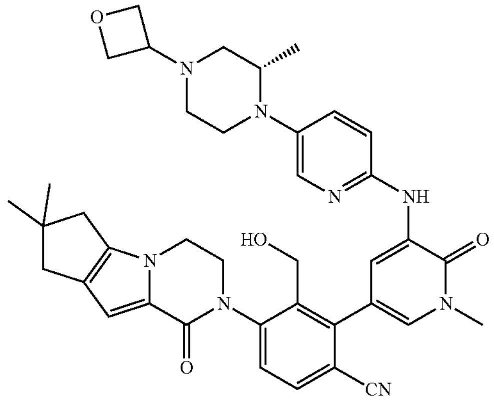

-continued

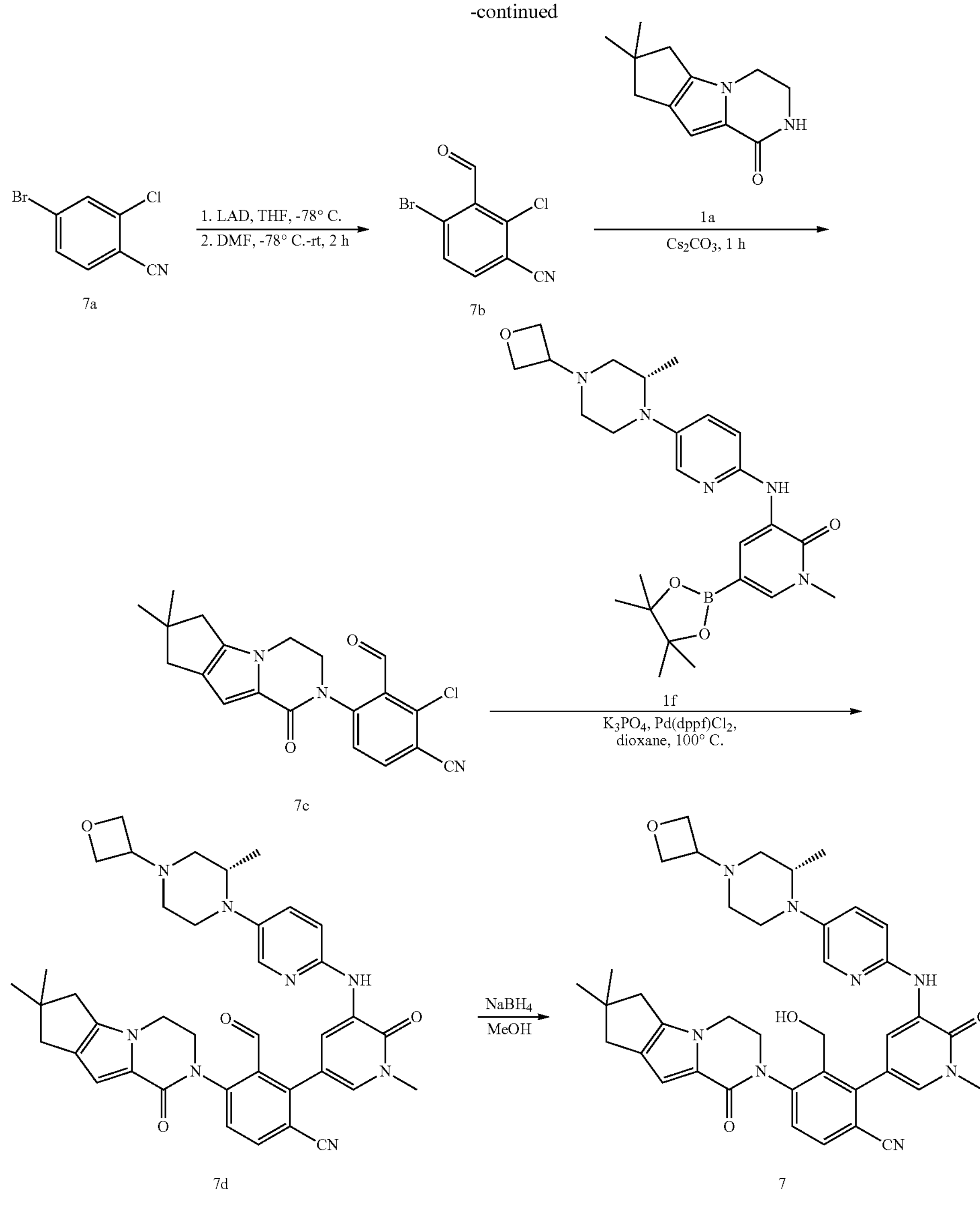

Step 1 4-bromo-2-chloro-3-formylbenzonitrile 7b

Compound 7a (4.00 g, 18.5 mmol) was dissolved in THF (50 mL), added with LDA (12.0 mL, 24.1 mmol) dropwise at −78° C. and stirred for 0.5 h at −78° C. DMF (1.51 mL, 20.4 mmol) was added dropwise at −78° C. and stirred for 2 h at −78° C. The reaction completion was confirmed by LCMS. The reaction was quenched with saturated $NH_4Cl$ solution (50 mL) and extracted with EA (50 mL×3). The organic phases were combined, washed with saturated saltine (50 mL), dried over anhydrous $Na_2SO_4$, filtered and concentrated. The residue was subjected to column chromatography (PE/EA=100/1 to 1/100) to obtain a white solid compound 2 (0.45 g, yield 10%).

LCMS (ESI-MS) m/z: 243.9 (M+H+).

Step 2 2-chloro-4-(7,7-dimethyl-1-oxo-1,3,4,6,7,8-hexahydro-2H-cyclopenta [4,5]pyrrolo[1,2-a] pyrazin-2-yl)-3-formylbenzonitrile 7c Compound 7b (0.45 g, 1.84 mmol) was dissolved in DMF (3 mL), to which compound 1a (0.32 g, 1.84 mmol), $Pd_2(dba)_3$ (0.17 g, 0.18 mmol), Xantphos (0.10 g, 0.18 mmol) and $Cs_2CO_3$ (1.20 g, 3.69 mmol) were added. The reaction was refluxed for 2 h under $N_2$ protection. The reaction completion was confirmed by LCMS. The reaction was quenched with water (10 mL) and extracted with EA (10 mL×3). The organic phases were combined, washed with saturated saltine (10 mL), dried over anhydrous $Na_2SO_4$, filtered and concentrated. The residue was subjected to column chromatography (PE/EA=100/1 to 1/100) to obtain a pale yellow solid compound 7c (0.14 g, yield 21%).

LCMS (ESI-MS) m/z: 368.2 $(M+H)^+$.

Step 3 (S)-4-(7,7-dimethyl-1-oxo-1,3,4,6,7,8-hexahydro-2H-cyclopenta [4,5]pyrrolo[1,2-a]pyrazin-2-yl)-3-(formyl)-2-(1-methyl-5-((5-(2-methyl-4-(oxetan-3-yl)piperazin-1-yl)pyridin-2-yl)amino)-6-oxo-1,6-dihydropyridin-3-yl)benzonitrile 7d Compound 7c (0.14 g, 0.38 mmol) was dissolved in dioxane (3 mL), to which compound 1f (0.18 g, 0.38 mmol), $Pd(dppf)Cl_2$ (27 mg, 0.038 mmol) and $K_3PO_4$ (0.16 g, 0.76 mmol) were added. The reaction was performed with microwave for 2 h under $N_2$ protection. The reaction completion was confirmed by LCMS. The reaction was quenched by adding water (10 mL) and extracted with EA (10 mL×3). The organic phases were combined, washed with saturated saltine (10 mL), dried over anhydrous $Na_2SO_4$, filtered and concentrated. The residue was subjected to column chromatography (PE/EA=100/1 to 1/100) to obtain a brown compound 7d (20 mg, yield 7%).

LCMS (ESI-MS) m/z: 687.5 $(M+H)^+$.

Step 4 (S)-4-(7,7-dimethyl-1-oxo-1,3,4,6,7,8-hexahydro-2H-cyclopenta [4,5]pyrrolo[1,2-a]pyrazin-2-yl)-3-(hydroxymethyl)-2-(1-methyl-5-((5-(2-methyl-4-(oxetan-3-yl)piperazin-1-yl)pyridin-2-yl)amino)-6-oxo-1,6-dihydropyridin-3-yl) benzonitrile 7

Compound 7d (20 mg, 0.029 mmol) was dissolved in MeOH (2 mL) to which $NaBH_4$ (2.2 mg, 0.058 mmol) was added. The reaction was stirred for 2 h at room temperature. The reaction completion was confirmed by LCMS. The reaction solution was quenched by adding water (5 mL) and extracted with DCM (5 mL×3). The organic phases were combined, washed with saturated saltine (5 mL), dried over anhydrous $Na_2SO_4$, filtered and concentrated. The residue was subjected to a reversed phase column chromatography (H2O/MeCN=20/1 to 1/20) and a normal phase column chromatography (DCM/EA=100/1 to 1/100) to obtain a white solid compound 7 (2 mg, yield 10%).

LCMS (ESI-MS) m/z: 689.5 $(M+H)^+$.

1H NMR (400 MHz, $CDCl_3$) δ 8.39 (s, 1H), 7.88-7.76 (m, 3H), 7.36-7.29 (m, 2H), 6.81 (s, 2H), 5.38-5.30 (m, 2H), 4.71 (s, 3H), 4.53-4.21 (m, 4H), 4.17-3.99 (m, 2H), 3.70-3.49 (m, 6H), 3.07 (s, 1H), 2.56-2.50 (m, 3H), 2.23-2.19 (m, 2H), 2.03-1.98 (m, 2H), 1.70-1.60 (m, 5H), 0.97-0.86 (m, 6H).

Example 8 2-(3-(hydroxymethyl)-4-(7-((5-(4-methylpiperazin-1-yl)pyridin-2-yl)amino)furo[3,2-b]pyridin-5-yl)pyridin-2-yl)-7,7-dimethyl-3,4,7,8-tetrahydro-2H-cyclopenta[4,5]pyrrolo[1,2-a]pyrazin-1 (6H)-one

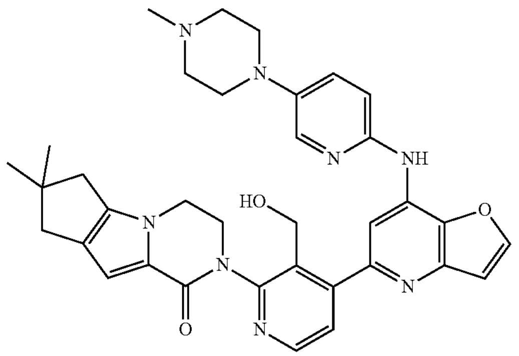

8

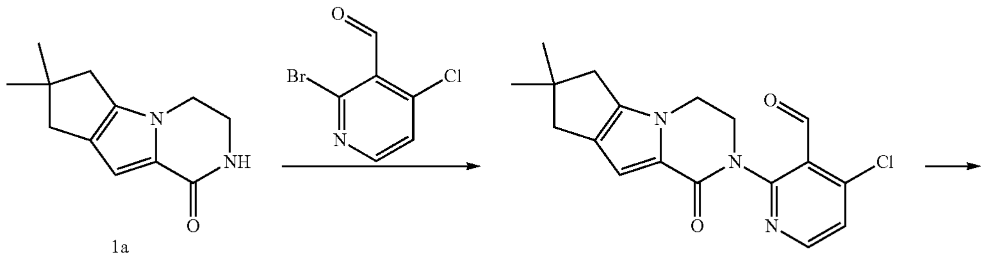

1a

8a

-continued
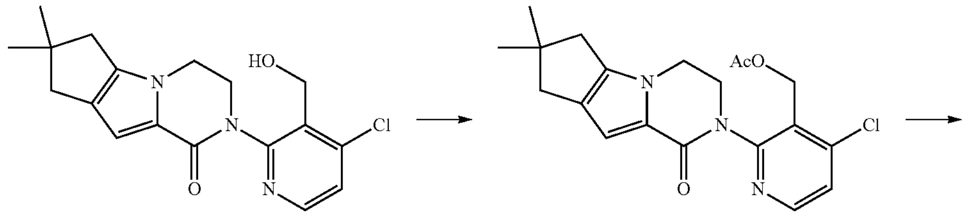
8b 8c
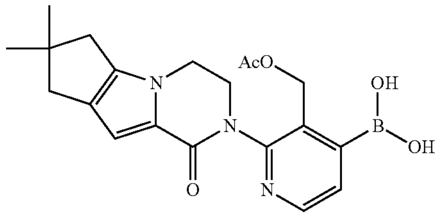
8d
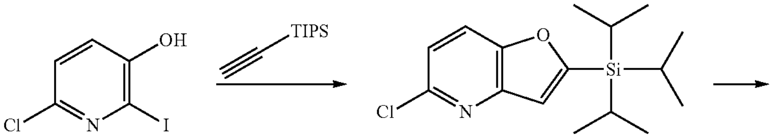
8e 8f
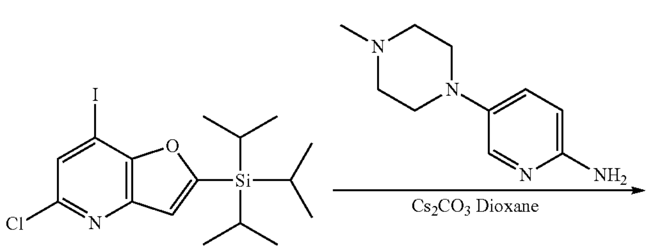
8g
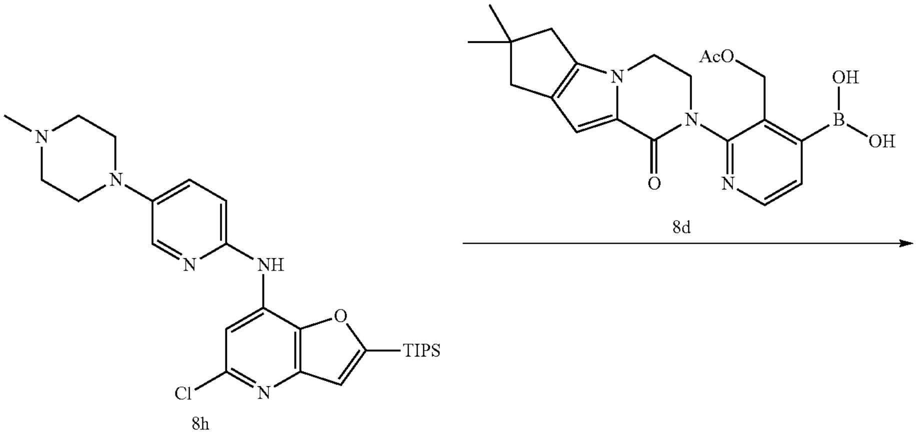
8h -continued

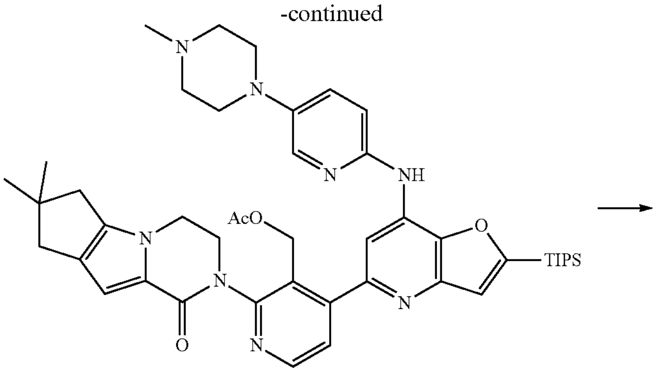

8i

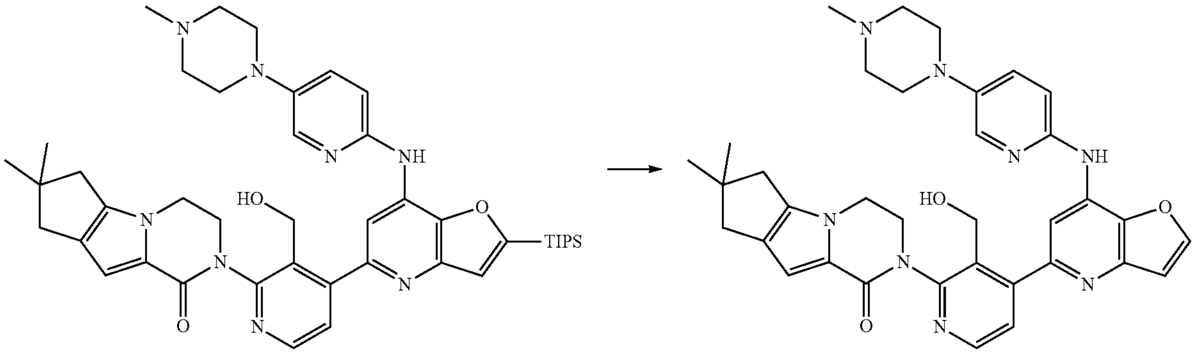

8j

8

Step 1 4-chloro-2-(7,7-dimethyl-1-oxo-1,3,4,6,7,8-hexahydro-2H-cyclopenta [4,5]pyrrolo[1,2-a] pyrazin-2-yl)nicotinaldehyde 8a Compound 1a (1.0 g, 4.9 mmol), 2-bromo-4-chloronicotinaldehyde (1.1 g, 4.9 mmol), palladium acetate (60 mg, 0.25 mmol), Xantphos (140 mg, 0.25 mmol), caesium carbonate (3.2 g, 10 mmol) and dioxane (20 ml) were added sequentially to a 100 ml reaction flask. The air in the reaction system was replaced 3 times with nitrogen. After that, the reaction solution was heated to 85° C., and reacted with stirring under nitrogen protection for 5 h. It was confirmed by LCMS detection that the raw materials were almost completely reacted. The reaction solution was cooled to room temperature and extracted with DCM/MeOH (10:1, 150 ml×2). The organic phase was dried, spin dried and separated on a column to obtain a pale yellow solid compound 2 (800 mg, yield: 47%).

LCMS (ESI-MS) m/z: 344.2 $(M+H)^+$.

1H NMR (400 MHz, DMSO-d6) δ 9.81 (s, 1H), 8.55 (d, J=5.4 Hz, 1H), 7.51 (d, J=5.4 Hz, 1H), 6.58 (s, 1H), 4.26-4.15 (m, 4H), 2.55 (s, 2H), 2.38 (s, 2H), 1.18 (s, 6H).

Step 2 2-(4-chloro-3-(hydroxymethyl)pyridin-2-yl)-7,7-dimethyl-3,4,7,8-tetrahydro-2H-cyclopenta[4,5] pyrrolo[1,2-a]pyrazine-1(6H)-one 8b Compound 8a (700 mg, 2.0 mmol) was dissolved in a mixture of dichloromethane (10 ml) and methanol (10 ml). Under ice bath conditions, sodium borohydride (160 mg, 4.0 mmol) was then added to the reaction system in batches. After the reaction was stirred for 2 h at room temperature, the reaction completion of the raw materials was confirmed by LCMS detection. The reaction was quenched by adding saturated ammonium chloride solution to the reaction solution. The organic phase was dried and spin dried to obtain a white solid compound 8b (700 mg, yield: 100%).

LCMS (ESI-MS) m/z: 346.2 $(M+H)^+$.

Step 3 methyl (4-chloro-2-(7,7-dimethyl-1-oxo-1,3,4,6,7,8-hexahydro-2H-cyclopenta[4,5]pyrrolo[1,2-a] pyrazin-2-yl)pyridin-3-yl)acetate 8c Compound 8b (550 mg, 1.6 mmol) was dissolved in dichloromethane (10 ml). Under ice bath condition, triethylamine (900 mg, 9 mmol) and acetic anhydride (1.6 g, 16 mmol, 10 eq) were added dropwise to the reaction system, which was kept at room temperature with stirring overnight. The reaction completion was confirmed by LCMS. Water and dichloromethane were added to the reaction solution. The organic phase was dried, spin dried, purified through a column to obtain a white solid compound 8c (600 mg, yield: 97%).

LCMS (ESI-MS) m/z: 388.2 $(M+H)^+$.

Step 4 (3-(acetoxymethyl)-2-(7,7-dimethyl-1-oxo-1,3,4,6,7,8-hexahydro-2H-cyclopenta[4,5]pyrrolo[1,2-a]pyrazin-2-yl)pyridin-4-yl)boronic acid 8d Compound 8c (370 mg, 1.0 mmol), $Pd(dppf)(OAc)_2$ (73 mg, 0.1 mmol), XPhos (47 mg, 0.1 mmol), potassium acetate (300 mg, 3.0 mmol), diboron (500 mg, 2.0 mmol) and dioxane were added sequentially to a reaction flask. The air in the reaction system was replaced 3 times with nitrogen. After that, the reaction system was heated to 70° C., and reacted for 4 h. It was confirmed by LCMS detection that the raw materials were almost completely reacted. After the reaction solution was cooled to room temperature, water and ethyl acetate were added to the reaction solution. The organic phase was dried and concentrated to dryness to obtain the crude product 8d (500 mg, purity: 80%), which was used directly in the next reaction step.

LCMS (ESI-MS) m/z: 398.3 $(M+H)^+$.

Step 5 5-chloro-2-(triisopropylsilyl)furano[3,2-b]pyridine 8f

Compound 8e (3.0 g, 11.7 mmol), triisopropylsilylacetylene (4.3 g, 24 mmol), cuprous iodide (200 mg, 1.1 mmol), $PdCl_2(PPh3)_2$ (700 mg, 1.0 mmol), dioxane (50 ml) and triethylamine (50 ml) were added sequentially to a reaction flask. The air in the reaction system was replaced 3 times with nitrogen. After that, the reaction solution was heated to 50° C. and reacted for 2 h. The reaction completion was confirmed by LCMS. After the reaction was cooled to room temperature, the reaction solution was diluted with water and ethyl acetate. The organic phase was dried and concentrated to dryness to obtain a pale green solid compound (3.6 g, yield: 100%).

LCMS (ESI-MS) m/z: 310.2 $(M+H)^+$.

1H NMR (400 MHz, Chloroform-d) δ 7.69 (dd, J=8.6, 1.0 Hz, 1H), 7.17 (d, J=8.6 Hz, 1H), 7.11 (d, J=0.9 Hz, 1H), 1.44-1.34 (m, 3H), 1.12 (d, J=7.4 Hz, 18H).

Step 6 5-chloro-7-iodo-2-(triisopropylsilyl)furano[3,2-b]pyridine 8 g

Compound 7 (3.1 g, 10 mmol) was dissolved in anhydrous tetrahydrofuran (20 ml), and cooled to a temperature of −65° C. N-butyllithium (13 mmol, 1.3 eq) was added dropwise to the reaction system and stirred for 1 h. Then, iodine (3.8 g, 15 mmol) dissolved in anhydrous tetrahydrofuran (10 ml) was added dropwise to the above reaction system. The reaction was stirred at low temperature for 2 h. The reaction completion was confirmed by LCMS. The reaction was quenched by adding saturated ammonium chloride solution and sodium sulphite solution to the reaction solution. Ethyl acetate and water were added. The mixture was stirred and left standing for further separating. The organic phase was dried and concentrated to dryness to obtain a yellow solid compound 8g (4.0 g, yield: 92%).

1H NMR (400 MHz, Chloroform-d) δ 7.59 (s, 1H), 7.19 (s, 1H), 1.40 (ddd, J=14.8, 8.1, 6.9 Hz, 3H), 1.14 (d, J=7.5 Hz, 18H).

Step 7 5-chloro-N-(5-(4-methylpiperazin-1-yl)pyridin-2-yl)-2-(triisopropylsilyl)furano[3,2-b]pyridin-7-amine 8h Compound 8g (560 mg, 1.2 mmol), 5-(4-methylpiperazin-1-yl)pyridin-2-amine (250 mg, 1.30 mmol) (Shanghai WuXi AppTec New Drug Development Co., Ltd.), palladium acetate (40 mg, 0.18 mmol), Xantphos (40 mg, 0.07 mmol), cesium carbonate (1.2 g, 3.6 mmol) and dioxane (15 ml) were added sequentially to the reaction system. The air in the reaction system was replaced 3 times with nitrogen. After that, the reaction was carried out at 85° C. for 4 h. It was confirmed by LCMS detection that the raw materials were almost completely reacted. The reaction solution was cooled, and diluted with water and ethyl acetate. The organic phase was dried and concentrated to dryness and separated on a column to obtain a yellow solid compound 8h (500 mg, yield: 78%).

LCMS (ESI-MS) m/z: 500.4 $(M+H)^+$.

1H NMR (400 MHz, Chloroform-d) δ 8.08 (d, J=2.9 Hz, 1H), 7.77 (s, 1H), 7.31 (dd, J=8.9, 3.0 Hz, 1H), 7.08 (s, 1H), 7.03 (dd, J=8.9, 0.7 Hz, 1H), 6.91 (s, 1H), 3.34 (s, 4H), 2.84 (s, 4H), 2.53 (s, 3H), 1.42-1.35 (m, 3H), 1.13 (d, J=7.4 Hz, 18H).

Step 8 methyl (2-(7,7-dimethyl-1-oxo-1,3,4,6,7,8-hexahydro-2H-cyclopenta[4,5]pyrrolo[1,2-a]pyrazin-2-yl)-4-(7-((5-(4-methylpiperazin-1-yl)pyridin-2-yl)amino)-2-(triisopropylsilyl)furano[3,2-b]pyridin-5-yl)pyridin-3-yl)acetate 8i Compound 8h (80 mg, 0.16 mmol), compound 8d (100 mg, crude product, 1.0 eq), $K_3PO_4$ (110 mg, 0.5 mmol), $Pd(dppf)Cl_2$ (12 mg, 0.016 mmol), DME (5 ml) and water (1.5 ml) were added sequentially to a reaction flask. The air in the reaction system was replaced 3 times with nitrogen. After that, the reaction system was heated to 80° C. and reacted for 4 hours. The reaction solution was cooled to room temperature, and diluted with water and ethyl acetate. The organic phase was dried and concentrated to dryness to obtain a crude product. An oily compound 8i (30 mg, purity: 80%) was obtained by preparation plate separation.

Step 9 2-(3-(hydroxymethyl)-4-(7-((5-(4-methylpiperazin-1-yl)pyridin-2-yl) amino)-2-(triisopropylmethylsilyl)furano[3,2-b]pyridin-5-yl)pyridinyl-2-yl)-7,7-dimethyl-3,4,7,8-tetrahydro-2H-cyclopenta[4,5]pyrrolo[1,2-a]pyrazine-1(6H)-one 8j Compound 8i (30 mg, purity of 80%) was dissolved in tetrahydrofuran (6 ml) and water (2 ml) and lithium hydroxide (24 mg, 1.0 mmol) was added to the reaction system, which was stirred at room temperature overnight. The reaction completion was confirmed by LCMS. Water and ethyl acetate were added to the reaction solution. The organic phase was dried and concentrated to dryness to obtain the crude product 8j, which was used directly in the next reaction step.

LCMS (ESI-MS) m/z: 775.6 (M+H)+.

Step 10 2-(3-(hydroxymethyl)-4-(7-((5-(4-methylpiperazin-1-yl)pyridin-2-yl) amino)furo[3,2-b]pyridin-5-yl)pyridin-2-yl)-7,7-dimethyl-3,4,7,8-tetrahydro-2H-cyclopenta[4,5]pyrrolo[1,2-a]pyrazin-1(6H)-one 8

Compound 8j (25 mg, 80% purity) was dissolved in tetrahydrofuran (5 ml) and TBAF (1.0 M, 0.2 ml) was added dropwise to the reaction system under ice bath conditions and the reaction was continued with stirring for 2 h. The reaction completion was confirmed by LCMS. Ethyl acetate and saturated ammonium chloride solution were added to the reaction solution. The organic phase was dried, concentrated to dryness and subjected to preparation plate separation to obtain a pale yellow solid compound 8 (10 mg, yield: 60%).

LCMS (ESI-MS) m/z: 619.4 $(M+H)^+$.

1H NMR (400 MHz, DMSO-d6) δ 11.00 (s, 1H), 8.61-8.51 (m, 2H), 8.11 (d, J=3.0 Hz, 1H), 7.59-7.55 (m, 1H), 7.51 (d, J=5.0 Hz, 1H), 7.37 (q, J=5.1, 4.7 Hz, 2H), 7.23 (d, J=5.1 Hz, 2H), 7.12 (d, J=5.8 Hz, 1H), 6.56 (s, 1H), 5.32 (t, J=4.9 Hz, 1H), 4.43 (d, J=8.8 Hz, 1H), 4.27 (d, J=12.3 Hz, 1H), 4.21 (t, J=5.8 Hz, 1H), 3.92 (d, J=12.0 Hz, 1H), 3.80 (s, 1H), 3.14 (d, J=8.5 Hz, 3H), 2.79 (d, J=4.1 Hz, 2H), 2.58 (d, J=8.0 Hz, 1H), 2.42 (s, 1H), 1.99 (dd, J=8.5, 6.5 Hz, 2H), 1.22 (s, 6H).

Example 9 2-(3-(hydroxymethyl)-4-(7-((5-(4-(oxetan-3-yl) piperazin-1-yl)pyridin-2-yl)amino)furo[3,2-b]pyridin-5-yl)pyridin-2-yl)-7,7-dimethyl-3,4,7,8-tetrahydro-2H-cyclopenta[4,5]pyrrolo[1,2-a]pyrazin-1(6H)-one
9
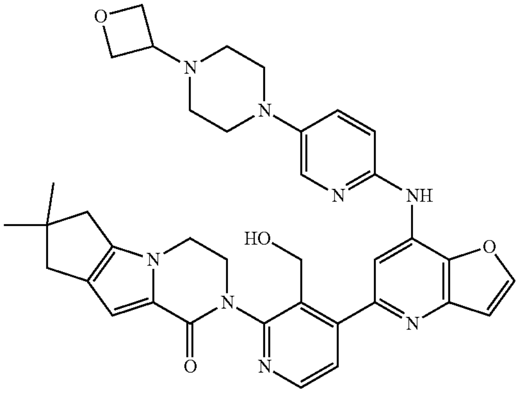
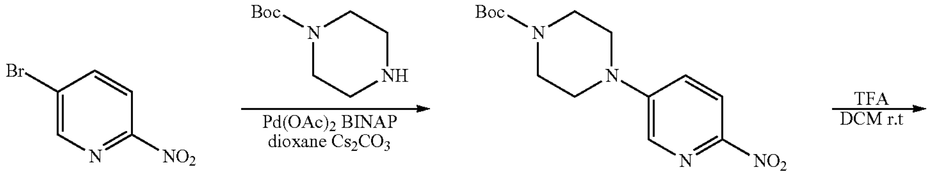
9a
9b
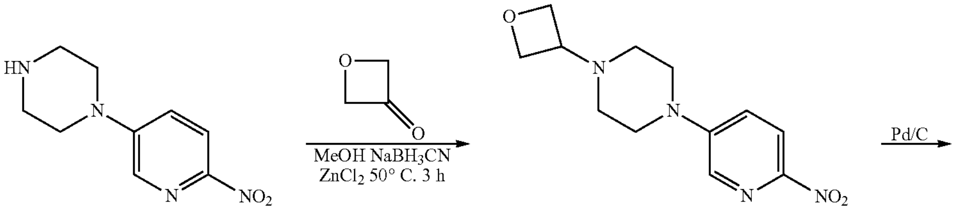
9c
9d
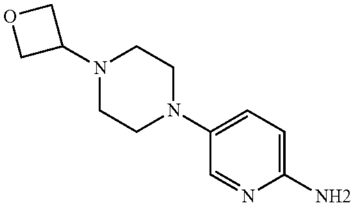
9e
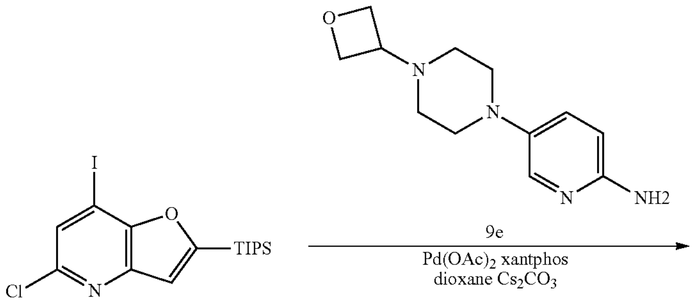
9f -continued
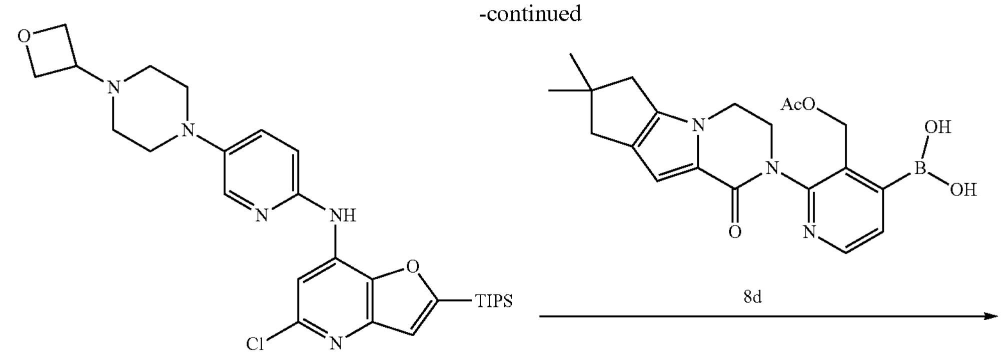
9f
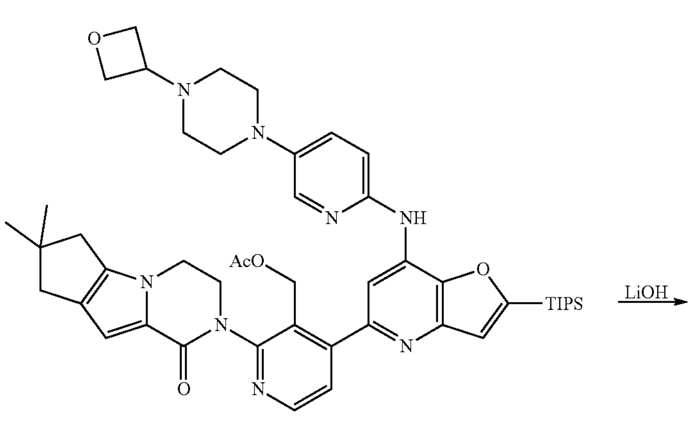
9h
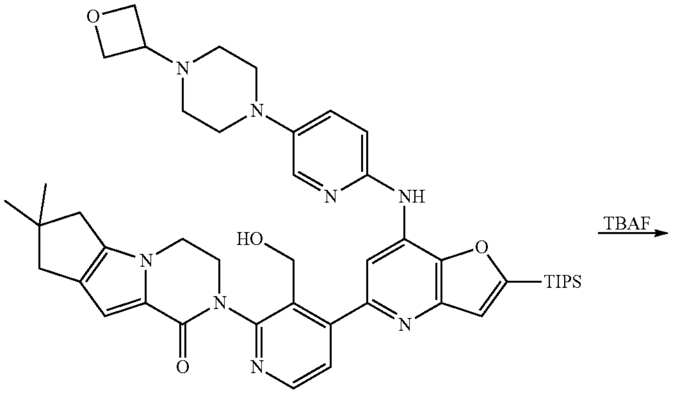
9i -continued

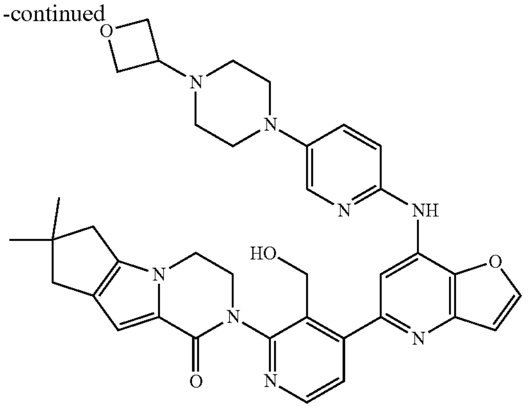

9

Step 1 tert-butyl 4-(6-nitropyridin-3-yl)piperazine-1-carboxylate 9b

Compound 9a (2.5 g, 12.3 mmol), tert-butyl piperazine-1-carboxylate (1.9 g, 10 mmol), palladium acetate (110 mg, 0.5 mmol), BINAP (310 mg, 0.5 mmol, 0.05 eq), $K_3PO_4$ (6.3 g, 30 mmol, 3.0 eq) and toluene (20 ml) were added sequentially to a 100 ml reaction flask. The air in the reaction system was replaced 3 times with nitrogen. After that, the reaction solution was heated to 95° C., and reacted with stirring under nitrogen protection for 5 h. It was confirmed by LCMS detection that the raw materials were almost completely reacted. The reaction solution was cooled to room temperature and extracted with DCM/MeOH (10:1, 150 ml×2). The organic phase was dried, spin dried and separated on a column to obtain the pale yellow solid compound 9b (1.8 g, yield: 58%).

1H NMR (400 MHz, DMSO-d6) δ 8.21 (d, J=3.0 Hz, 1H), 8.14 (d, J=9.2 Hz, 1H), 7.43 (dd, J=9.3, 3.1 Hz, 1H), 3.57-3.38 (m, 8H), 1.39 (s, 9H).

Step 2 1-(6-nitropyridin-3-yl)piperazine 9c

Compound 9b (1.0 g, 3.2 mmol) was dissolved in dichloromethane (10 ml) under ice bath conditions, and TFA (8 ml) was added dropwise to the reaction system. After the reaction was stirred for 2 h at room temperature, the complete reaction of the raw materials was confirmed by TLC detection. The reaction solution was directly spin dried to obtain the yellow oily compound 9c, which was used directly in the next reaction step.

Step 3 1-(6-nitropyridin-3-yl)-4-(oxetan-3-yl)piperazine 9d

Compound 9c (1.2 g, 10 mmol) was dissolved in methanol (20 ml) and 3-oxetanone (720 mg, 10 mmol), zinc chloride (870 mg, 6.4 mmol) and sodium cyanoborohydride (400 mg g, 6.4 mmol) were added to the reaction system at room temperature and stirred for 4 h at 50° C. The reaction completion was confirmed by LCMS. Water and dichloromethane were added to the reaction solution. The organic phase was dried, spin dried, purified through a column to obtain a yellow solid compound 9d (800 mg, yield: 94%).

1H NMR (400 MHz, Chloroform-d) δ 8.15 (d, J=9.1 Hz, 1H), 8.12 (d, J=3.0 Hz, 1H), 7.19 (dd, J=9.2, 3.0 Hz, 1H), 4.70 (t, J=6.5 Hz, 2H), 4.62 (t, J=6.1 Hz, 2H), 3.57-3.52 (m, 1H), 3.50-3.45 (m, 4H), 2.53-2.48 (m, 4H).

Step 4 5-(4-(oxetan-3-yl)piperazin-1-yl)pyridin-2-amine 9e

Compound 9d (800 mg, 3.0 mmol) was dissolved in methanol (20 ml). Palladium carbon (10% w, 100 mg) was added to the reaction system. The air in the reaction system was replaced 3 times with nitrogen. After that, the reaction was continued with stirring for 4 h. TLC showed that the raw materials were completely reacted. The reaction solution was filtered through diatomaceous earth and spin dried to obtain a white solid compound 9e (700 mg, yield: 98%)

LCMS (ESI-MS) m/z: 235.2 $(M+H)^+$.

Step 5 5-chloro-N-(5-(4-(oxetan-3-yl)piperazin-1-yl)pyridin-2-yl)-2-(triisopropylsilyl)furano[3,2-b]pyridin-7-amine 9g Compound 9e (800 mg, 1.8 mmol), compound 9f (420 mg, 1.8 mmol, 1.0 eq), palladium acetate (20 mg, 0.09 mmol), Xantphos (50 mg, 0.09 mmol), cesium carbonate (1.1 g, 3.6 mmol) and dioxane (20 ml) were added sequentially to a reaction flask. The air in the reaction system was replaced 3 times with nitrogen. After that, the reaction was heated to 85° C. and reacted for 4 h. LCMS showed that the raw materials were completely reacted. The reaction solution was cooled, and diluted with water and ethyl acetate. The organic phase was dried and concentrated to dryness and separated on a column to obtain a yellow solid compound 9g (800 mg, yield: 82%).

LCMS (ESI-MS) m/z: 542.4 $(M+H)^+$.

Step 6 methyl (2-(7,7-dimethyl-1-oxo-1,3,4,6,7,8-hexahydro-2H-cyclopenta[4,5]pyrrolo[1,2-a]pyrazin-2-yl)-4-(7-((5-(4-(oxetan-3-yl)piperazin-1-yl)pyridin-2-yl)amino)-2-(triisopropylsilyl)furano[3,2-b]pyridin-5-yl)pyridin-3-yl)acetate 9h Compound 9 g (150 mg, 0.28 mmol), (3-(acetoxymethyl)-2-(7,7-dimethyl-1-oxo-1,3,4,6,7,8-hexahydro-2H-cyclopenta[4,5]pyrrolo[1,2-a]pyrazin-2-yl)pyridin-4-yl)boronic acid (200 mg. purity: 87%), $Pd(dppf)Cl_2$ (20 mg, 0.028 mmol), $K_3PO_4$ (180 mg, 0.84 mmol), dioxane (6 ml) and water (2 ml) were added sequentially to a reaction flask. The air in the reaction system was replaced 3 times with nitrogen. After that, the reaction was heated to 80° C. and reacted for 4 h. The reaction solution was separated and purified by preparation plate separation to obtain compound 9h (20 mg, purity: 90%, yield: 10%).

LCMS (ESI-MS) m/z: 859.6 (M+H)+.

Step 7 2-(3-(hydroxymethyl)-4-(7-((5-(4-(oxetan-3-yl)piperazin-1-yl)pyridin-2-yl)amino)-2-(triisopropylsilyl)furano[3,2-b]pyridin-5-yl)pyridin-2-yl-7,7-dimethyl-3,4,7,8-tetrahydro-2H-cyclopenta[4,5]pyrrolo[1,2-a]pyrazine-1(6H)-one 9i Compound 9h (20 mg, purity: 90%) was dissolved in tetrahydrofuran (6 ml) and water (2 ml), and lithium hydroxide (24 mg, 1.0 mmol) was added to the reaction solution, which was reacted at room temperature overnight. The reaction completion was confirmed by TLC. The reaction solution was diluted with ethyl acetate and water. The organic phase was dried and then spin dried to obtain a crude product 9i, which was used directly in the next reaction step.

Step 8 2-(3-(hydroxymethyl)-4-(7-((5-(4-(oxetan-3-yl) piperazin-1-yl)pyridin-2-yl)amino)furo[3,2-b]pyridin-5-yl)pyridin-2-yl)-7,7-dimethyl-3,4,7,8-tetrahydro-2H-cyclopenta[4,5]pyrrolo[1,2-a]pyrazin-1(6H)-one 9

Compound 9i (20 mg, 90% purity) was dissolved in tetrahydrofuran (5 ml) and TBAF (1.0 M, 0.2 ml) was added dropwise to the reaction system under ice bath conditions and the reaction was continued with stirring for 2 h. The reaction completion was confirmed by LCMS. Ethyl acetate and saturated ammonium chloride solution were added to the reaction solution. The organic phase was dried, concentrated to dryness and subjected to preparation plate separation to obtain a pale yellow solid compound 9 (5 mg, yield: 60%).

LCMS (ESI-MS) m/z: 661.4 $(M+H)^+$.

1H NMR (400 MHz, DMSO-d6) δ 9.68 (s, 1H), 8.52-8.48 (m, 2H), 8.30 (d, J=2.2 Hz, 1H), 7.96 (d, J=3.0 Hz, 1H), 7.47-7.40 (m, 2H), 7.21 (d, J=9.0 Hz, 1H), 7.17 (s, 1H), 7.10 (d, J=2.2 Hz, 1H), 6.63 (s, 2H), 6.52 (s, 1H), 5.32-5.28 (m, 2H), 5.18-5.14 (m, 1H), 4.54 (t, J=6.5 Hz, 2H), 4.44 (t, J=6.0 Hz, 2H), 4.39 (t, J=5.5 Hz, 2H), 4.17 (t, J=5.3 Hz, 2H), 3.11 (t, J=5.0 Hz, 4H), 2.39 (d, J=7.8 Hz, 4H), 1.97 (d, J=7.7 Hz, 4H). 1.20 (s, 6H).

Example 10 9-fluoro-2-(3'-(hydroxymethyl)-1-methyl-5-((5-(4-(oxetan-3-yl) piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

10

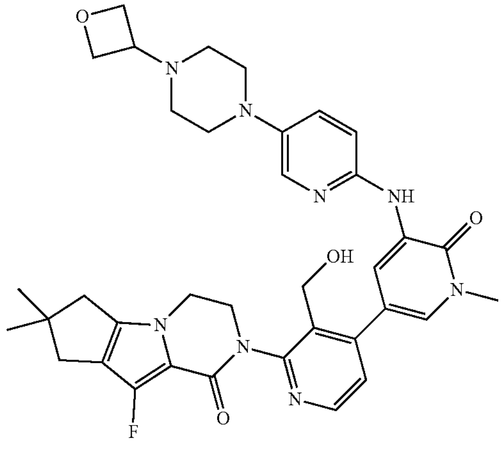

A synthetic method similar to that of Example 1 was used, in which tert-butyl (S)-3-methylpiperazine-1-carboxylate was replaced by tert-butylpiperazine-1-carboxylate to obtain the title product 10 with a yield of 19%.

1H NMR (400 MHz, DMSO-d6) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.93 (t, J=5.1 Hz, 1H), 4.52 (t, J=6.5 Hz, 2H), 4.50-4.33 (m, 4H), 4.31-4.12 (m, 3H), 3.89-3.79 (m, 1H), 3.60 (s, 3H), 3.53-3.40 (m, 1H), 3.08 (t, J=5.0 Hz, 4H), 2.57 (q, J=8.9 Hz, 2H), 2.42-2.35 (m, 6H), 1.22 (s, 6H).

LCMS (ESI-MS) m/z: 668.8 $(M+H)^+$.

Example 11 2-(5-((5-(2-oxa-7-azaspiro[3.5]nonan-7-yl)pyridin-2-yl) amino)-3'-(hydroxymethyl)-1-methyl-6-oxo-1,6-dihydro-[3,4'-bipyridin]-2'-yl)-9-fluoro-7,7-dimethyl-3,4,7,8-tetrahydro-2H-cyclopenta[4,5]pyrrolo[1,2-a]pyrazin-1(6H)-one

11

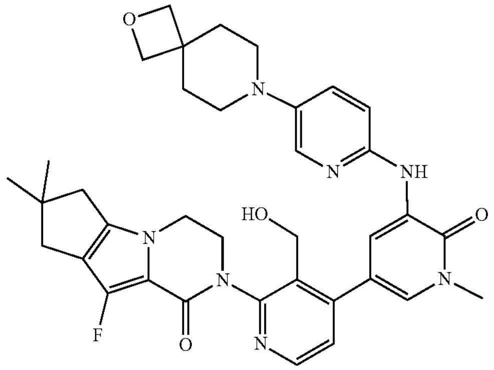

A synthetic method similar to that of Example 1 was used, in which tert-butyl (S)-3-methylpiperazine-1-carboxylate was replaced by 2-oxa-7-azaspiro[3.5]nonane to obtain the title product 11 with a yield of 26%.

1H NMR (400 MHz, DMSO-d6) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.93 (t, J=5.1 Hz, 1H), 4.52 (t, J=6.5 Hz, 2H), 4.50-4.33 (m, 4H), 4.31-4.12 (m, 3H), 3.89-3.79 (m, 1H), 3.60 (s, 3H), 3.08 (t, J=5.0 Hz, 4H), 2.57 (q, J=8.9 Hz, 2H), 2.42-2.35 (m, 2H), 1.65-1.43 (m, 4H), 1.22 (s, 6H).

LCMS (ESI-MS) m/z: 653.8 $(M+H)^+$.

Example 12 9-fluoro-2-(3'-(hydroxymethyl)-1-methyl-5-((5-(2-methyl-2,7-diazaspiro[3.5]nonan-7-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

12

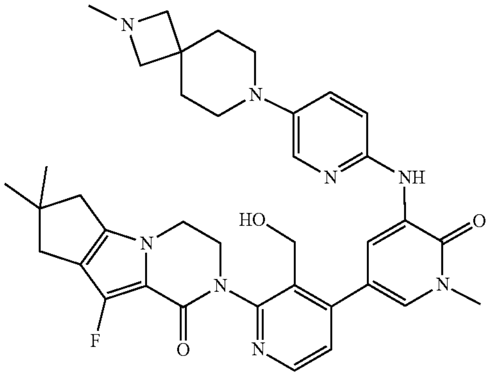

A synthetic method similar to that of Example 1 was used, in which tert-butyl (S)-3-methylpiperazine-1-carboxylate was replaced by 2-methyl-2,7-diazaspiro[3.5]nonane to obtain the title product 12 with a yield of 29%.

1H NMR (400 MHz, DMSO-$d_6$) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.93 (t, J=5.1 Hz, 1H), 4.52 (t, J=6.5 Hz, 2H), 4.31-4.12 (m, 3H), 3.89-3.79 (m, 1H), 3.60 (s, 3H), 3.08 (t, J=5.0 Hz, 4H), 2.57 (q, J=8.9 Hz, 2H), 2.42-2.35 (m, 6H), 2.21 (s, 3H), 1.65-1.43 (m, 4H), 1.22 (s, 6H).

LCMS (ESI-MS) m/z: 666.8 $(M+H)^+$.

Example 13 9-fluoro-2-(5-((5-(2-hydroxy-7-azaspiro[3.5]nonan-7-yl)pyridin-2-yl)amino)-3'-(hydroxymethyl)-1-methyl-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

13

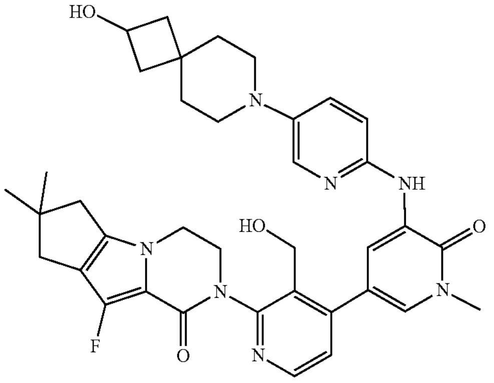

A synthetic method similar to that of Example 1 was used, in which tert-butyl (S)-3-methylpiperazine-1-carboxylate was replaced by 2-methyl-2,7-diazaspiro[3.5]nonane to obtain the title product 13 with a yield of 17%.

1H NMR (400 MHz, DMSO-d6) δ1H NMR (400 MHz, DMSO-d6) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.94 (t, J=5.1 Hz, 1H), 4.55 (td, J=6.5, 2.9 Hz, 2H), 4.29-4.19 (m, 1H), 4.25-4.12 (m, 3H), 3.82 (d, J=11.1 Hz, 1H), 3.67 (d, J=5.5 Hz, 1H), 3.60 (s, 3H), 3.40 (t, J=6.2 Hz, 4H), 2.45 (s, 2H), 2.36-2.28 (m, 2H), 2.09-1.75 (m, 8H), 1.22 (s, 6H).

LCMS (ESI-MS) m/z: 667.8 $(M+H)^+$.

Example 14 9-fluoro-2-(3'-(hydroxymethyl)-1-methyl-5-((5-(4-methylpiperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

14

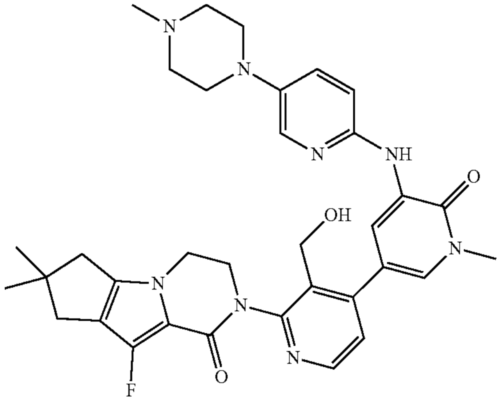

A synthetic method similar to that of Example 1 was used, in which tert-butyl (S)-3-methylpiperazine-1-carboxylate was replaced by 1-methylpiperazine to obtain the title product 14 with a yield of 21%.

$^1$H NMR (400 MHz, DMSO-$d_6$) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.40-7.32 (m, 2H), 7.24 (d, J=9.0 Hz, 1H), 4.94 (t, J=5.1 Hz, 1H), 4.39 (d, J=5.1 Hz, 2H), 3.58 (s, 3H), 3.08 (t, 4H), 2.41-2.30 (m, 11H), 2.39-2.19 (m, 4H), 1.22 (s, 6H).

LCMS (ESI-MS) m/z: 626.7 $(M+H)^+$.

Example 15 9-fluoro-2-(3'-(hydroxymethyl)-1-methyl-5-((4-(4-(oxetan-3-yl) piperazin-1-yl)phenyl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

15

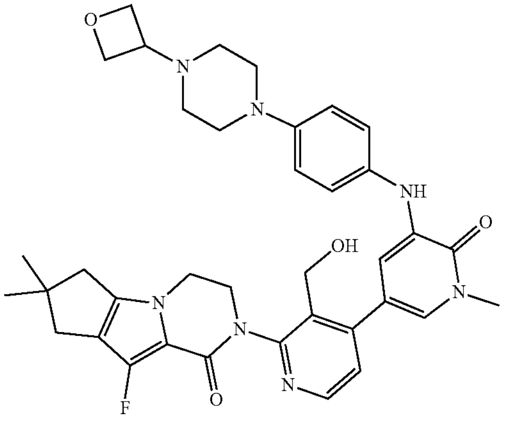

A synthetic method similar to that of Example 1 was used, in which tert-butyl (S)-3-methylpiperazine-1-carboxylate was replaced by tert-butylpiperazine-1-carboxylate and 5-chloro-2-nitropyridine was replaced by 1-bromo-4-chlorobenzene to obtain the title product 15 with a yield of 19%.

$^1$H NMR (400 MHz, DMSO-$d_6$) δ 8.61 (d, J=2.3 Hz, 1H), 8.48 (d, J=5.0 Hz, 1H), 8.44 (s, 1H), 7.83 (d, J=2.8 Hz, 1H), 7.45 (d, J=2.3 Hz, 1H), 7.26 (d, J=9.0 Hz, 2H), 7.04 (d, J=9.0 Hz, 2H), 4.93 (t, J=5.1 Hz, 1H), 4.52 (t, J=6.5 Hz, 2H), 4.50-4.33 (m, 4H), 4.31-4.12 (m, 3H), 3.89-3.79 (m, 1H), 3.60 (s, 3H), 3.53-3.40 (m, 1H), 3.08 (t, J=5.0 Hz, 4H), 2.57 (q, J=8.9 Hz, 2H), 2.42-2.35 (m, 6H), 1.22 (s, 6H).

LCMS (ESI-MS) m/z: 667.8 (M+H)$^+$.

Example 16 9-fluoro-2-(3'-(hydroxymethyl)-1-methyl-5-((6-(4-(oxetan-3-yl) piperazin-1-yl)pyridin-3-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

16

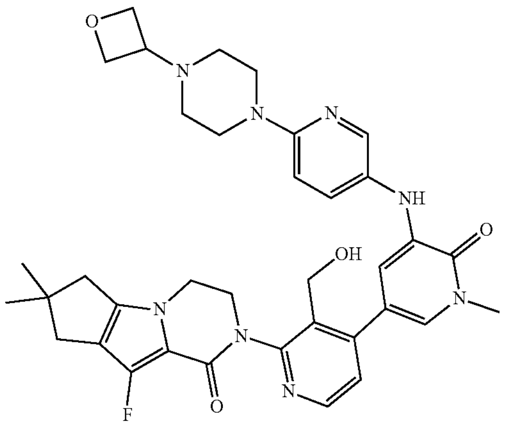

A synthetic method similar to that of Example 1 was used, in which tert-butyl (S)-3-methylpiperazine-1-carboxylate was replaced by tert-butylpiperazine-1-carboxylate and 5-chloro-2-nitropyridine was replaced by 2-bromo-5-chloropyridine to obtain the title product 16 in a yield of 23%.

1H NMR (400 MHz, DMSO-d6) δ 8.60 (d, J=2.3 Hz, 1H), 8.47 (d, J=5.0 Hz, 1H), 8.41 (s, 1H), 7.82 (d, J=2.9 Hz, 1H), 7.44 (d, J=2.3 Hz, 1H), 7.37-7.30 (m, 2H), 7.21 (d, J=9.0 Hz, 1H), 4.93 (t, J=5.1 Hz, 1H), 4.52 (t, J=6.5 Hz, 2H), 4.50-4.33 (m, 4H), 4.31-4.12 (m, 3H), 3.89-3.79 (m, 1H), 3.60 (s, 3H), 3.53-3.40 (m, 1H), 3.08 (t, J=5.0 Hz, 4H), 2.57 (q, J=8.9 Hz, 2H), 2.42-2.35 (m, 6H), 1.22 (s, 6H).

LCMS (ESI-MS) m/z: 668.8 (M+H)$^+$.

Example 17 (S)-9-bromo-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

17

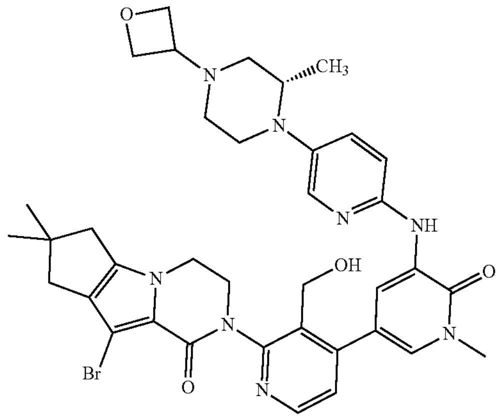

A synthetic method similar to that of Example 1 was used, and the intermediate 1b was synthesized to obtain the title product 17 with a yield of 29%.

1H NMR (400 MHz, DMSO-d6) δ 8.59 (d, J=2.3 Hz, 1H), 8.46 (d, J=5.0 Hz, 1H), 8.42 (s, 1H), 7.82 (d, J=2.9 Hz, 1H), 7.43 (d, J=2.3 Hz, 1H), 7.38-7.30 (m, 2H), 7.24-7.20 (m, 1H), 4.93 (t, J=5.1 Hz, 1H), 4.62-4.32 (m, 6H), 4.21 (d, J=10.2 Hz, 3H), 3.82 (d, J=6.4 Hz, 1H), 3.65 (d, J=5.9 Hz, 1H), 3.59 (s, 3H), 3.43-3.33 (m, 1H), 3.08 (d, J=11.5 Hz, 1H), 2.93 (t, J=9.9 Hz, 1H), 2.69-2.50 (m, 3H), 2.37-2.23 (m, 4H), 2.17 (t, J=9.7 Hz, 1H), 1.21 (d, J=2.9 Hz, 6H), 0.91 (d, J=6.3 Hz, 3H). LCMS (ESI-MS) m/z: 743.7 (M+H)+.

Example 18 (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-1-oxo-1,3,4,6,7,8-hexahydro-2H-cyclopenta[4,5]pyrrolo[1,2-a]pyrazine-9-carbonitrile

18

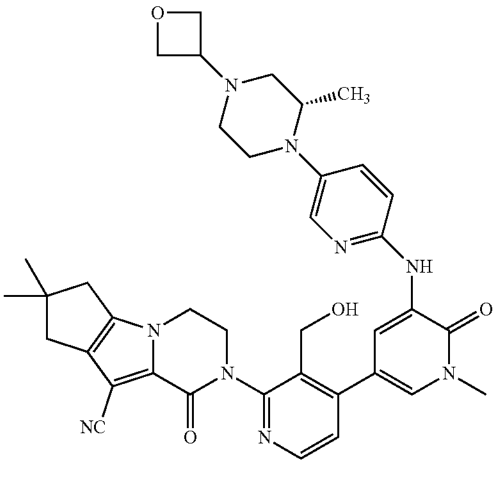

-continued

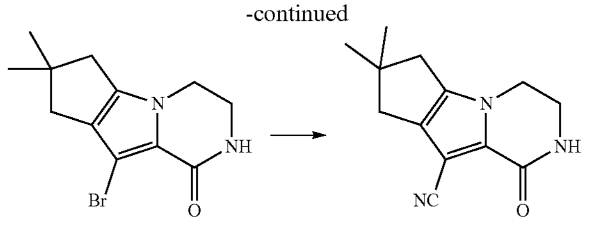

1b 18a

Step 1 7,7-dimethyl-1-carbonyl-1,3,4,6,7,8-hexahydro-2H-cyclopenta[4,5]pyrrolo[1,2-a]pyrazine-9-carbonitrile Compound 1b (0.5 g, 1.77 mmol) was dissolved in toluene (10 mL). Copper(I) cyanide (0.16 g, 1.77 mmol) and tetrakis(triphenylphosphine)-palladium (50 mg) were added. The reaction solution was stirred for 3 h at 100° C. under nitrogen protection. After cooling, the reaction was washed by adding saturated saline and extracted with ethyl acetate (50×2 mL). The combined organic phases were dried over anhydrous sodium sulfate, filtered and spin dried to obtain a crude product, which was purified by silica gel column chromatography to obtain compound 18a (280 mg) with a yield of 69.1%.

MS m/z (ESI): 230 $(M+1)^+$

This step was followed by a similar reaction as in Example 1 after step 5 to produce the title product 18 with a yield of 19%.

1H NMR (400 MHz, DMSO-d6) δ 8.59 (d, J=2.4 Hz, 1H), 8.48 (d, J=5.2 Hz, 1H), 8.44 (s, 1H), 7.81 (d, J=2.8 Hz, 1H), 7.40-7.34 (m, 3H), 7.24-7.22 (m, 1H), 4.99 (s, 1H), 4.55-4.38 (m, 6H), 4.30-4.28 (m, 3H), 3.90 (s, 1H), 3.67-3.65 (m, 1H), 3.59 (s, 3H), 3.38-3.34 (m, 1H), 3.09-3.05 (m, 1H), 2.95-2.90 (m, 1H), 2.66-2.65 (m, 2H), 2.31-2.13 (m, 6H), 1.22 (s, 6H), 0.91 (d, J=6.4 Hz, 3H).

LCMS (ESI-MS) m/z: 689.8 $(M+H)^+$.

Example 19 (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-9-(trifluoromethyl)-3,4,7,8-hexahydro-2H-cyclopenta[4,5]pyrrolo[1,2-a]pyrazine-1(6H)-one

19

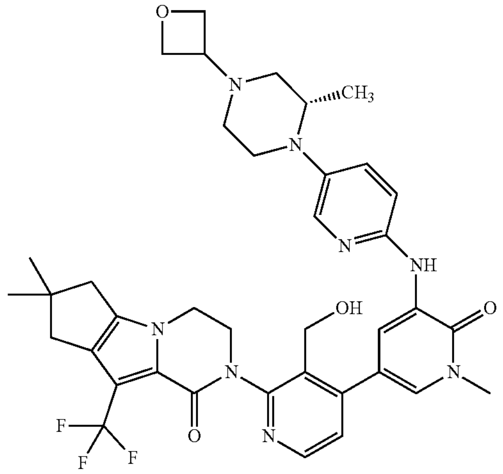

-continued

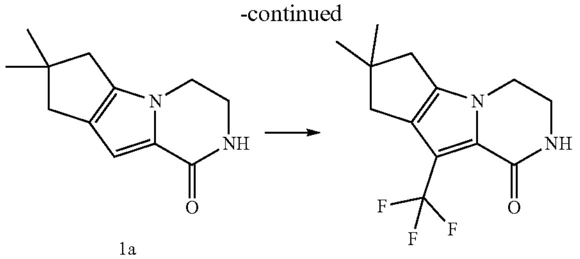

1a 19a

Step 1 7,7-dimethyl-9-(trifluoromethyl)-3,4,7,8-tetrahydro-2H-cyclopenta[4,5]pyrrolo [1,2-a] pyrazin-1(6H)-one Compound 1a (0.5 g, 2.45 mmol) was dissolved in DMF (10 mL) and diiododifluoromethane (1.48 g, 4.9 mmol) was added. The reaction solution was stirred for 18 h under strong light and nitrogen protection. After cooling, the reaction was washed by adding saturated saline and extracted with ethyl acetate (50×2 mL). The combined organic phases were dried over anhydrous sodium sulfate, filtered and spin dried to obtain a crude product, which was purified by silica gel column chromatography to obtain compound 19a (180 mg) with a yield of 27%.

MS m/z (ESI): 230 $(M+1)^+$

This step was followed by a similar reaction as in Example 1 after step 5 to produce the title product 19 with a yield of 16%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 3.90 (d, J=11.0 Hz, 2H), 3.36 (d, J=11.7 Hz, 2H), 3.17-3.01 (m, 6H), 2.81 (s, 3H), 2.76 (d, J=7.2 Hz, 2H), 2.50 (s, 1H), 2.46 (s, 3H), 2.33 (s, 3H), 2.25 (s, 3H), 2.12 (s, 3H), 1.97 (td, J=13.4, 12.8, 4.0 Hz, 2H), 1.81 (d, J=13.9 Hz, 2H), 1.78 (d, J=12.5 Hz, 2H), 1.67-1.53 (m, 3H), 1.28-1.22 (m, 4H), 0.86 (t, J=7.0 Hz, 3H).

LCMS (ESI-MS) m/z: 732.8 $(M+H)^+$.

Example 20 (S)-9-ethoxy-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridyl]-2'-yl)-7,7-dimethyl-3,4,7,8-tetrahydro-2H-cyclopenta[4,5]pyrrolo[1,2-a]pyrazin-1(6H)-one

20

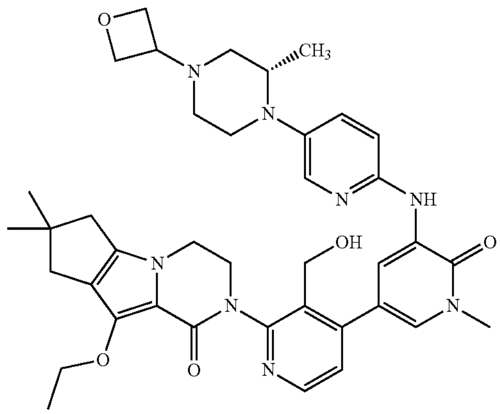

-continued

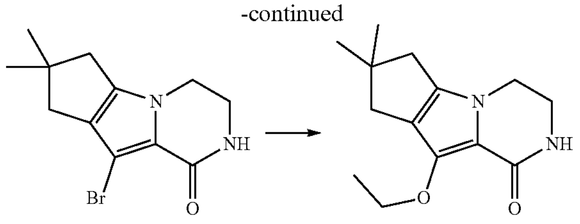

1b 20a

Step 1 9-ethoxy-7,7-dimethyl-3,4,7,8-tetrahydro-2H-cyclopenta[4,5]pyrrolo [1,2-a]pyrazin-1(6H)-one Compound 1b (0.5 g, 1.77 mmol) was dissolved in dichloromethane (10 mL) and sodium ethoxide (0.16 g, 1.77 mmol) was added. The reaction solution was sealed under nitrogen protection and reacted with stirring at 50° C. for 18 h. After cooling, the reaction was washed by adding saturated saline and extracted with ethyl acetate (50×2 mL). The combined organic phases were dried over anhydrous sodium sulfate, filtered and spin dried to obtain a crude product, which was purified by silica gel column chromatography to obtain compound 20a (210 mg) with a yield of 47.8%.

MS m/z (ESI): 248.3 $(M+1)^+$

This step was followed by a similar reaction as in Example 1 after step 5 to produce the title product 20 with a yield of 30%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 4.07 (m, 2H), 3.90 (d, J=11.0 Hz, 2H), 3.36 (d, J=11.7 Hz, 2H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.38 (m, 2H), 1.27-1.21 (m, 4H), 0.86 (t, J=7.0 Hz, 3H).

LCMS (ESI-MS) m/z: 708.9 $(M+H)^+$.

Example 21 (S)-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-9-methoxy-7,7-dimethyl-3,4,7,8-tetrahydro-2H-cyclopenta[4,5]pyrrolo[1,2-a]pyrazin-1(6H)-one

21

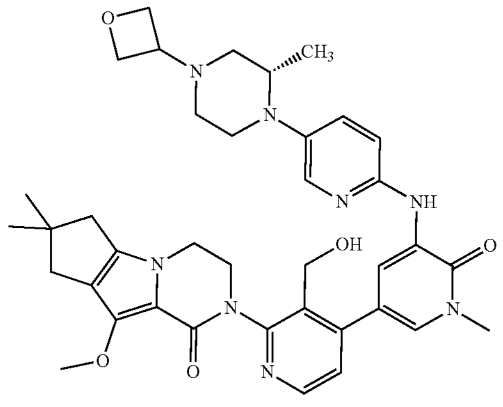

A synthetic method similar to that of Example 20 was used, in which sodium ethoxide was replaced by sodium methanol to obtain the title product 21 with a yield of 35%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 3.90 (d, J=11.0 Hz, 2H), 3.83 (s, 3H), 3.36 (d, J=11.7 Hz, 2H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.27-1.21 (m, 4H), 0.86 (t, J=7.0 Hz, 3H).

LCMS (ESI-MS) m/z: 694.8 $(M+H)^+$.

Example 22 (S)-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-7,7-dimethyl-9-propoxy-3,4,7,8-tetrahydro-2H-cyclopenta[4,5]pyrrolo[1,2-a]pyrazin-1(6H)-one

22

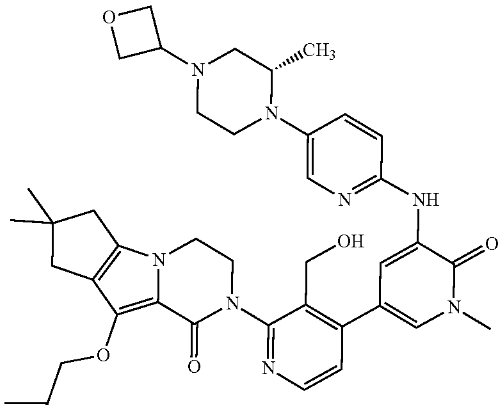

A synthetic method similar to that of Example 20 was used, in which sodium ethoxide was replaced by sodium propanol to obtain the title product 22 with a yield of 26%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 3.99 (m, 2H), 390 (d, J=11.0 Hz, 2H), 3.36 (d, J=11.7 Hz, 2H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.72 (m, 2H), 1.69-1.56 (m, 3H), 1.27-1.21 (m, 4H), 0.99 (m, 3H), 0.86 (t, J=7.0 Hz, 3H).

LCMS (ESI-MS) m/z: 722.9 $(M+H)^+$.

Example 23 (S)-9-cyclopropoxy-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

23

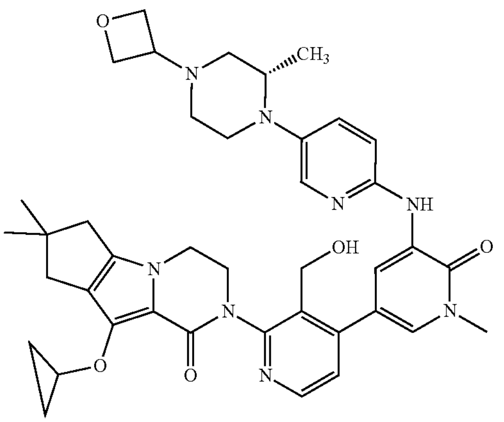

A synthetic method similar to that of Example 20 was used, in which sodium ethoxide was replaced by sodium cyclopropanolate to obtain the title product 23 with a yield of 17%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 390 (d, J=11.0 Hz, 2H), 3.37 (m, 3H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.27-1.21 (m, 4H), 0.86 (t, J=7.0 Hz, 3H), 0.58 (m, 2H), 0.34 (m, 2H).

LCMS (ESI-MS) m/z: 720.9 (M+H)$^+$.

Example 24 (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-9-isopropoxy-7,7-dimethyl-3,4,7,8-tetrahydro-2H-cyclopenta[4,5]pyrrolo[1,2-a]pyrazin-1(6H)-one

24

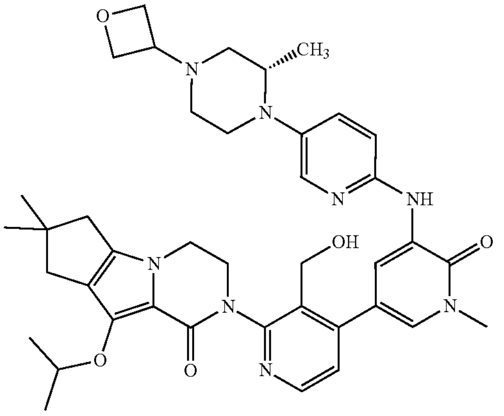

A synthetic method similar to that of Example 23 was used, and sodium ethoxide was replaced by sodium isopropylate to obtain the title product 24 with a yield of 25%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 4.69 (m, 1H), 3.90 (d, J=11.0 Hz, 2H), 3.36 (d, J=11.7 Hz, 2H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.31 (m, 6H), 1.27-1.21 (m, 4H), 0.99 (m, 3H), 0.86 (t, J=7.0 Hz, 3H).

LCMS (ESI-MS) m/z: 722.9 (M+H)$^+$.

Example 25 (S)-9-amino-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one

25

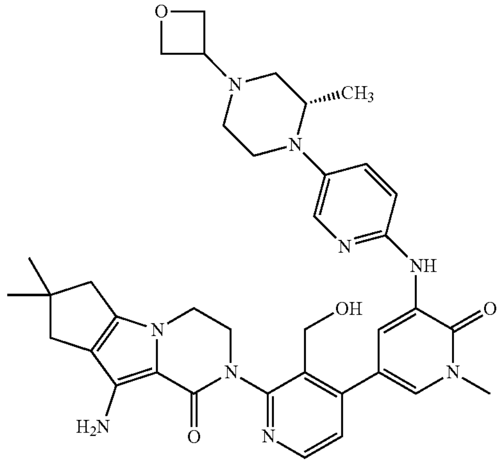

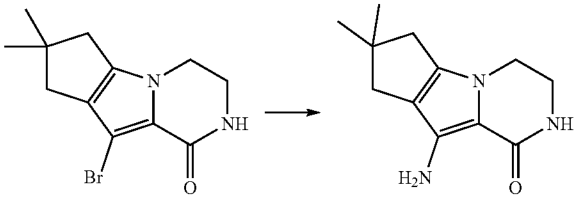

1b

25a

Step 1 9-amino-7,7-dimethyl-3,4,7,8-tetrahydro-2H-cyclopenta[4,5]pyrrolo [1,2-a]pyrazin-1(6H)-one Compound 1b (0.5 g, 1.77 mmol) was dissolved in a solution of ammonia in methanol (10 mL). The reaction solution was stirred at 80° C. for 3 h under nitrogen protection in a sealed tube. After cooling, the reaction was washed by adding saturated saline and extracted with ethyl acetate (50×2 mL). The combined organic phases were dried over anhydrous sodium sulfate, filtered and spin dried to obtain a crude product, which was purified by silica gel column chromatography to obtain compound 25a (156 mg) with a yield of 40.1%.

MS m/z (ESI): 219 (M+1)$^+$

This step was followed by a similar reaction as in Example 1 after step 5 to produce the title product 25 with a yield of 11%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 5.82 (s, 2H), 4.47 (s, 2H), 3.90 (d, J=11.0 Hz, 2H), 3.36 (d, J=11.7 Hz, 2H), 3.19-3.01 (m, 6H), 2.81 (s, 3H), 2.76 (d, J=7.2 Hz, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.28-1.21 (m, 4H), 0.88 (t, J=7.0 Hz, 3H).

LCMS (ESI-MS) m/z: 679.8 $(M+H)^+$.

Example 26 (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-9-methylamino-7,7-dimethyl-3,4,7,8-tetrahydro-2H-cyclopenta[4,5]pyrrolo[1,2-a]pyrazin-1(6H)-one

26

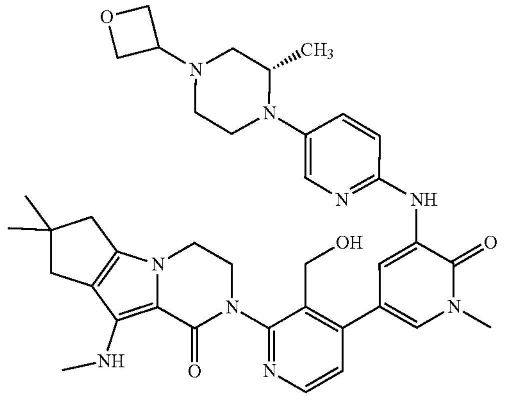

A synthetic method similar to that of Example 25 was used, in which the solution of ammonia in methanol was replaced by methylamine hydrochloride to obtain the title product 26 with a yield of 24.6%.

$^1$H NMR (400 MHz, Methanol-$d_4$) δ 7.38 (d, J=1.9 Hz, 1H), 7.25 (d, J=1.8 Hz, 1H), 7.07 (d, J=7.6 Hz, 1H), 6.85 (dd, J=7.7, 1.6 Hz, 1H), 6.65 (d, J=1.5 Hz, 1H), 6.09 (s, 1H), 4.47 (s, 2H), 3.90 (d, J=11.0 Hz, 2H), 3.36 (d, J=11.7 Hz, 2H), 3.19-3.01 (m, 6H), 2.81 (s, 3H), 2.76 (d, J=7.2 Hz, 2H), 2.72 (s, 2H), 2.50 (s, 1H), 2.41 (s, 3H), 2.33 (s, 3H), 2.23 (s, 3H), 2.14 (s, 3H), 1.98 (td, J=13.4, 12.8, 4.0 Hz, 2H), 1.82 (d, J=13.9 Hz, 2H), 1.77 (d, J=12.5 Hz, 2H), 1.69-1.56 (m, 3H), 1.28-1.22 (m, 4H), 0.88 (t, J=7.0 Hz, 3H).

LCMS (ESI-MS) m/z: 693.9 $(M+H)^+$.

Example 27 (S)-9-bromo-2-(3'-(hydroxymethyl)-1-methyl-5-((5-(2-methyl-4-(oxetan-3-yl)piperazin-1-yl)pyridin-3-yl)amino)-6-oxo-1,6-dihydro-[3,4'-bipyridin]-2'-yl)-7,7-dimethyl-3,4,7,8-tetrahydro-2H-cyclopenta[4,5]pyrrolo[1,2-a]pyrazin-1(6H)-one-9-deuterium

27

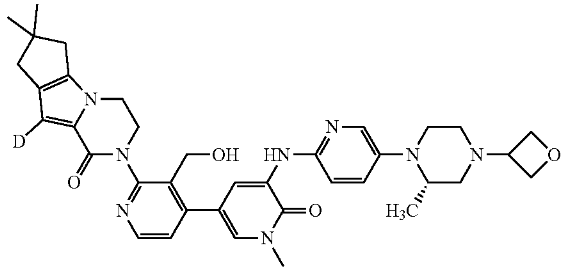

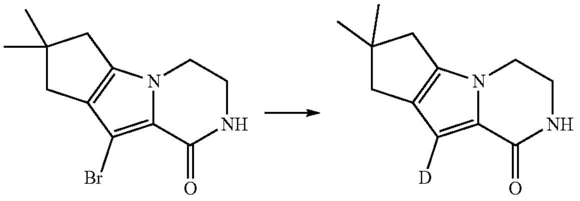

1b

27a

Step 1 7,7-dimethyl-3,4,7,8-tetrahydro-2H-cyclopenta[4,5]pyrrolo[1,2-a]pyrazin-1(6H)-one-9-deuterium Compound 1b (0.5 g, 1.77 mmol) was dissolved in tetrahydrofuran. The reaction solution was added with sodium deuterated borohydride under nitrogen protection and stirred for 3 h in an ice bath. The reaction was washed by adding saturated saline and extracted with ethyl acetate (50×2 mL). The combined organic phases were dried over anhydrous sodium sulfate, filtered and spin dried to obtain a crude product, which was purified by silica gel column chromatography to obtain compound 27a (160 mg) with a yield of 44.2%.

MS m/z (ESI): 206.3 $(M+1)^+$

This step was followed by a similar reaction as in Example 1 after step 5 to produce the title product 26 with a yield of 21%.

1H NMR (400 MHz, DMSO-d6) δ 8.64 (d, J=22.6 Hz, 2H), 8.47 (d, J=5.0 Hz, 1H), 7.92 (s, 1H), 7.45 (dd, J=9.7, 2.6 Hz, 2H), 7.36-7.24 (m, 2H), 4.83-4.60 (m, 4H), 4.40 (q, J=11.7 Hz, 3H), 4.23-4.04 (m, 3H), 3.79 (d, J=11.5 Hz, 1H), 3.56 (s, 3H), 3.18-3.05 (m, 3H), 2.54 (d, J=8.8 Hz, 2H), 2.42 (s, 2H), 1.18 (d, J=5.6 Hz, 8H), 0.90 (s, 3H).

MS m/z (ESI): 666.8 $[M+H]^+$.

Biological Experimental Examples:

Experiment 1: Study on the Activity of the Compound Inhibiting BTK Kinase

The BTK kinase inhibitory activity of the compound was determined using a mobility shift method with the reaction system (kinase solution, ATP, kinase substrate2). The compound was co-incubated with the enzyme for 30 minutes, and then the conversion rate was read using the Caliper EZ reader. The compound inhibition rate was determined using the calculation formula and the data was fitted using Graphpad to derive the $IC_{50}$ value for the compounds of this application.

Test Result

The compounds of the present application have a significant inhibitory effect on BTK kinase with a 50% inhibition concentration of BTK<0.75 nM, and their selectivity is better than ibrutinib.

TABLE 2

Study on the activity of the compound inhibiting BTK kinase

| Compound No. | BTK ($IC_{50}$, nM) |
|---|---|
| H01 | 0.23 |
| H02 | 0.59 |
| H03 | 0.14 |
| H04 | 0.26 |
| H05 | 0.69 |
| H06 | 0.41 |
| H07 | 0.38 |
| H08 | 0.23 |
| H09 | 0.71 |
| H10 | 0.21 |
| H11 | 0.26 |
| H12 | 0.49 |
| H13 | 0.18 |
| H14 | 0.27 |
| H15 | 0.68 |
| H16 | 0.17 |
| H17 | 0.73 |
| H18 | 0.65 |
| H19 | 0.52 |
| H20 | 0.55 |
| H21 | 0.38 |
| H22 | 0.74 |
| H23 | 0.51 |
| H24 | 0.65 |
| H25 | 0.44 |
| H26 | 0.46 |
| Ibrutinib | 0.78 |

Experiment 2. Inhibitory Effect of the Compound on Cell Proliferation

1. Experimental Aims and Methods

This experiment was to determine the effect of the compound on cell proliferation.

To determine the inhibitory effect of the compound on the proliferation of tumour cells, tumour cells (A20 5E6 cells) were cultured to a certain amount and seeded into 96-well plates. Different concentrations of the compound were added to the plates according to the experimental requirements and the inhibitory effect on tumour cells was observed after 1 h, 2 h, 4 h, 8 h and 24 h. The absorbance value was measured after the addition of CCK8 and 2 h incubation to determine the inhibitory effect of the compound on cell proliferation. The $IC_{50}$ value of the compound was obtained by data fitted with Graphpad.

2. Result of the Experiment

The compounds of this application can effectively inhibit the proliferation of tumour cells and are more effective than ibrutinib.

TABLE 3

Inhibitory effect of the compound on cell proliferation

| Compound No. | $IC_{50}$ (μM) |
|---|---|
| H01 | 0.024 |
| H02 | 0.023 |
| H03 | 0.061 |
| H04 | 0.026 |
| H05 | 0.023 |
| H06 | 0.031 |
| H07 | 0.040 |
| H08 | 0.029 |
| H09 | 0.031 |
| H10 | 0.021 |
| H11 | 0.013 |
| H12 | 0.013 |
| H13 | 0.019 |
| H14 | 0.047 |
| H15 | 0.023 |
| H16 | 0.047 |
| Ibrutinib | 0.087 |

Experiment 3. Relieving Effect of the Compound on Rheumatoid Arthritis

1. Aim and Method of the Experiment

The aim of this experiment was to test the effect of the compound on a type 11 collagen-induced arthritis model in rats. The rats were inoculated and molded by intradermal immune injection in root of tail twice on day 0 and day 7, and were clinically scored. Animals that were successfully modelled (clinical score>3 or more) were randomly assigned to each dosing group for therapeutic administration. At the same time, various indicators were tested, including clinical score, toe volume measurement (twice a week), etc.

2. Result of the Experiment

The compounds of this application can effectively relieve arthritis and reduce toe volume of the animals, and alleviate the progression of arthritis 14 days after administration, which showed superior effect over ibrutinib.

Experiment 4: Effect of the Compound on Lymphoma

1. Aim and Method of the Experiment

The aim of this experiment was to test the effect of the compound on lymphoma. A20 5E6 cells were cultivated, and inoculated subcutaneously into SCID nude mice. Tumour volumes were measured twice a week. After the tumour species had grown to a certain volume, the successfully molded animals were randomly allocated to each dose administration group for therapeutic administration. At the same time, the changes in tumor size and body weight were observed every day.

2. Result of the Experiment

The compounds of this application can effectively reduce the size of solid tumours in animals, alleviate tumour progression and improve body weight in animals, which showed better results than ibrutinib.

Experiment 5. Effect of the Compound on Acute Pneumonia

1. Aim and Method of the Experiment

The aim of this experiment was to test the effect of the compounds on acute pneumonia.

The animals were anesthetized with chloral hydrate, and then administered lipopolysaccharide to obtain chemically induced acute pneumonia model. Animals were divided into control and model groups. Bronchoalveolar lavage fluid and lung tissues were collected at various time periods after lipopolysaccharide inhalation, and the animals were monitored for lung injury and other indicators by a respiratory function monitor. After tissue collection, tissue sections and staining were performed, and cell count and corresponding inflammatory factors were measured in bronchoalveolar lavage fluid.

2. Result of the Experiment

After administration, the compounds of this application can effectively improve the inflammatory cell infiltration shown in HE staining compared to the control group. Lymphocytes, monocytes and neutrophils in bronchoalveolar lavage fluid were significantly reduced compared to the control group. IL-1p levels in tissue and blood were also significantly reduced compared to the control group. The effect of the compounds of the present application was superior than ibrutinib.

Experiment 6. Effect of the Compound on Systemic Lupus Erythematosus

1. Aim and Method of the Experiment

The aim of this experiment was to test the pharmacodynamic effects of the test compound on spontaneous systemic lupus erythematosus in MRL/lpr mice.

The serum of MRL/lpr mice was collected after 7 days of adaptation, and the contents of antinuclear antibodies in blood were measured. The mice were grouped for administration. Blood samples were collected at weeks 4, 8, 16 and 20 to determine anti-nuclear antibodies, anti-single stranded deformable DNA antibodies, anti-histone, urea nitrogen, creatinine and urine protein in blood tests. Results of the efficacy of the compound on systemic lupus erythematosus were observed.

2. Result of the Experiment

The compounds of the present application can effectively reduce the content of relevant indicators in the blood of animals and effectively alleviate the progression of systemic lupus erythematosus in animals.

Experiment 7. Inhibition Effect of the Compound on hERG Potassium Channel Current 1. Aim and Method of the Experiment The aim of this experiment was to apply electrophysiological manual membrane clamp to detect the effect of the compound on hERG potassium channel.

The hERG potassium ion channel was overexpressed in HEK293 cells, which was incubated in a 37° C. 5% $CO_2$ incubator using a medium consisting of DMEM/150% fetal bovine serum/1% penicillin-streptomycin. During the experiment, the cells were transferred to a cell bath embedded in an inverted microscope stage, perfused with extracellular fluid, and stabilized for 5 minutes. The experiment could be started after the cells precipitated. Membrane currents were recorded using a HEKA EPC-10 membrane clamp amplifier and PATCHMASTER acquisition system (HEKA Instruments Inc., D-67466 Lambrcht, Pfalz, Germany).

The experiments were performed in whole-cell recording mode, with current values recorded according to preset electrophysiological stimulation protocol. Perfusion was performed and recorded using the drugs to be tested, in a concentration ranging from low to high. Data were collected using PATCHMASTER V2X60 (HEKA Instruments Inc., D-67466 Lambrecht, Pfalz, Germany) and Origin 8.5 (OriginLab Corporation, Northampton, MA) software was used for analysis and statistics.

2. Result of the Experiment

The compounds of the present application have hERG IC50>40 μM, with a relatively good cardiac safety.

Experiment 8. Pharmacokinetic Result of the Compound

1. Aim and Method of the Experiment

The aim of this experiment was to test the content of the compound in plasma and tissue.

The content of the compound was measured in plasma and tissues before administration, and 15 mins, 30 mins, 1 hr, 2 hr, 4 hr, 8 hr, 12 hr, 24 hr and 48 hr after administration to SD rats.

2. Result of the Experiment $T_{1/2}$ on the rats was 3-4 h.

Experiment 9. Result of Acute Toxicity Experiment on the Compound

1. Aim and Method of the Experiment

The aim of this experiment was to test the toxic effect of the compound on mice.

Mice were administered with different doses of the compounds at a single time and observed for 14 days. Death, poisoning reaction, weight change, diet, appearance, and behavior of the animals were recorded. At the end, the animals were dissected, and organs were taken. Histopathological examination was performed.

2. Result of the Experiment

The compounds of the present application have an LD50>1000 mg/kg and is safe. Compared to the control mice, no weight or behavioural abnormalities were observed in the administered mice within 14 days from the date of administration, and no significant organ lesions were found on endpoint autopsy. The compounds of the present application did not show significant toxicity. Blood analysis did not reveal any obvious abnormal indicators.

Experiment 10. Pre-Experiment Result of Chronic Toxicity of the Compound

1. Aim and Method of the Experiment

The aim of this experiment was to test the toxic effect of the compounds on rats after long-term administration.

Rats were administered with the compounds in different high doses for 21 days. The body weight and related physiological signs of the animals were observed every day, and death, poisoning reactions, weight changes, diet, appearance and behavior of the animals were recorded. After 21 days, the animals were dissected. Blood samples were collected for routine blood tests, blood biochemistry and coagulation tests. Organs were taken for histopathological examination.

2. Result of the Experiment

The compounds of the present application have an LD50>100 mg/kg and is relatively safe. Compared to the animals in the control group, no abnormal weight, behavior and physiological changes were observed in the animals in the drug administration group within 21 days from the date of administration, and no obvious organ lesions were found in the endpoint anatomy. The compounds of the present application did not show obvious toxicity. Blood analysis did not show any abnormality of relevant indicators in animals in the administration group.

The above are only the preferred examples of the present application and are not intended to limit the present application. Any modifications, equivalent substitutions and improvements made within the spirit and principle of the present application should be included in the protection scope of the present application.

The invention claimed is:

1. A compound of formula (I):

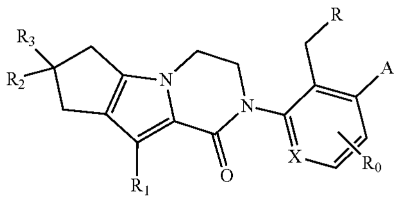

(I)

or a pharmaceutically acceptable salt, stereoisomer, or tautomer thereof, wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N;

R is OH;

$R_0$ is H;

A is

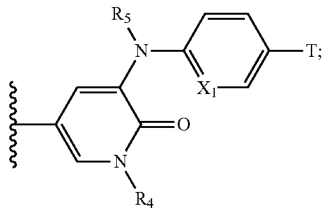

$R_4$ is $C_{1-6}$ alkyl;

$R_5$ is H or $C_{1-3}$ alkyl;

$X_1$ is N;

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

$T_1$ is $C_{1-6}$ alkyl; and $T_2$ is $C_{1-6}$ alkyl or 3- to 6-membered heterocycloalkyl.

2. The compound according to claim 1, or a pharmaceutically acceptable salt, stereoisomer, or tautomer thereof, wherein T is:

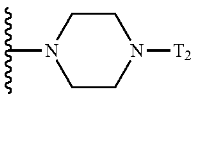

or

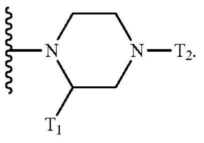

3. The compound according to claim 2, or a pharmaceutically acceptable salt, stereoisomer, or tautomer thereof, wherein:

$T_1$ is $CH_3$, $CH_2CH_3$, $CH_2CH_2CH_3$, or $CH(CH_3)_2$; and $T_2$ is $CH_3$, $CH_2CH_3$, $CH_2CH_2CH_3$, $CH(CH_3)_2$, or oxetanyl.

4. The compound according to claim 3, or a pharmaceutically acceptable salt, stereoisomer, or tautomer thereof, wherein T is:

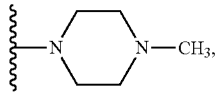

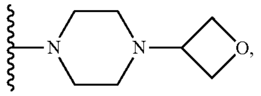

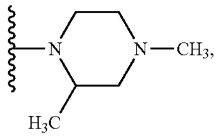

or

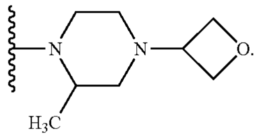

5. The compound according to claim 1, or a stereoisomer thereof, wherein the compound, or stereoisomer thereof, is selected from the group consisting of:

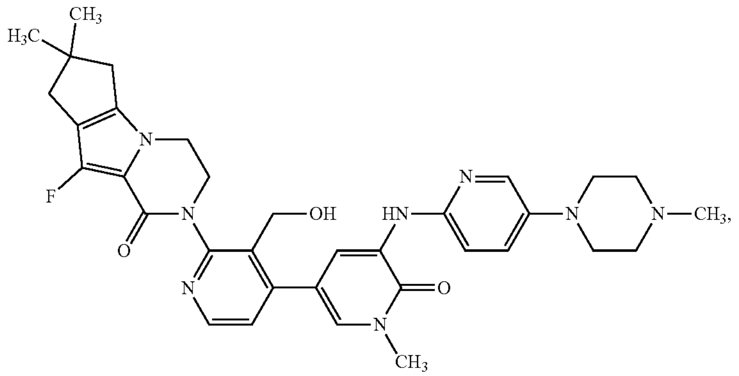

-continued
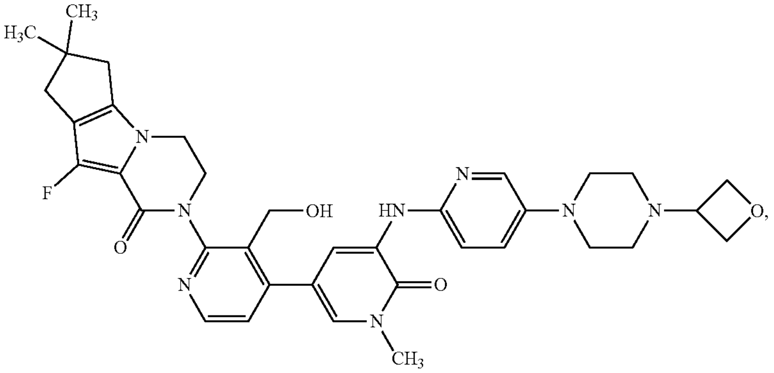
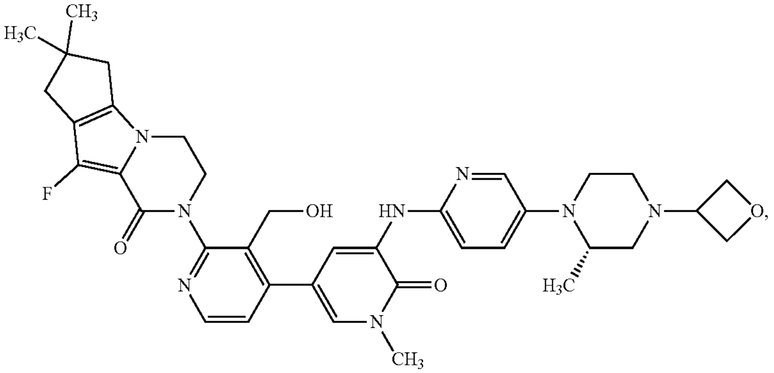
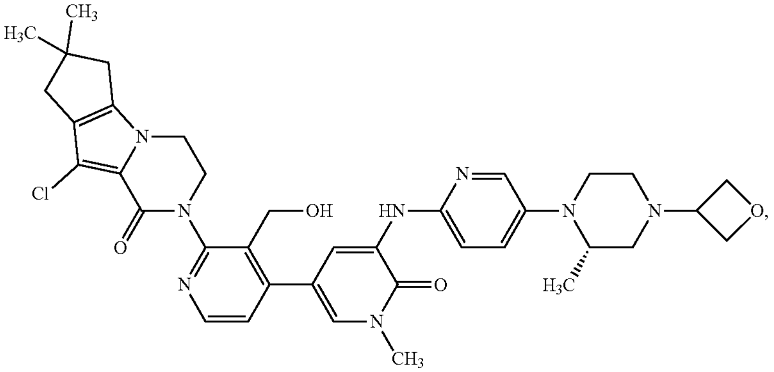
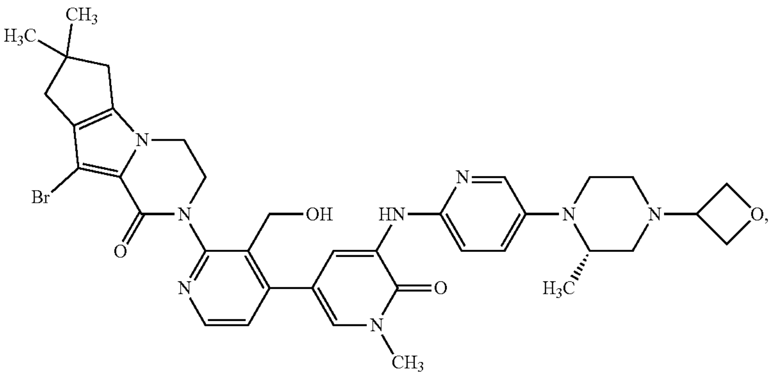

-continued
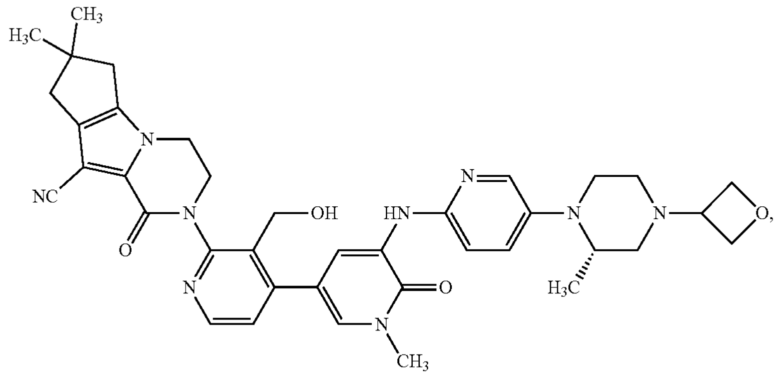
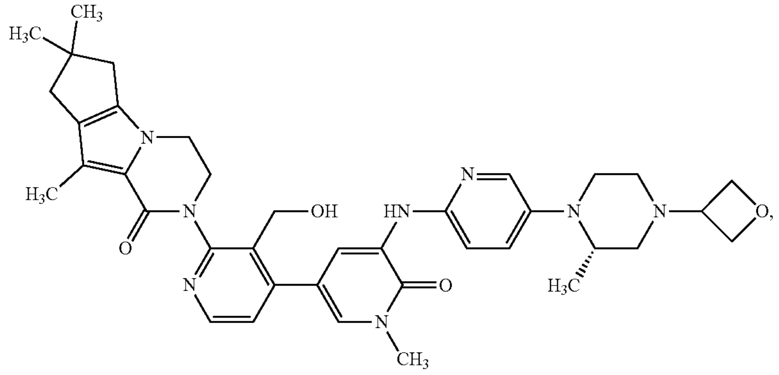
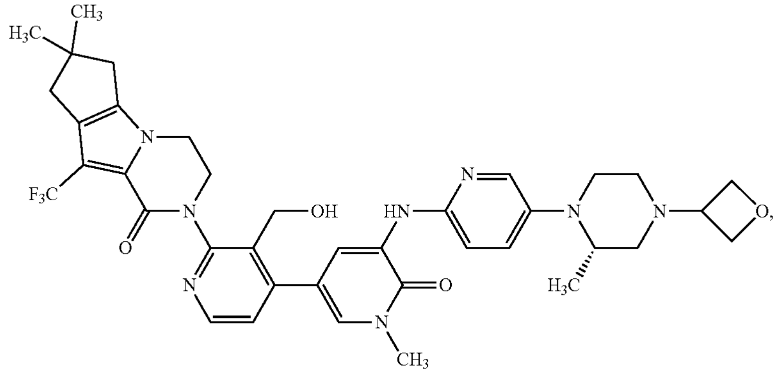
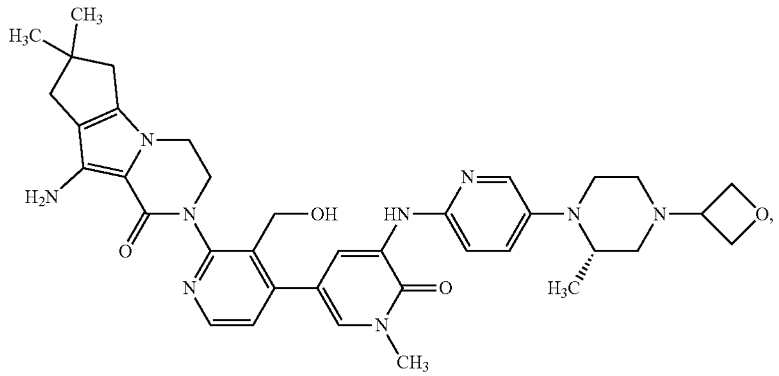

-continued
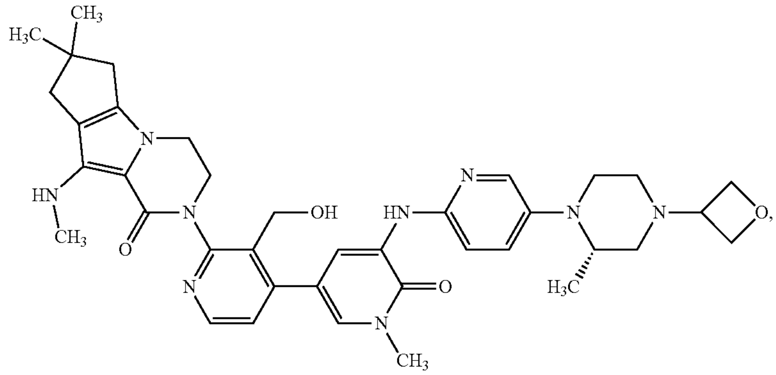
,
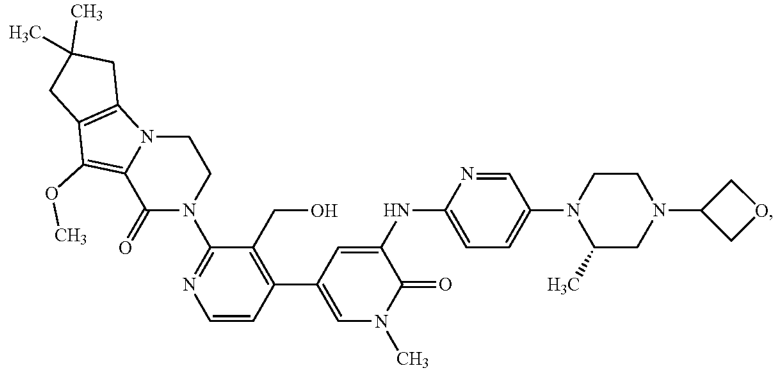
,
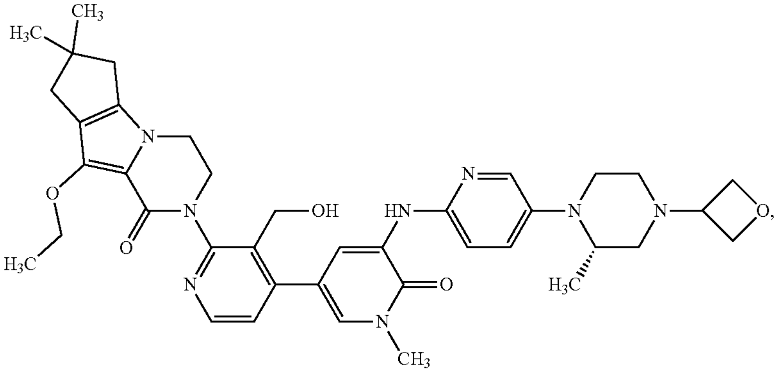
,
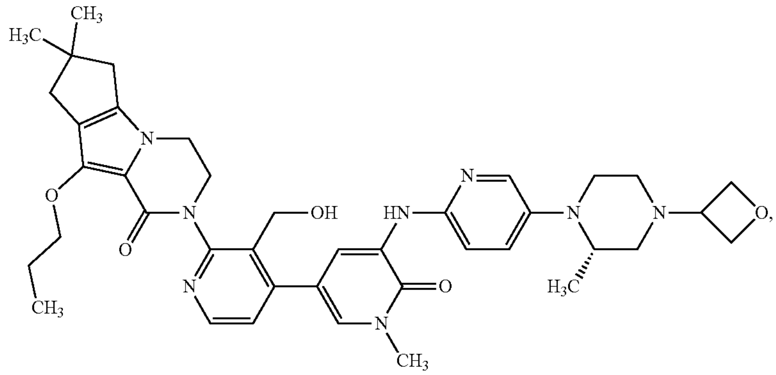
, and

-continued

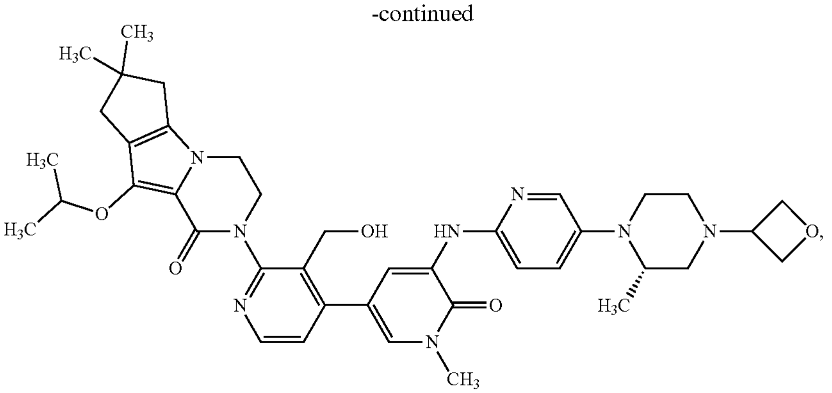

or a pharmaceutically acceptable salt or tautomer thereof.

6. A pharmaceutical composition comprising at least one pharmaceutically acceptable carrier or diluent and a therapeutically effective amount of the compound according to claim 1, or a pharmaceutically acceptable salt, stereoisomer, or tautomer thereof.

7. A method for inhibiting Bruton's tyrosine kinase activity in a subject, wherein the method comprises administering to the subject in need thereof a therapeutically effective amount of the compound according to claim 1, or a pharmaceutically acceptable salt, stereoisomer, or tautomer thereof.

8. The method according to claim 7, wherein the subject has a Bruton's tyrosine kinase-mediated disease or disorder selected from the group consisting of an autoimmune disorder, cancer, and an inflammatory disease.

9. The method according to claim 8, wherein:

(a) the cancer is selected from the group consisting of esophageal cancer, leukemia, lung cancer, lymphoma, pancreatic cancer, rectal cancer, and thyroid cancer; and (b) the autoimmune disorder or inflammatory disease is selected from the group consisting of an allergic reaction, arthritis, asthma, chronic obstructive pulmonary disease, Crohn's disease, inflammatory bowel disease, multiple sclerosis, organ transplant rejection, psoriasis, rhinitis, systemic lupus erythematosus, and thrombocytopenic purpura.

10. A method for inhibiting Bruton's tyrosine kinase activity in a subject, wherein the method comprises administering to the subject in need thereof a therapeutically effective amount of the pharmaceutical composition according to claim 6.

11. The method according to claim 10, wherein the subject has a Bruton's tyrosine kinase-mediated disease or disorder selected from the group consisting of an autoimmune disorder, cancer, and an inflammatory disease.

12. The method according to claim 11, wherein:

(a) the cancer is selected from the group consisting of esophageal cancer, leukemia, lung cancer, lymphoma, pancreatic cancer, rectal cancer, and thyroid cancer; and (b) the autoimmune disorder or inflammatory disease is selected from the group consisting of an allergic reaction, arthritis, asthma, chronic obstructive pulmonary disease, Crohn's disease, inflammatory bowel disease, multiple sclerosis, organ transplant rejection, psoriasis, rhinitis, systemic lupus erythematosus, and thrombocytopenic purpura.

13. A process for preparing a compound of formula I-12:

I-12

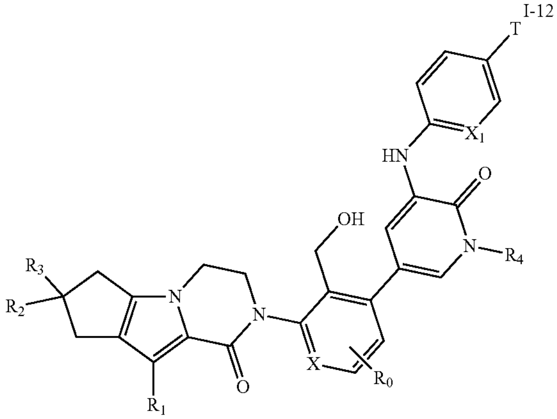

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N;

$R_0$ is H;

$R_4$ is $C_{1-6}$ alkyl;

$X_1$ is N;

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

$T_1$ is $C_{1-6}$ alkyl; and $T_2$ is $C_{1-6}$ alkyl or 3- to 6-membered heterocycloalkyl;

wherein the process comprises the following steps:

(1) reacting a compound of formula I-1:

I-1

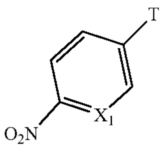

wherein:

$X_1$ is N; and

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

with a reducing agent 1 selected from the group consisting of borane dimethyl sulfoxide, borane tetrahydrofuran, lithium aluminum hydride, and reducing iron powder, to provide a compound of formula I-2:

I-2

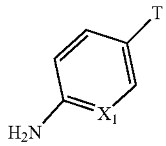

wherein:

$X_1$ is N; and

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

(2) reacting the compound of formula I-2 provided in step (1) above with a compound of formula Int 3:

Int 3

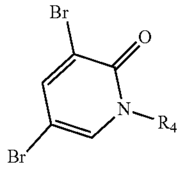

wherein:

$R_4$ is $C_{1-6}$ alkyl;

in the presence of a catalyst selected from the group consisting of 1,1'-binaphthyl-2,2'-bis(diphenylphosphine), [1,1'-bis(diphenylphosphino)ferrocene]palladium dichloride, 4,5-bis(diphenylphosphino)-9,9-dimethylxanthene, cuprous iodide, 2-dicyclohexylphosphine-2,4,6-triisopropylbiphenyl, palladium acetate, 1,10-phenanthroline, tetrakis(triphenylphosphine)palladium, and tris(dibenzylideneacetone)dipalladium, to provide a compound of formula I-3:

I-3

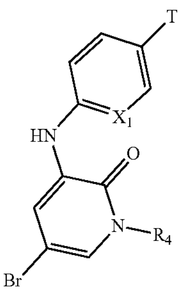

wherein:

$R_4$ is $C_{1-6}$ alkyl;

$X_1$ is N; and

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

(3) reacting the compound of formula I-3 provided in step (2) above with bis(pinacolato)diboron in the presence of a catalyst selected from the group consisting of 1,1'-binaphthyl-2,2'-bis(diphenylphosphine), [1,1'-bis(diphenylphosphino)ferrocene]palladium dichloride, 4,5-bis(diphenylphosphino)-9,9-dimethylxanthene, cuprous iodide, 2-dicyclohexylphosphine-2,4,6-triisopropylbiphenyl, palladium acetate, 1,10-phenanthroline, tetrakis(triphenylphosphine)palladium, and tris(dibenzylideneacetone)dipalladium, to provide a compound of formula I-4:

I-4

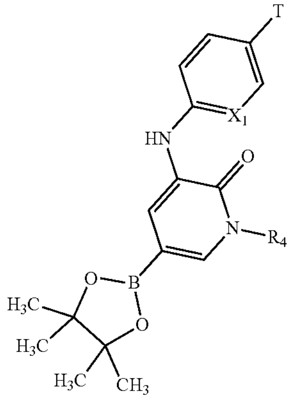

wherein:

$R_4$ is $C_{1-6}$ alkyl;

$X_1$ is N; and

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

(4) reacting the compound of formula I-4 provided in step (3) above with a compound of formula I-10:

I-10

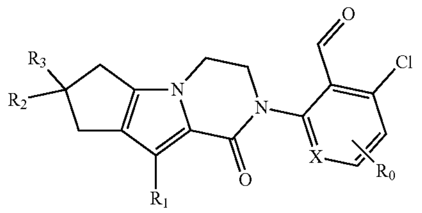

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N; and $R_0$ is H;

in the presence of a catalyst selected from the group consisting of 1,1'-binaphthyl-2,2'-bis(diphenylphosphine), [1,1'-bis(diphenylphosphino)ferrocene]palladium dichloride, 4,5-bis(diphenylphosphino)-9,9-dimethylxanthene, cuprous iodide, 2-dicyclohexylphosphine-2,4,6-triisopropylbiphenyl, palladium acetate, 1,10-phenanthroline, tetrakis(triphenylphosphine)palladium, and tris(dibenzylideneacetone)dipalladium, to provide a compound of formula I-11:

I-11

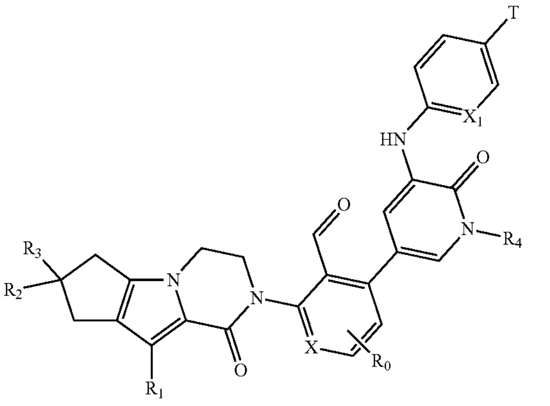

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N;

$R_0$ is H;

$R_4$ is $C_{1-6}$ alkyl;

$R_1$ is H or $C_{1-3}$ alkyl;

$X_1$ is N;

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

$T_1$ is $C_{1-6}$ alkyl; and $T_2$ is $C_{1-6}$ alkyl or 3- to 6-membered heterocycloalkyl; and (5) reacting the compound of formula I-11 provided in step (4) above with a reducing agent 2 selected from the group consisting of potassium borohydride, sodium borohydride, sodium cyanoborohydride, and sodium triacetylborohydride, to provide a compound of formula I-12:

I-12

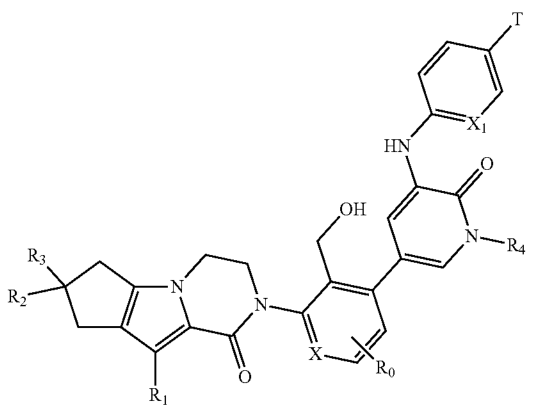

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N;

$R_0$ is H;

$R_4$ is $C_{1-6}$ alkyl;

$X_1$ is N;

T is a nitrogen-containing 5- or 6-membered heterocycloalkyl, wherein the 5- or 6-membered heterocycloalkyl is substituted by one $T_1$ substituent, one $T_2$ substituent, or one $T_1$ substituent and one $T_2$ substituent;

$T_1$ is $C_{1-6}$ alkyl; and $T_2$ is $C_{1-6}$ alkyl or 3- to 6-membered heterocycloalkyl.

14. The process of claim 13, wherein step (4) of the process further comprises:

(4a) reacting a compound of formula I-5:

I-5

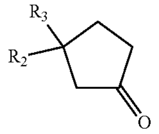

wherein:

$R_2$ is $C_{1-3}$ alkyl; and $R_3$ is $C_{1-3}$ alkyl;

with phosphorous oxychloride ($POCl_3$), to provide a compound of formula I-6:

I-6

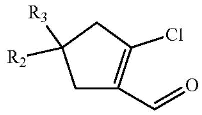

wherein:

$R_2$ is $C_{1-3}$ alkyl; and $R_3$ is $C_{1-3}$ alkyl;

(4b) reacting the compound of formula I-6 provided in step (4a) above with a compound of the following formula:

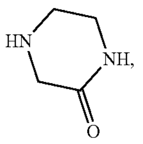

in the presence of diisopropylethanolamine (DIPEA), to provide a compound of formula I-7:

I-7

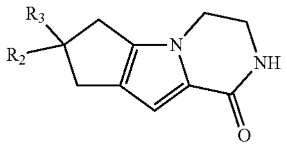

wherein:

$R_2$ is $C_{1-3}$ alkyl; and $R_3$ is $C_{1-3}$ alkyl;

(4c) reacting the compound of formula I-7 provided in step (4b) above with N-bromosuccinimide (NBS), to provide a compound of formula I-8:

I-8

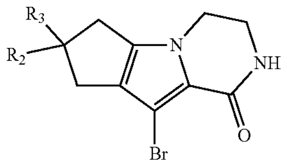

wherein:

$R_2$ is $C_{1-3}$ alkyl; and $R_3$ is $C_{1-3}$ alkyl;

(4d) reacting the compound of formula I-8 provided in step (4c) above with (i) n-butyllithium (n-BuLi) or (ii) a catalyst selected from the group consisting of 1,1'-binaphthyl-2,2'-bis(diphenylphosphine), [1,1'-bis(diphenylphosphino)ferrocene]palladium dichloride, 4,5-bis(diphenylphosphino)-9,9-dimethylxanthene, cuprous iodide, 2-dicyclohexylphosphine-2,4,6-triisopropylbiphenyl, palladium acetate, 1,10-phenanthroline, tetrakis(triphenylphosphine)palladium, and tris(dibenzylideneacetone)dipalladium, to provide a compound of formula I-9:

I-9

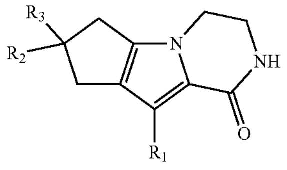

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl; and $R_3$ is $C_{1-3}$ alkyl; and (4e) reacting the compound of formula I-9 provided in step (4d) above with a compound of the following formula:

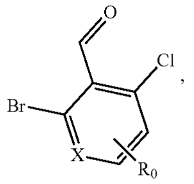

wherein:

$R_0$ is H;

in the presence of a catalyst selected from the group consisting of 1,1'-binaphthyl-2,2'-bis(diphenylphosphine), [1,1'-bis(diphenylphosphino)ferrocene]palladium dichloride, 4,5-bis(diphenylphosphino)-9,9-dimethylxanthene, cuprous iodide, 2-dicyclohexylphosphine-2,4,6-triisopropylbiphenyl, palladium acetate, 1,10-phenanthroline, tetrakis(triphenylphosphine)palladium, and tris(dibenzylideneacetone)dipalladium, to provide a compound of formula I-10:

I-10

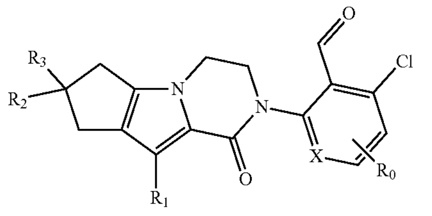

wherein:

$R_1$ is halogen, CN, $C_{1-6}$ alkyl, $CF_3$, $NH_2$, $NHC_{1-6}$ alkyl, or $OC_{1-6}$ alkyl;

$R_2$ is $C_{1-3}$ alkyl;

$R_3$ is $C_{1-3}$ alkyl;

X is N; and $R_0$ is H.

* * * * *